(12) United States Patent
Koch et al.

(10) Patent No.: US 11,998,740 B2
(45) Date of Patent: Jun. 4, 2024

(54) SYSTEMS AND METHODS FOR PROVIDING PERSONALIZED TARGETED NON-INVASIVE STIMULATION TO A BRAIN NETWORK

(71) Applicant: Sinaptica Therapeutics, Inc., Cambridge, MA (US)

(72) Inventors: Giacomo Koch, Rome (IT); Emiliano Santarnecchi, Brookline, MA (US)

(73) Assignee: Sinaptica Therapeutics, Inc., Cambridge, MA (US)

( * ) Notice: Subject to any disclaimer, the term of this patent is extended or adjusted under 35 U.S.C. 154(b) by 0 days.

(21) Appl. No.: 18/326,171

(22) Filed: May 31, 2023

(65) Prior Publication Data
US 2023/0381512 A1   Nov. 30, 2023

Related U.S. Application Data

(63) Continuation of application No. PCT/US2022/036115, filed on Jul. 5, 2022.
(Continued)

(51) Int. Cl.
*A61N 1/36* (2006.01)
*A61N 2/00* (2006.01)

(52) U.S. Cl.
CPC ..... *A61N 1/36031* (2017.08); *A61N 1/36025* (2013.01); *A61N 2/006* (2013.01)

(58) Field of Classification Search
CPC ............ A61N 1/36031; A61N 1/36025; A61N 2/006; A61N 1/3603; A61N 1/40
See application file for complete search history.

(56) References Cited

U.S. PATENT DOCUMENTS

| 8,151,317 | B2 | 4/2012 | Hinton et al. |
| 8,805,516 | B2 | 8/2014 | Bentwich |

(Continued)

FOREIGN PATENT DOCUMENTS

| CN | 116870366 A | 7/2023 |
| EP | 3106202 A1 | 12/2016 |

OTHER PUBLICATIONS

International Search Report and Written Opinion of the International Searching Authority for International Application No. PCT/US22/36115, dated Feb. 16, 2023.
(Continued)

*Primary Examiner* — Amanda K Hulbert
*Assistant Examiner* — Philip C Edwards
(74) *Attorney, Agent, or Firm* — PIERCE ATWOOD LLP

(57) ABSTRACT

Disclosed herein are devices, systems, and methods for ameliorating or treating or preventing Alzheimer's Disease and related dementias. Methods may include using individual patients' data to identify the optimal treatment target (s) as well as the stimulation intensity, frequency, or waveform, or any combination thereof, for transcranial electromagnetic induction delivered via a device as in the case of Transcranial Magnetic Stimulation. Systems and methods include a platform or infrastructure for treatment delivery and data processing. In some embodiments, methods are applied to restore cognitive function, ameliorate clinical symptoms, modify altered mechanisms of plasticity, modulate cortical excitability and reactivity, or induce changes in local brain metabolism.

18 Claims, 19 Drawing Sheets

Related U.S. Application Data

(60) Provisional application No. 63/277,086, filed on Nov. 8, 2021, provisional application No. 63/218,625, filed on Jul. 6, 2021.

(56) References Cited

U.S. PATENT DOCUMENTS

| | | | |
|---|---|---|---|
| 9,492,114 | B2 | 11/2016 | Reiman |
| 9,662,492 | B1 | 5/2017 | Tucker et al. |
| 10,485,470 | B2 | 11/2019 | Dolev et al. |
| 10,758,174 | B2 | 9/2020 | Widge et al. |
| 11,406,841 | B2 | 8/2022 | Ho |
| 11,786,747 | B2 | 10/2023 | Malish |
| 11,793,456 | B2 | 10/2023 | Malish |
| 2013/0267761 | A1 | 10/2013 | Bentwich |
| 2015/0011864 | A1 | 1/2015 | Reisberg |
| 2015/0119689 | A1 | 4/2015 | Pascual-Leone et al. |
| 2015/0174418 | A1 | 6/2015 | Tyler et al. |
| 2016/0220836 | A1* | 8/2016 | Parks ................ A61N 1/36025 |
| 2017/0079538 | A1 | 3/2017 | Liang et al. |
| 2017/0319063 | A1 | 11/2017 | Verdooner et al. |
| 2018/0014772 | A1 | 1/2018 | Dolev et al. |
| 2018/0236255 | A1 | 8/2018 | Etkin |
| 2019/0126055 | A1* | 5/2019 | Etkin ................... A61N 2/02 |
| 2019/0388020 | A1* | 12/2019 | Stauch ................ A61B 5/0022 |
| 2020/0214569 | A1 | 7/2020 | Kim |
| 2020/0352443 | A1 | 11/2020 | Fox |
| 2021/0023378 | A1 | 1/2021 | Intrator |
| 2021/0045645 | A1 | 2/2021 | Aur |
| 2021/0353224 | A1 | 11/2021 | Etkin et al. |
| 2023/0082594 | A1 | 3/2023 | Hagedorn |
| 2023/0113681 | A1 | 4/2023 | Fogel et al. |

OTHER PUBLICATIONS

De Boer et al., "A Casual Role for the Right Angular Gyrus in Self-Location Mediated Perspective Taking", Scientific Reports, (2020), pp. 1-10, vol. 10:19229.

Koch et al., "Transcranial Magnetic Stimulation of the Precuneus Enhances Memory and Neural Activity in Prodromal Alzheimer's Disease", NeuroImage, (2018), pp. 302-311, vol. 169.

International Search Report and Written Opinion from the International Searching Authority for Application No. PCT/US23/69421, dated Feb. 21, 2024.

* cited by examiner

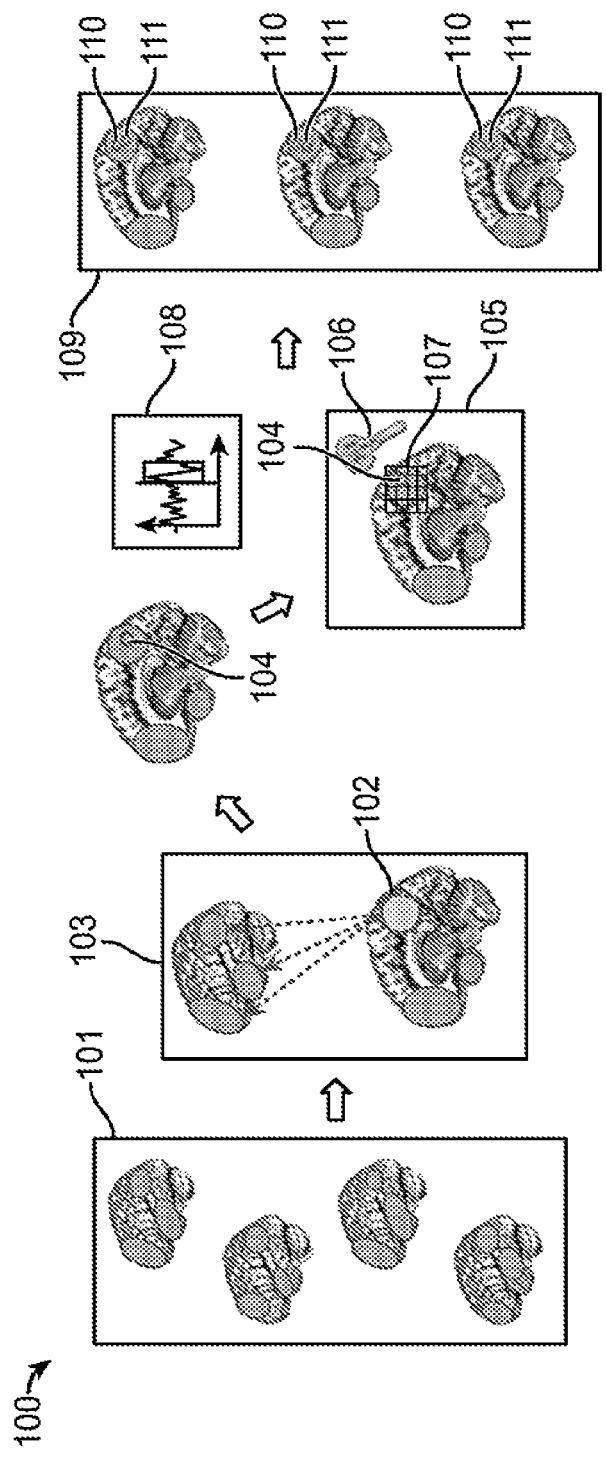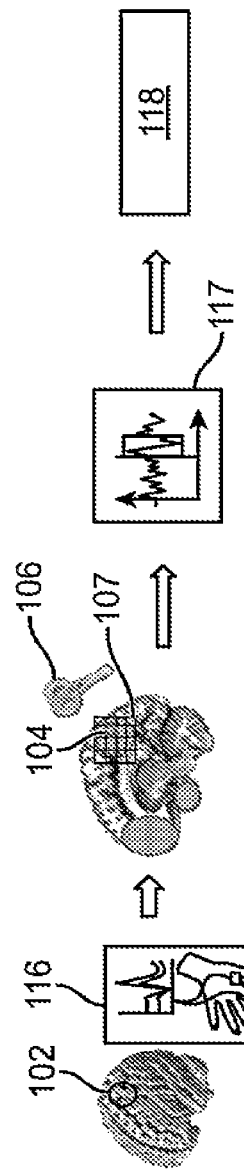
Figure 1A
Figure 1B

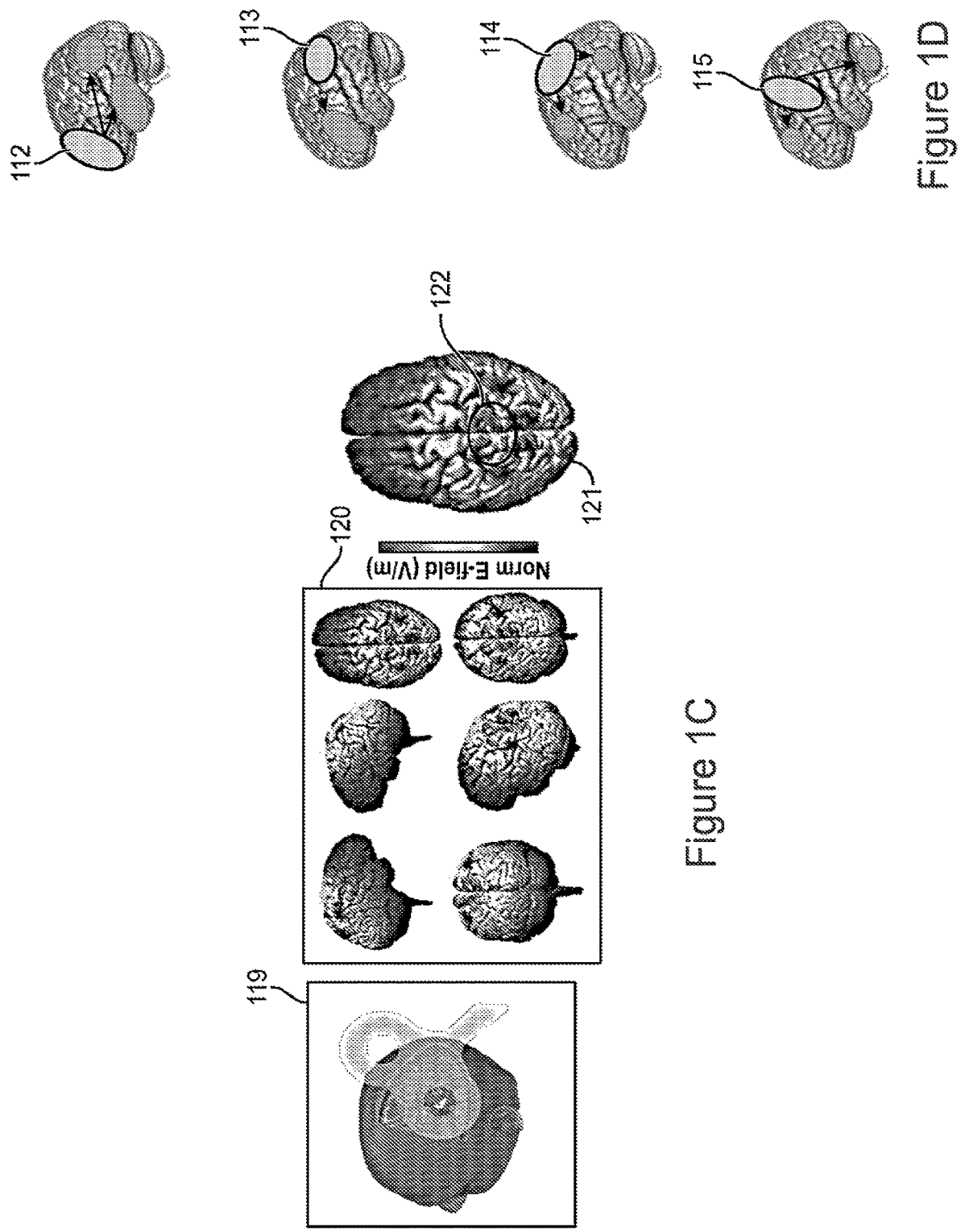

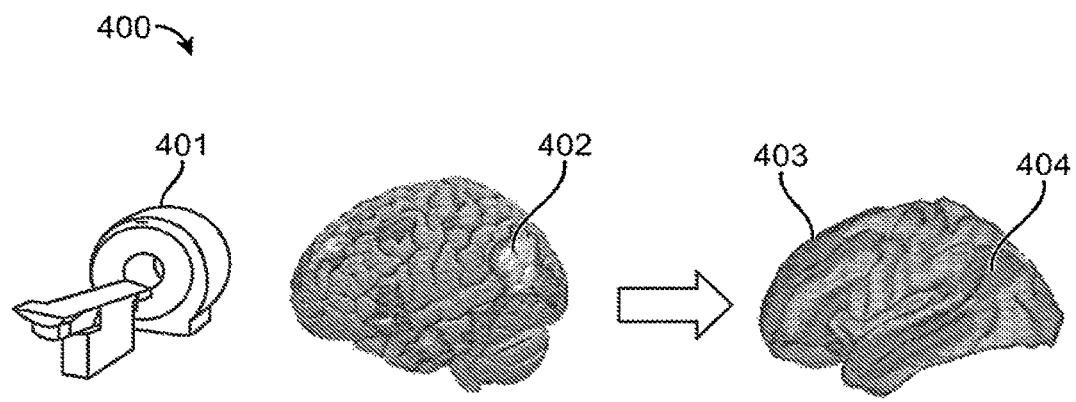
Figure 4A
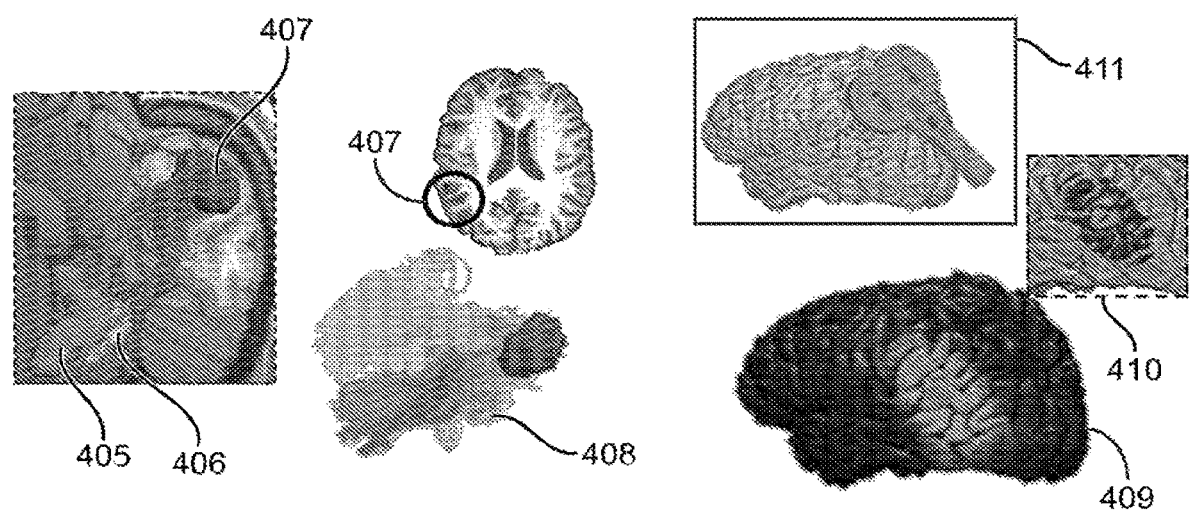
Figure 4B
Figure 4C

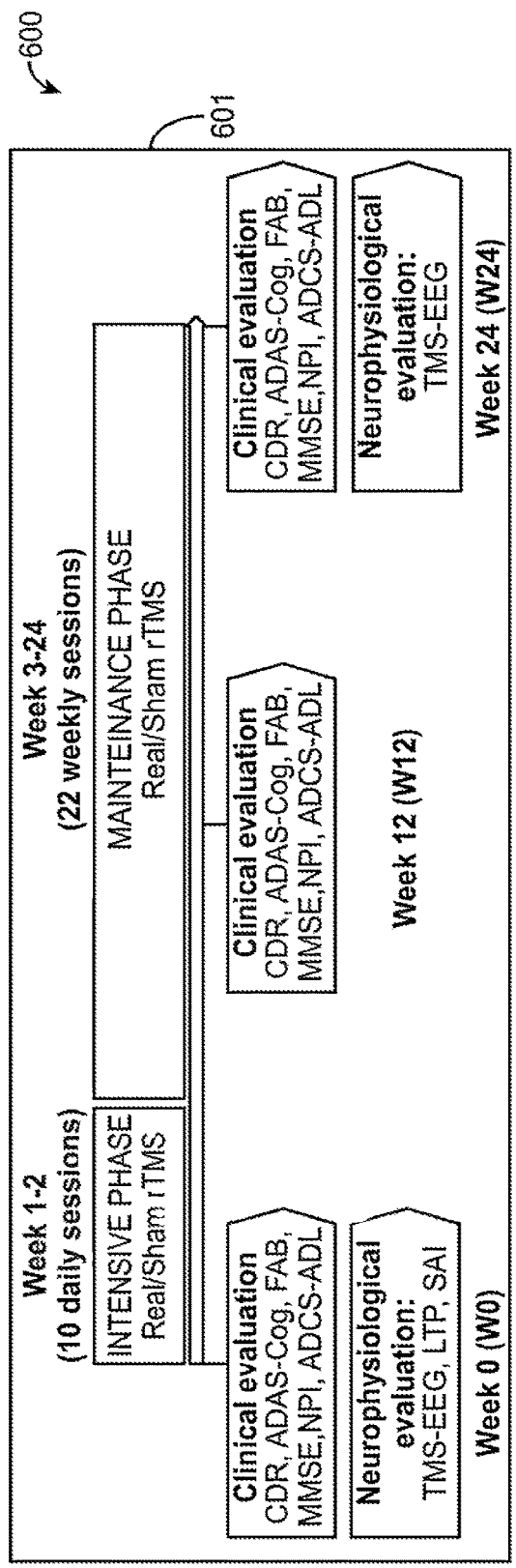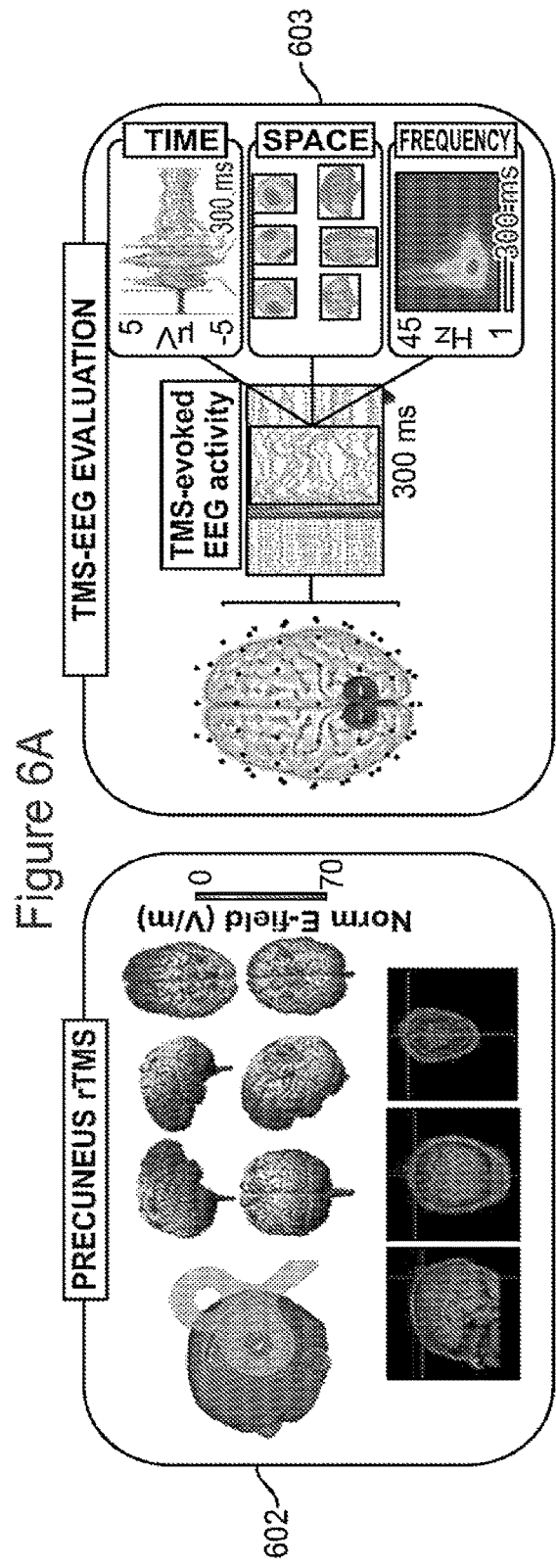
Figure 6A
Figure 6B
Figure 6C

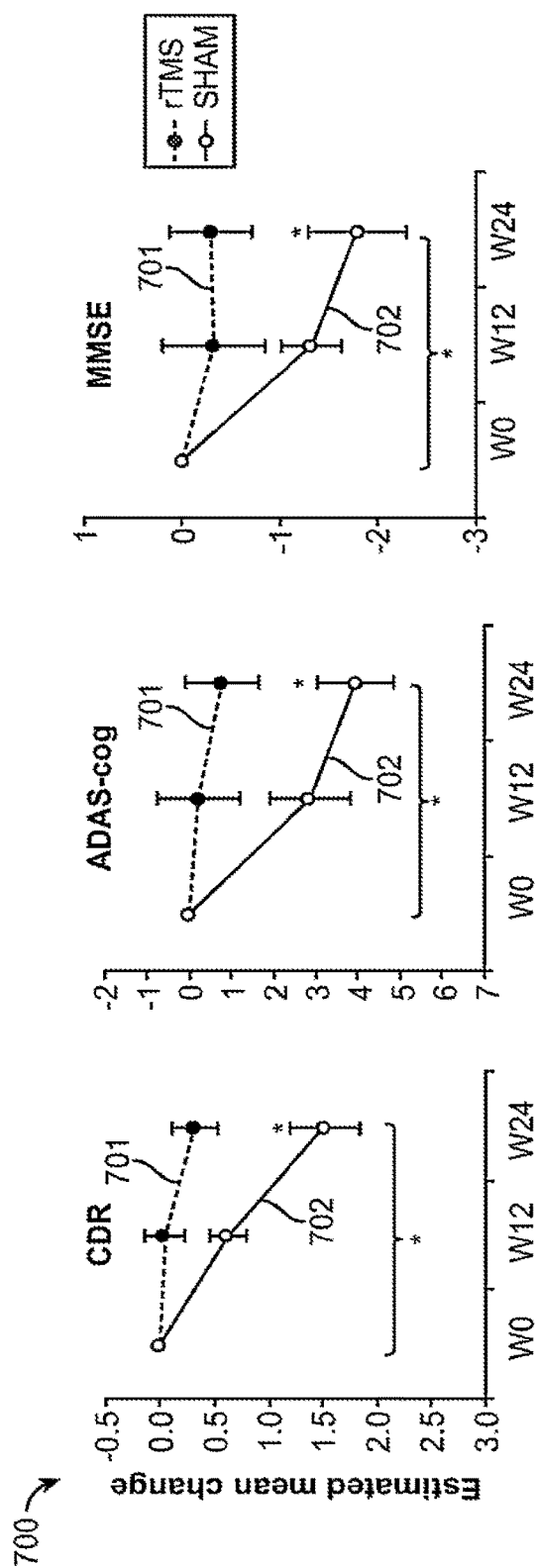

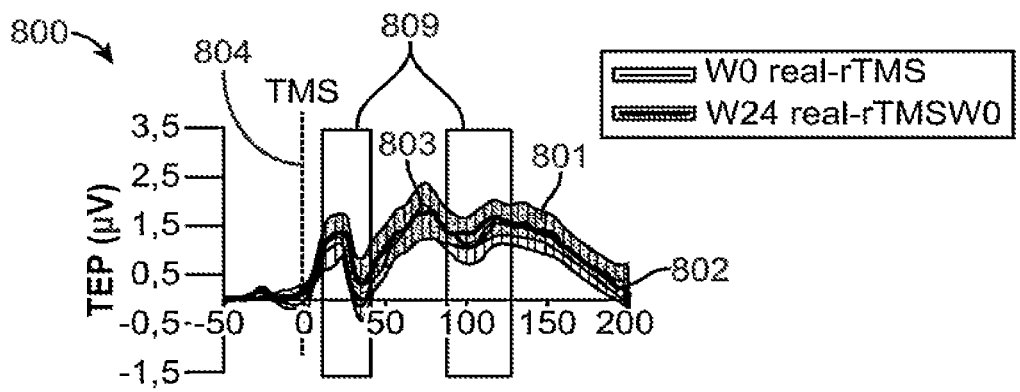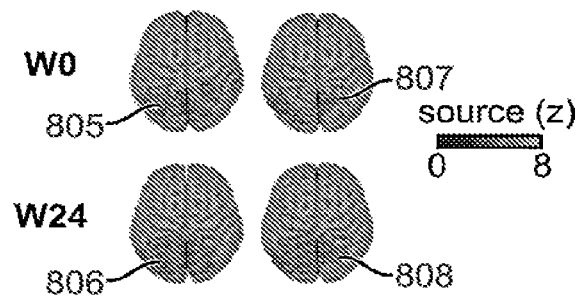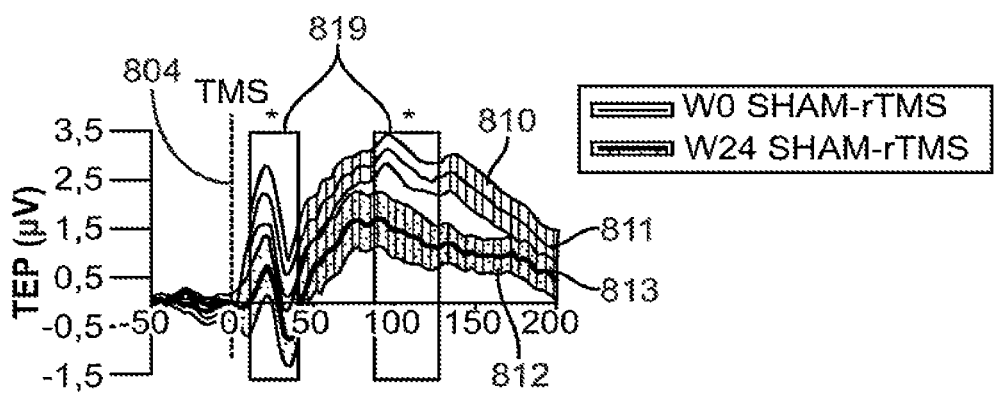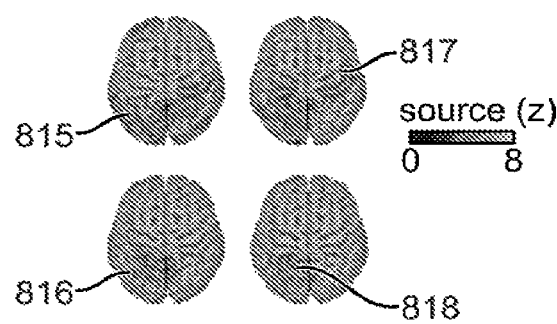
Figure 8A

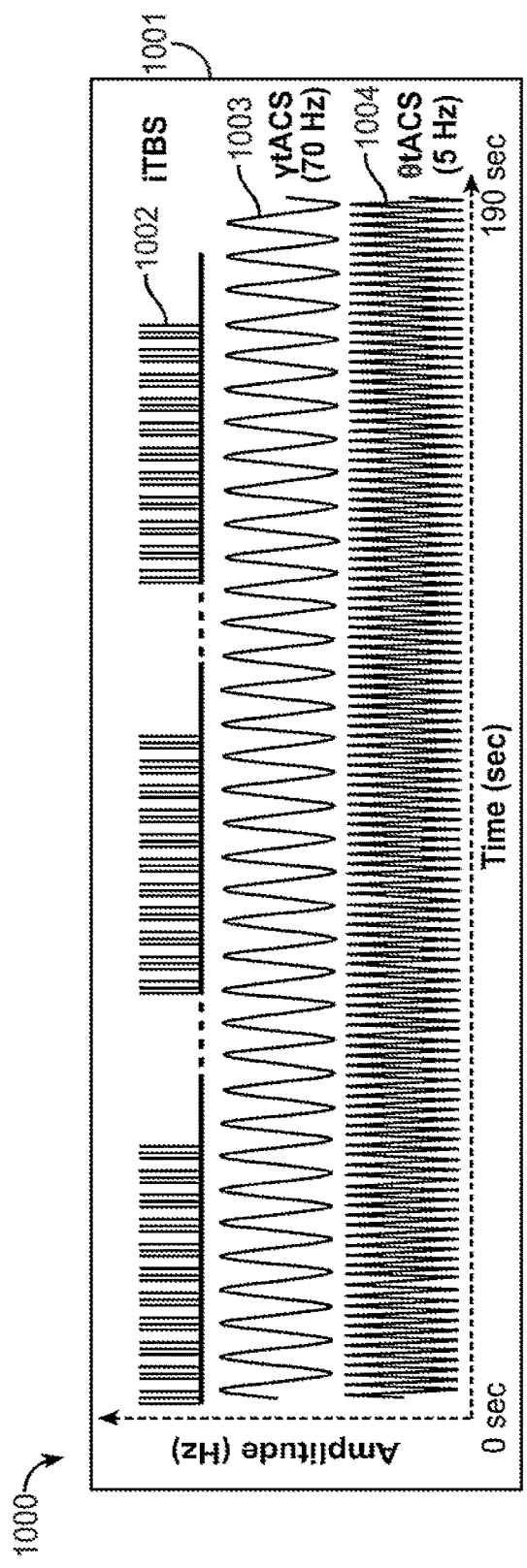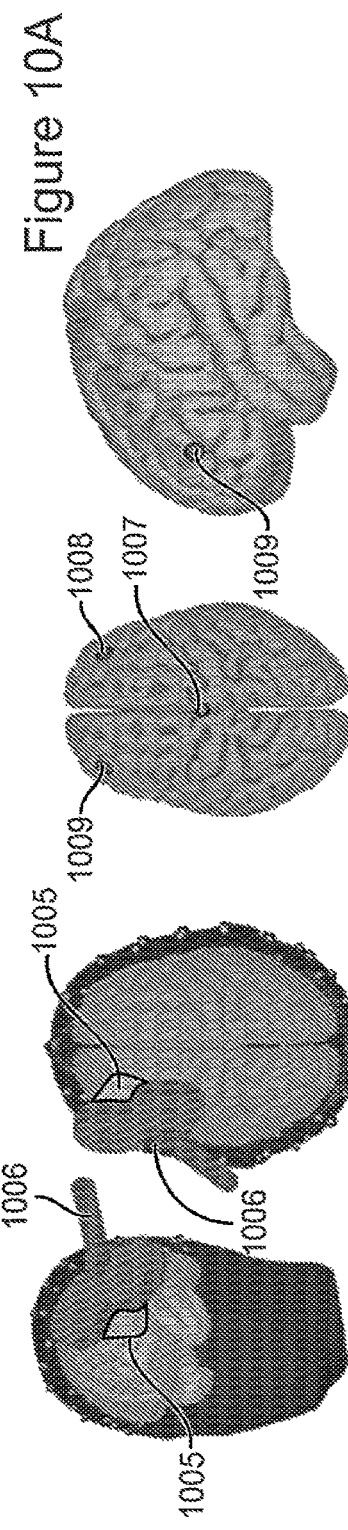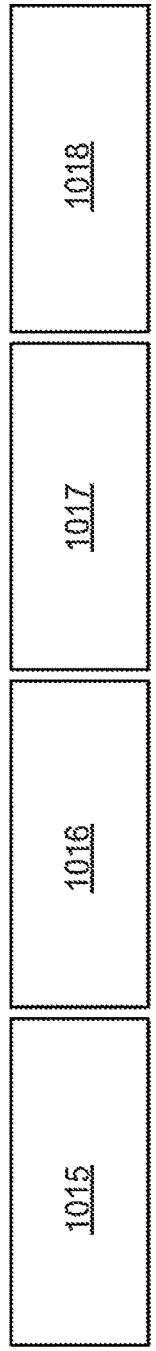

SYSTEMS AND METHODS FOR PROVIDING PERSONALIZED TARGETED NON-INVASIVE STIMULATION TO A BRAIN NETWORK

CROSS-REFERENCE

This application claims priority to International Application No. PCT/US2022/036115, filed Jul. 5, 2022, which claims priority to U.S. Provisional Application No. 63/218,625, filed Jul. 6, 2021, and U.S. Provisional Application No. 63/277,086, filed Nov. 8, 2021, each of which is incorporated herein by reference in its entirety.

BACKGROUND

Alzheimer's disease (AD) is considered the most harmful form of dementia in the elderly population. Currently, conventional care for AD patients is only reflected by cholinergic and glutamatergic drugs even though these treatments have limited efficacy and often cause adverse side effects. At present, there are no effective treatments, which is mainly due to the lack of understanding of the fundamental pathophysiology. Overall, there is an urgent need in the art for new non-drug-related therapies.

SUMMARY

It is appreciated by the inventors that existing techniques for treating neurological and psychiatric diseases with non-invasive stimulation may be improved by personalizing the location and/or stimulation parameters for individual patients. Disclosed herein are methods relating to identifying a location in a brain of a patient to which non-invasive stimulation is to be provided. A plurality of brain regions in a brain network (e.g., the Default Mode Network) may be identified based on neuroimaging data (e.g., functional magnetic resonance data, diffusion tensor imaging data, etc.). Within one of the plurality of brain regions in the brain network functional connectivity with one or more other of the brain regions in the brain network may be assessed to determine a sub-region of the brain region most strongly connected with other regions in the brain network.

Aspects disclosed herein provide a method for identifying a first location in a brain of a subject suitable for non-invasive stimulation to treat or ameliorate a neurological or psychiatric disease, the method comprising: a) identifying, from scan data of the brain of the subject, a plurality of brain regions forming a brain network; and b) determining, within a first brain region of the plurality of brain regions, as the first location suitable for non-invasive stimulation to treat or ameliorate the neurological or psychiatric disease, a sub-region of the first brain region strongly connected to one or more other brain regions of the plurality of brain regions. In some embodiments, a target brain region is defined based on the average connectivity within its network of origin, the connectivity with a specific network, the connectivity with multiple other networks. In some embodiments, measures of network controllability are used instead of connectivity. In some embodiments, one or more of measures of network efficiency, modularity, clustering, evolvability, or resilience are used instead of connectivity. In some embodiments, a target brain region is defined based on simulated data estimating the propagation of a TMS pulse across the rest of non-stimulated brain structures, where the estimation takes into account the initial intensity of the pulse, pulse shape, integrity of connections between targeted region or other brain structures or networks. In some embodiments, the estimation takes into account a decay function approximating the progressive loss of energy of the original perturbation as a function of time and number, sequence of regions, or nodes indirectly reached by stimulation.

In some embodiments, TMS-EEG functional mapping is used to simultaneously determine both location and stimulation parameters for non-invasive brain stimulation. In some embodiments, one or more characteristics of evoked responses to brain stimulation at one or more locations within a brain region may be used to determine both the optimal location for targeted non-invasive stimulation and also stimulation characteristics (e.g., stimulation frequency, intensity, amplitude) personalized to the individual patient to provide an optimized brain response, for example, to treat a neurological or psychiatric disorder.

Aspects disclosed herein provide a method for determining a personalized stimulation target in a brain region to treat or ameliorate a neurological or psychiatric disease in a subject, the method comprising: a) non-invasively stimulating each location of a plurality of locations in a brain region of a subject; b) sensing, in response to the stimulation provided, at least one evoked potential; and c) selecting as a personalized stimulation target for the subject, one of the locations of the plurality of locations that is suitable for providing therapeutically effective non-invasive stimulation to treat or ameliorate the neurological or psychiatric disease, wherein the selecting is based on the at least one characteristic of the at least one evoked potential. In some embodiments, the method involves personalizing a brain stimulating target by identifying a brain sub-region, and further refining a stimulation location of the brain region using TMS-EEG functional mapping ("Opti-Search" procedure). In some embodiments, stimulation may sequentially be provided to a plurality of locations within the sub-region and evoked responses to the stimulation may be sensed using, for example, electroencephalography (EEG) or another suitable sensing technique. In some embodiments, a personalized stimulation target within the brain subregion may be selected based, at least in part, on an analysis of the evoked responses to the stimulation. In some embodiments, the intensity or amplitude of brain stimulation may be selected by adjusting a baseline intensity of stimulation determined using other techniques. In some embodiments, a patient's resting motor threshold may be used to establish a baseline stimulation intensity and the baseline stimulation intensity may be refined based, at least in part, on one or more characteristic of evoked responses sensed during TMS-EEG functional mapping as described herein. In some embodiments, determination of a personalized stimulation target location may be performed using neuroimaging data to first identify a sub-region of a brain region most strongly connected to other brain regions in a brain network, using concepts and methods related to one or more of brain connectomics, brain connectivity, network theory, graph theory, or control theory analysis. In some embodiments, the personalization algorithm used to define brain targets and stimulation parameters for each patient can be applied for the treatment or prevention of neurological and psychiatric diseases associated with alteration of brain networks similar to those characterizing AD patients (e.g., Default Mode Network), or other networks with a role in cognitive processes (e.g., Dorsal Attention Network, Fronto-Parietal Cognitive Control Network). In some embodiments, the personalization algorithm used to define brain targets and stimulation parameters for each patient include analysis of intra-network and inter-network dynamics, in order to determine a hierarchy of network targets. In some embodiments, the personalization algorithm used to define brain stimulation targets for each patient can be applied to other neuroimaging data sources, including structural MRI, Diffusion MRI, Perfusion MRI, or PET imaging data.

In some embodiments, the systems and methods described herein allow for the modulation of oscillatory brain activity, including but not limited to changes in fast activity in the gamma frequency band. In some embodiments, the present systems and methods can be applied to the treatment or prevention of various diseases associated with protein deposits and with pathophysiological mechanisms associated with protein accumulation and interneuron pathology as in the case of AD. In some embodiments, the present systems and methods allow for the slowing of cognitive decline, comprising identifying a brain sub-region, further refining a stimulation location of the brain region, and applying repetitive transcranial magnetic stimulation to the stimulation location. In some embodiments, cognitive decline is slowed when the method is applied during temporal intervals from several days to several weeks, months, or years. In some embodiments, cognitive decline is slowed by changing brain activity in specific brain networks, including, but not limited to networks in patients with AD or in subjects at risk of developing AD.

In some embodiments, optimal TMS coil locations or brain targets or stimulation parameters, are determined by using biophysical electric field modeling of a realistic head model. In some embodiments, optimal TMS coil locations, brain targets, or stimulation parameters are determined by using normative data from a sample of AD patients. In some embodiments, optimal TMS coil locations, brain targets, or stimulation parameters are determined by estimating AD patients' white matter connectivity with subcortical regions of interest for AD patients. In some embodiments, optimal TMS coil locations, brain targets, or stimulation parameters are determined by using scalp coordinates derived from individual head measurements of a patient and combined with normative maps of spontaneous brain activity or activity during a specific cognitive task, such as an episodic memory task estimated from a sample of AD patients. In some embodiments, optimal TMS coil locations, brain targets, or stimulation parameters are determined by using individual brain scan data and EMG data in the absence of TMS-EEG data. In some embodiments, the realistic head model may be a multilayer finite element model of a realistic head that may be either generic or specific to a subject, e.g., from an MRI of a patient. In some embodiments, tissue boundaries may be derived from MR images (e.g., scalp, skull, cerebrospinal fluid, ventricles, grey and white matter) with or without additional brain scans, and the method may be used to calculate the induced electric field (E-field) in the head and on the cortex more specifically. In some embodiments, normative data from a sample of AD patients includes, but is not limited to, normative brain activation patterns during a specific cognitive task such as an episodic memory task, functional brain networks topographical maps, maps of metabolic activity or brain perfusion. In some embodiments, a non-limiting example of subcortical regions of interest for AD patients is the hippocampus for its role in memory processing. In some embodiments, cortical sites with strong connectivity with subcortical targets are selected for their higher probability to engage subcortical regions otherwise not directly targetable via TMS.

In some embodiments, optimal TMS coil locations or stimulation parameters may be determined by using individual brain scan data and EMG data in the absence of TMS-EEG data, by comparing a patient's brain scan and EMG data with normative brain scans, EMG and TMS-EEG data of a group of AD patients. In some embodiments, estimates of optimal stimulation intensity are inferred by the relationship between EMG data (e.g., cortical excitability) and its relationship with TMS-EEG data in AD patients, adjusted by scalp-cortex distance values extracted from a patient's brain scans. In some embodiments, a physiological computational model of the subject's brain derived from electrophysiological and biophysical data may also be used to define brain stimulation targets and optimize stimulation parameters, including, but not limited to, intensities, frequencies, duration, or waveforms, or any combination thereof. In some embodiments, a TMS-based intervention can be applied in combination with other interventions (TMS+other interventions=$T^2$ formulation), including, but not limited to, cognitive training programs or cognitive tasks or behavioral interventions, to amplify brain stimulation effects, amplify the effect of the second intervention, or create synergistic effects, or any combination thereof. In some embodiments, cognitive tasks or programs can be used to stabilize brain state and maximize the efficacy of a TMS-based intervention, to induce state-dependent effects, or to boost cognitive or behavioral performance. In some embodiments, a TMS-based intervention can be applied in combination with other brain stimulation techniques, to amplify TMS effects, amplify the effect of the second intervention, or create synergistic effects, or any combination thereof. In embodiments, TMS can be combined with transcranial direct current stimulation (tDCS), transcranial alternating current stimulation (tACS), or transcranial random noise stimulation (tRNS), or any combination thereof. In some embodiments, combination with electrical stimulation can be used to amplify endogenous oscillations, amplify long-term potentiation or depression effects of other brain stimulation protocols, stabilize brain activity during or before delivery of TMS-based interventions, modulate plasticity responses, or modulate cortico-spinal excitability and inhibition and excitation balance, or any combination thereof. In some embodiments, the TMS-based intervention includes, but is not limited to, patterned rTMS protocols such as Theta Burst stimulation, multi-pulse TMS and paired associative stimulation. In some embodiments, a TMS-based intervention can be applied in combination with drugs acting on the central nervous system, to amplify brain stimulation effects, amplify the effect of the second intervention, or create synergistic effects, or any combination thereof.

In some embodiments, parameters for the TMS-based intervention are computed via signal processing software and algorithms installed on a local hardware operated by trained personnel including, but not limited to, research scientists, laboratory technicians, research assistants, neurologists, psychiatrists, geriatricians, neurophysiologists, clinical technicians, or psychologists, or any combination thereof. In some embodiments, parameters for the TMS-based intervention are computed via signal processing software or algorithms installed on remote hardware with connectivity capabilities. In some embodiments, data collected on patients is streamed to a platform hosting code and software for optimal stimulation parameters definition (TMS-EEG functional mapping), and the resulting stimulation parameters are sent back to operators conducting the TMS-based treatment. In some embodiments, parameters for the TMS-based intervention are computed by applying machine learning or deep learning algorithms on the EEG, TMS, EMG, or brain scan data of a subject, via supervised or unsupervised feature selection procedures. In some embodiments, stimulation parameters for the TMS-based intervention, details on treatment course, data storage and processing, or scheduling of brain stimulation are hosted as part of a hybrid local or remote infrastructure and application programmers interfaces (API).

BRIEF DESCRIPTION OF THE DRAWINGS

For a more complete understanding of the present embodiments, including features and advantages, reference is now made to the detailed description of the embodiments along with the accompanying figures.

FIGS. 1A-1D provide exemplary methods for personalized target identification and definition of TMS intensity, according to an embodiment herein, wherein various options are provided. FIG. 1A shows a method for personalized target identification and definition of TMS intensity comprising gathering fMRI data of Alzheimer's Disease patients, creating an average default mode network map centered on the precuneus, creating a TMS-based functional search by measuring TMS-evoked potentials, and creating personalized targets for each brain. FIG. 1B shows a method for personalized target identification and definition of TMS intensity comprising measuring the resting motor threshold by measuring activity in the index finger while stimulating the precuneus, creating a TMS-based functional search by measuring TMS-evoked potentials, and determining personalized stimulation intensity. FIG. 1C shows a method for personalized target identification and definition of TMS intensity comprising positioning a TMS coil to generate biophysical modeling results and then estimating the induced electric field on a target region. FIG. 1D shows alternative targets for the default mode network and other functional brain networks relevant for Alzheimer's Disease.

FIG. 2A shows a functional network atlas comprised of various neural networks. FIG. 2B shows a method for target identification comprising morphing predefined brain activated patterns into individual patient anatomy by measuring brain activation during episodic memory processing in Alzheimer's disease patients. FIG. 2C shows a method for target identification using scalp coordinates to locate the optimal target distance and find the optimal first stimulation location on the scalp.

FIGS. 4A-4C provide exemplary methods for subcortical targeting via functional or structural connectome data, according to an embodiment herein, wherein various options are provided. FIG. 4A shows a method for subcortical targeting using MRI to measure episodic memory activation of the brain to show activated areas in a resting state functional MRI. FIG. 4B shows a method for subcortical targeting using MRI data of the hippocampus, parahippocampus, and left angular gyrus, as well as white matter tractography data. FIG. 4C shows a method for subcortical targeting using biophysical modeling of the brain to estimate the optimal intensity to activate the angular gyms and hippocampus via TMS.

FIGS. 6A-6C provide an exemplary study design measuring changes in brain reactivity after treatment, according to an embodiment herein. FIG. 6A shows an exemplary study design comprising clinical and neurophysiological evaluations at different time points separated by phases of sham or real rTMS administration. FIG. 6B shows the average location of the TMS coil on a scalp across patients visualized on a template head and biophysical modeling results based on a simulated induced electric field. FIG. 6C shows TMS-EEG data mapped across time, space, and frequency at target locations for one or more patients.

FIGS. 7A-7F provide an exemplary depiction of cognitive changes after treatment according to an embodiment herein. FIG. 7A shows a generalized linear mixed model of estimated mean change on the Clinical Dementia Rating scale across 24 weeks for rTMS and sham rTMS treatment. FIG. 7B shows a generalized linear mixed model of estimated mean change on the Alzheimer's Disease Assessment Scale—Cognitive 13-item scale across 24 weeks for rTMS and sham rTMS treatment. FIG. 7C shows a generalized linear mixed model of estimated mean change on the Mini-Mental State Exam across 24 weeks for rTMS and sham rTMS treatment. FIG. 7D shows a generalized linear mixed model of estimated mean change on the Alzheimer's Disease Cooperative Study Activities of Daily Living scale across 24 weeks for rTMS and sham rTMS treatment. FIG. 7E shows a generalized linear mixed model of estimated mean change on the Neuropsychiatric Inventory scale across 24 weeks for rTMS and sham rTMS treatment. FIG. 7F shows a generalized linear mixed model of estimated mean change on the Frontal Assessment Battery scale across 24 weeks for rTMS and sham rTMS treatment.

FIGS. 8A-8B provide an exemplary depiction of TMS-EEG results after treatment according to an embodiment herein. FIG. 8A shows a neurophysiological analysis of TMS-evoked cortical activity in the DMN-p-rTMS group compared to the sham-rTMS group. FIG. 8B shows a neurophysiological analysis which indicates that DMN source activity did not change in patients treated with DMN-p-rTMS but decreased in the sham-rTMS patient group.

FIGS. 10A-10D provide an exemplary TMS study protocol according to an embodiment herein, wherein various measured results are provided. FIG. 10A shows a brain wave graph comprised of responses to gamma transcranial Alternating Current Stimulation (γtACS), theta transcranial Alternating Current Stimulation (θtACS), and intermittent theta burst stimulation (iTBS). FIG. 10B shows stimulation of a chosen brain area with a tACS instrument. FIG. 10C shows depictions of brain areas for stimulation comprising the left dorsolateral prefrontal cortex, the right dorsolateral prefrontal cortex, or the vertex. FIG. 10D shows an experimental protocol comprised of TMS-EEG before stimulation at T0, iTBS-tACS stimulation, TMS-EEG immediately after stimulation at T1, and TMS-EEG 20 minutes after stimulation at T2.

DETAILED DESCRIPTION

Figure 2A:
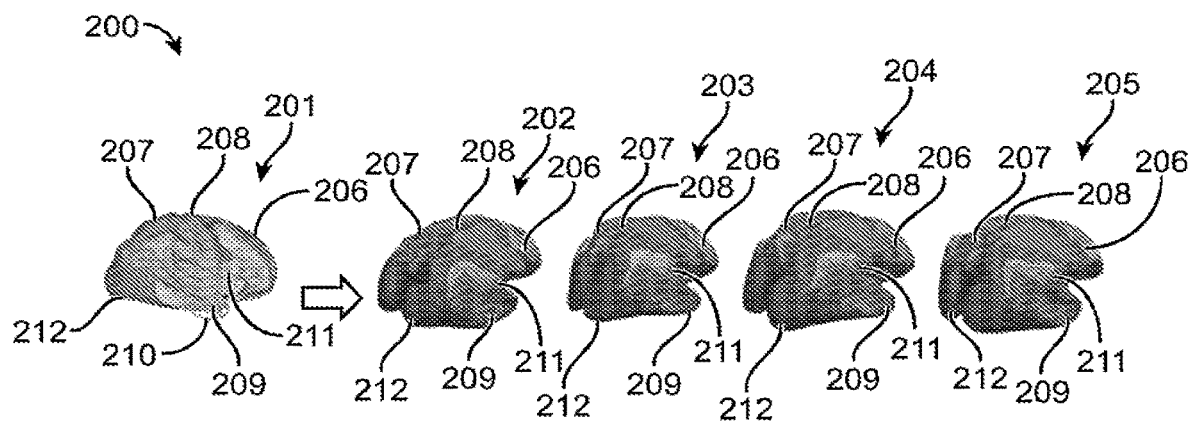
FIGS. 2A-2C provide exemplary methods for target identification via normative or custom brain activity templates, according to an embodiment herein, wherein various options are provided.

Provided herein are devices, systems, and methods for ameliorating or treating or preventing Alzheimer's Disease and related dementias, or any combination thereof, including, but not limited to, preclinical and early stages of the disease (e.g., Mild Cognitive Impairment) as well as more advanced stages. In some embodiments, the methods use individual patients' data to identify the optimal treatment target(s) as well as the stimulation intensity, frequency, or waveform, or any combination thereof, used for transcranial electromagnetic induction delivered via a device as in the case of Transcranial Magnetic Stimulation (TMS). In some embodiments, data for defining optimal stimulation parameters are derived from, among other sources, electrophysiological recordings (e.g., electroencephalography—EEG, electromyography—EMG), magnetic resonance imaging (e.g., MRI, fMRI, DTI) and estimates of induced electrical field in the brain obtained via biophysical modeling. In some embodiments, methods include, but are not limited to, solutions for targeting brain networks altered in neurological diseases such as Alzheimer's Disease and Related Dementia. In some embodiments, as a non-limiting example, methods target the default mode network (DMN) and its primary network node, the precuneus region. In some embodiments, methods include, but are not limited to, details of a treatment plan based on repeated TMS sessions able to slow down cognitive and clinical decline in patients with Alzheimer's Disease over a period of 6 months. In some embodiments, systems and methods include, but are not limited to, a platform or infrastructure for treatment delivery and data processing. In some embodiments, methods are applied to restore cognitive function, ameliorate clinical symptoms, modify altered mechanisms of plasticity, modulate cortical excitability and reactivity, or induce changes in local brain metabolism, or any combination thereof.

Synaptic dysfunction could be a central element of Alzheimer's disease (AD) pathophysiology. For example, synaptic breakdown is an early event that heralds neuronal degeneration. The weakening of synaptic transmission may play a key role in the pathogenesis of AD. Transcranial magnetic stimulation (TMS) is a novel approach able to identify the early signatures of synaptic dysfunction characterizing AD pathophysiology. Treatments based on multiple sessions of rTMS have the potential for influencing cognition in people with neurodegenerative diseases. rTMS applied to individuals with mood disorders and depression may be able to influence cognitive processes, while also being safe and painless. Exposing individuals to multiple sessions of rTMS over an extensive period (i.e., several weeks) will likely have more impact on modulating long-lasting plasticity and behavior.

From a neurobiological point of view, rTMS may lead to substantial clinical improvements by promoting changes in synaptic plasticity, which is an important biological mechanism underlying learning and memory. In particular, Long Term Potentiation (LTP) is a leading candidate to target since it has been previously linked to individual differences in cognitive function. LTP-like cortical plasticity may be impaired at the early stages of AD and may be associated with verbal memory impairment. Therefore, high-frequency rTMS can be used to enhance LTP-like cortical plasticity in AD patients at the early stages of the disease to slow down disease progression. A combination of brain plasticity and reactivity measures, captured for instance, via the combination of TMS and electroencephalography (EEG), and cognitive scores could confirm whether rTMS produces changes at both the local and global levels. In particular, TMS-EEG provides an innovative method to directly probe local and widespread cortical dynamics not only in clinical practice but also in the assessment of effects of clinical interventions. Early TMS-Evoked potentials (TEPs), recorded on EEG data collected simultaneously to TMS delivery originate from GABA(A)-mediated and GABA(B)-mediated inhibitory post synaptic potentials (IPSPs), constituting valuable markers of excitation and inhibition balance and therefore plasticity levels in the brain. TEPs are also reproducible, able to display regional characteristics when TMS is targeting different regions or networks of the brain, and to be sensitive to changes in brain state, and therefore also sensitive to potential improvements in cognitive function. The application of TMS-EEG as a marker of changes in cortical plasticity and reactivity, and therefore response to an rTMS treatment, would help elucidate the mechanisms of action of rTMS in AD patients. Given its spatial and temporal resolution, TMS-EEG can also be used to explore cortical responses to TMS by sampling multiple brain regions and identifying optimal locations where TMS induces strong brain responses and maximal target engagement, to be then used as targets for rTMS treatments.

Stimulating the prefrontal cortex may be the most effective option to improve cognitive functions. Targeting areas such as the right and left DLPFC, Broca and Wernicke, and the right or left parietal somatosensory association cortex while individuals engage in cognitive tasks may also boost the effects of stimulation. However, prominent neuropathological abnormalities in the early stages of the disease (i.e., β-amyloid plaques and neurofibrillary tangles) mostly affect posterior cortical regions of the brain, including, but not limited to, the precuneus, the posterior cingulate, the retrosplenial cortex, and the angular gyri. AD patients also display alterations in medial fronto-parietal functional connectivity and alterations to the so-called Default Mode Network (DMN). The precuneus is a key node of the DMN and in the early clinical stages of AD, functional alterations and reduced connectivity of the Precuneus with the rest of the brain precedes the occurrence of regional brain atrophy, which becomes prominent at later disease stages.

DMN and Precuneus may be viable brain targets for treatment approaches aimed to alleviate dementia symptoms and possibly have disease modifying effects. AD patients show a reduced cortical thickness surrounding the Precuneus, which is often followed by abnormal local activation and hypometabolism, as well as decreased functional connectivity during memory performance. The engagement of DMN and precuneus is also critical for episodic memory retrieval, which is often impaired at the early stages of AD. rTMS over the DMN is capable of enhancing short and long-term memory functions. Therefore, implementing non-invasive brain stimulation interventions targeting the DMN and Precuneus in patients with AD represents a crucial step to slow disease progression and potentially counteract memory decline in AD patients.

However, strategies for maximizing engagement of the DMN-Precuneus (DMN-p) via neurostimulation are not available, and personalized network-level targeting approaches must be developed. The invention described herein provides novel methods to perform non-invasive stimulation of the DMN-p through accurate spatial targeting methods based at least in part on TMS-EEG, as well as solutions for personalization of stimulation intensity, frequency, duration and waveform based at least in part on electrophysiology and neuroimaging data. Results of a double blind, randomized, placebo-controlled, phase-2 clinical trial investigating the impact of rTMS of personalized DMN-p targets defined for each patient on the basis of TMS-EEG data are reported as proof of the effectiveness of the proposed systems and methods for treatment personalization and of the therapeutic protocol itself.

Longer treatment courses could help significantly reducing disease progression in the case of AD. As a non-limiting example, the clinical trial described in the Examples section below documents the impact of the longest rTMS treatment tested in AD patients thus far In some embodiments, the longest rTMS treatment tested in AD patients was 24 weeks.

The methods described herein for brain targeting and treatment of AD also leverage novel insight on AD histopathology and disorders of brain oscillatory activity documented in patients with Dementia, including but not limited to AD, mild cognitive impairment and frontotemporal dementia. In particular, AD is characterized by diffuse amyloid-β (Aβ) plaques and phosphorylated tau (p-tau) deposition in neurofibrillary tangles, as well as widespread neurodegeneration and signs of neuroinflammation. Progressive Aβ deposition can begin up to 20 years before the onset of clinical symptoms and stabilizes around the time that clinical symptoms become prominent. P-tau accumulates particularly in the meso-temporal lobes even in the absence of Aβ, and spreads outside the temporal lobes following multiple trajectories also including, but not limited to, territories part of the DMN. Neurodegeneration and clinical symptoms may be strongly correlated with the spread of p-tau and level of inflammation. Thus, Aβ and p-tau may play a critical role in AD pathogenesis, and interventions that reliably and safely decrease the intracerebral burden of both, Aβ or p-tau, could potentially be of marked clinical importance.

There may be decreased fast oscillatory activity in the "gamma" band, from approximately 30 Hz up to 120 Hz, in patients with AD as well as in mouse models of the disease (5XFAD mouse). This pathological change in gamma activity is linked to parvalbumin+ inhibitory interneurons pathology, with interventions aimed at restoring gamma activity in presymptomatic AD mice showing a remarkable ability to prevent subsequent neurodegeneration and behavioral deficits, as well as a reduction of both Aβ and p-tau. Given its effect on plasticity circuitry and effect on excitability and inhibition levels in the brain, the method described herein for personalized rTMS could also elicit beneficial effects on oscillatory activity in the AD brain, leading to positive clinical, behavioral, cognitive, and neurological outcomes.

Activity within the gamma band is also associated with plasticity processes in the human brain, with gamma-induction interventions via electrical stimulation aimed at boosting gamma oscillatory activity (>30 Hz) increasing cortical plasticity levels during and after stimulation. The combination of rTMS with gamma-inducing protocols may lead to synergistic or additive effects on cortical physiology and plasticity in particular, with a potentially stronger clinical impact on patients as described in some embodiments.

FIG. 1 provides exemplary depictions of embodiments of methods 100 described herein, wherein the methods comprise identifying a personalized target and defining TMS intensity. In some embodiments, with reference to FIG. 1A, a method comprises gathering fMRI data of Alzheimer's Disease (AD) patients 101; creating an average default mode network (DMN) map of AD patients 103, with the center of the map comprising the precuneus 102; focusing on the most connected sub-portion of the precuneus 104; creating a TMS-based functional search 105 via TMS-EEG 106 by measuring TMS-evoked potentials (TEPs) 108 across sub-areas of the precuneus 107, including the most connected sub-portion of the precuneus 104; and creating personalized targets for each brain 109 comprised of original targets 111 and personalized targets 110. In some embodiments, a personalized target is dorsal to the original target. In some embodiments, a personalized target is ventral to the original target. In some embodiments, a personalized target is caudal to the original target. In some embodiments, a personalized target is rostral to the original target. In some embodiments, the personalized target is in the most connected sub-portion of the precuneus 104. In some embodiments, the personalized target is in another sub-area of the precuneus 107. In some embodiments, the method involves, but is not limited to, a two-step procedure to identify DMN network-level targets 103 and then personalize via a TMS-EEG functional search 105. In some embodiments, with reference to FIG. 1B, the method comprises measuring the resting motor threshold (RMT) by measuring action potentials and activity in the index finger 116 while stimulating the precuneus 102; creating a TMS-based functional search via TMS-EEG 106 by measuring TMS-evoked potentials (TEPs) 117 across sub-areas of the precuneus 107, including the most connected sub-portion of the precuneus 104; and determining the personalized stimulation intensity 118. In some embodiments, the resting motor threshold 116 is used as a measure of cortical excitability. In some embodiments, the RMT at which neural impulses are found 116 can be used to determine a patient's personalized RMT as a percentage. In some embodiments, the TEPs 117 can be used to measure amplitude, delay, shape, or frequency of a response to TMS-EEG. In some embodiments, after measuring TEPs 117, a patient's personalized RMT can be adjusted to a different or same percentage 118. In some embodiments, after measuring TEPs 117, a patient's personalized stimulation frequency can be measured 118. In some embodiments, this method can be used to personalize stimulation intensity to a patient. In some embodiments, with reference to FIG. 1C, the method comprises positioning a TMS coil 119, generating biophysical modeling results 120, and using one biophysical modeling result 121 to estimate the induced electric field on a target region 122. In some embodiments, the biophysical modeling results use an electric field norm map measured in volts per meter (V/m). In some embodiments, the desired minimal induced electric field value is the estimated induced electric field 122 plus 27%. In some embodiments, the adjusted TMS stimulation to induce an electrical field is a percentage equal to the desired minimal induced electric field value. In some embodiments, with reference to FIG. 1D, the method comprises various alternative targets for the DMN, as well as for other functional brain networks relevant for AD, including but not limited to the prefrontal node of the default mode network 112, the fronto-parietal control network 113, the dorsal attention network 114, or the sensorimotor network 115. In some embodiments, the methods described herein can be applied to alternative targets for DMN.

Figure 2B:
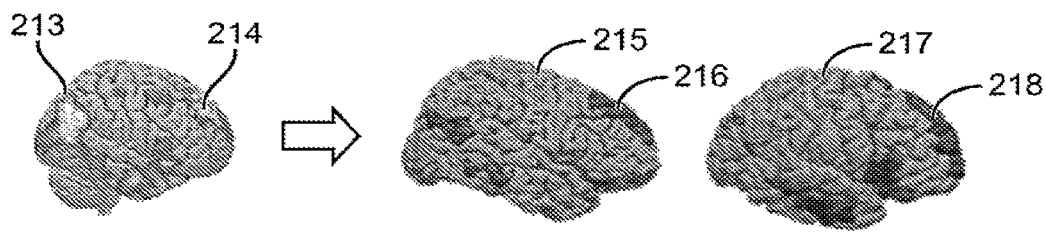
Figure 2C:
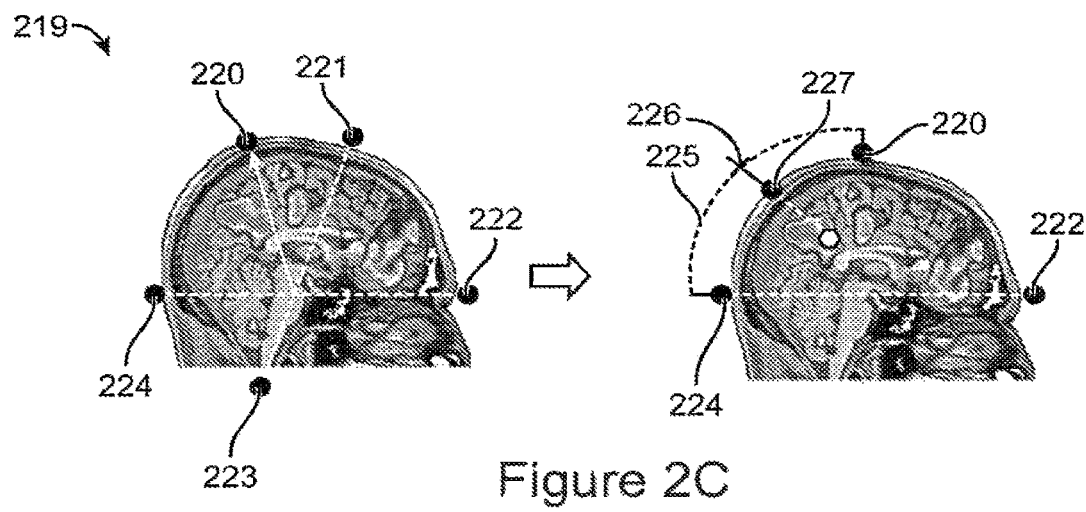

FIG. 2 provides exemplary methods for target identification 200 using normative and custom brain activity templates. In some embodiments, these methods can be used in the absence of specific brain scans. In some embodiments, with reference to FIG. 2A, the method comprises a functional networks atlas 201 comprising the visual network 212, the default mode network 209, the frontoparietal network 206, the limbic network 210, the ventral attention network 211, the somatosensory network 208, and the dorsal attention network 207; which can be adapted for patients 202, 203, 204, or 205. In some embodiments, the method comprises adapting existing anatomical atlases. In some embodiments, the method comprises adapting existing functional atlases. In some embodiments, the networks of the brain are shaped differently in different patients. In some embodiments, with reference to FIG. 2B, the method comprises morphing pre-defined brain activated patterns into individual patient anatomy by measuring brain activation 214 during episodic memory processing in AD patients 213 and adapting the patterns to activated areas to brain activation 216 in patient brain 215 and activation 218 in patient brain 217. In some embodiments, the activated areas 216 and 218 are same. In some embodiments, the activated areas 216 and 218 are different. In some embodiments, pre-defined brain activation patterns are similar to individual patient anatomy. In some embodiments, pre-defined brain activation patterns are different from individual patient anatomy. In some embodiments, with reference to FIG. 2C, the method comprises using scalp coordinates 219 comprising the vertex 220, the left tragus 221, the nasion 222, the right tragus 223, and the inion 224; and locating the optimal target distance 226 based on the Inion-Vertex distance 225 to find the optimal first stimulation location on the scalp 227. In some embodiments, the optimal target distance 226 is the optimal first stimulation location based on scalp coordinates. In some embodiments, the optimal target distance 226 is 29% of the Inion-Vertex distance 225 from the vertex 220.

Figure 3:
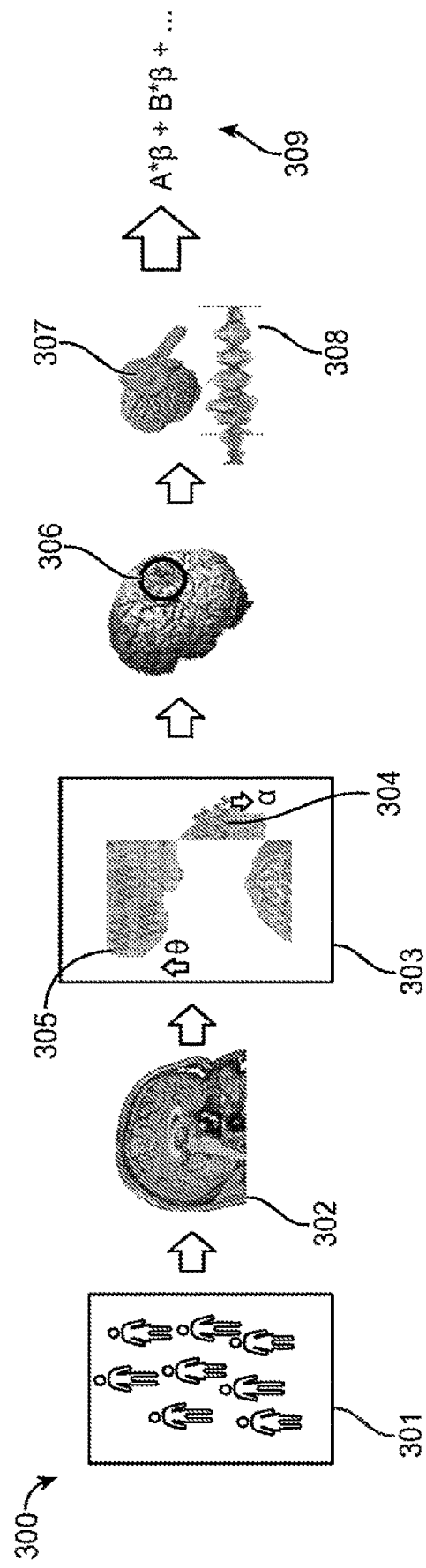
FIG. 3 provides an exemplary method for generating a prediction model for estimating stimulation parameters, according to an embodiment herein.

FIG. 3 provides an exemplary method for generating a prediction model for stimulation parameters 300. In some embodiments, the method comprises using a normative AD patients data set 301, a structural brain scan 302 including but not limited to scalp-cortex distance, measuring cortical excitability from the primary motor cortex 303 comprised of theta waves 305 and alpha waves 304, measuring induced electric fields in the precuneus 306, measuring stimulation intensity 308 for the precuneus via TMS-EEG Opti-Stim procedure 307, and creating a prediction model for stimulation parameters estimation 309. In some embodiments, the normative AD patients dataset is a small dataset. In some embodiments, the normative AD patients dataset is a large dataset. In some embodiments, the corticospinal excitability is measured as altered neural oscillations. In some embodiments, the altered neural oscillations include, but are not limited to, increased frequency of theta waves. In some embodiments, the altered neural oscillations include, but are not limited to, decreased frequency of alpha waves.

FIG. 4 provides exemplary methods of subcortical targeting 400 via functional and structural connectome data. In some embodiments, with reference to FIG. 4A, the method comprises using an MRI 401 to measure episodic memory activation 402 of the brain to show activated areas 404 in a resting state functional MRI (rs-fMRI) 403. In some embodiments, the episodic memory activation 402 is recorded during a memory task in a task-fMRI. In some embodiments, the target network activated 404 is the DMN. In some embodiments, the method for identifying patient-specific brain activation during a memory task in a patient with Alzheimer's disease highlights involvement of the DMN. In some embodiments, with reference to FIG. 4B, the method comprises MRI data of the hippocampus 405, parahippocampus 406, and left angular gyrus 407, and white matter tractography data 408. In some embodiments, the method identifies optical cortical targets for hippocampus modulation using structural MRI data. In some embodiments, the method identifies optical cortical targets for hippocampus modulation using diffusion MRI data. In some embodiments, the method uses MRI data to calculate and visualize white matter fiber tracts 408 connecting a stimulated superficial area (e.g., angular gyrus) with subcortical targets of interest for AD (e.g., the hippocampus for its role in memory processing). In some embodiments, white matter fibers may be estimated from multiple sub-regions of the angular gyrus, with the subregion displaying the strongest white matter fiber pathway towards the hippocampus selected as the final personalization target. In some embodiments, with reference to FIG. 4C, the method comprises using biophysical modeling of the brain 409 to estimate the optimal intensity to activate the angular gyrus and hippocampus 410 via TMS 411. In some embodiments, biophysical modeling 409 is E-field modeling. In some embodiments, the biophysical modeling 409 is used to estimate the induced electric field in the angular gyrus of an AD patient, then used to optimize stimulation parameters, including but not limited to stimulation intensity.

Figure 5:
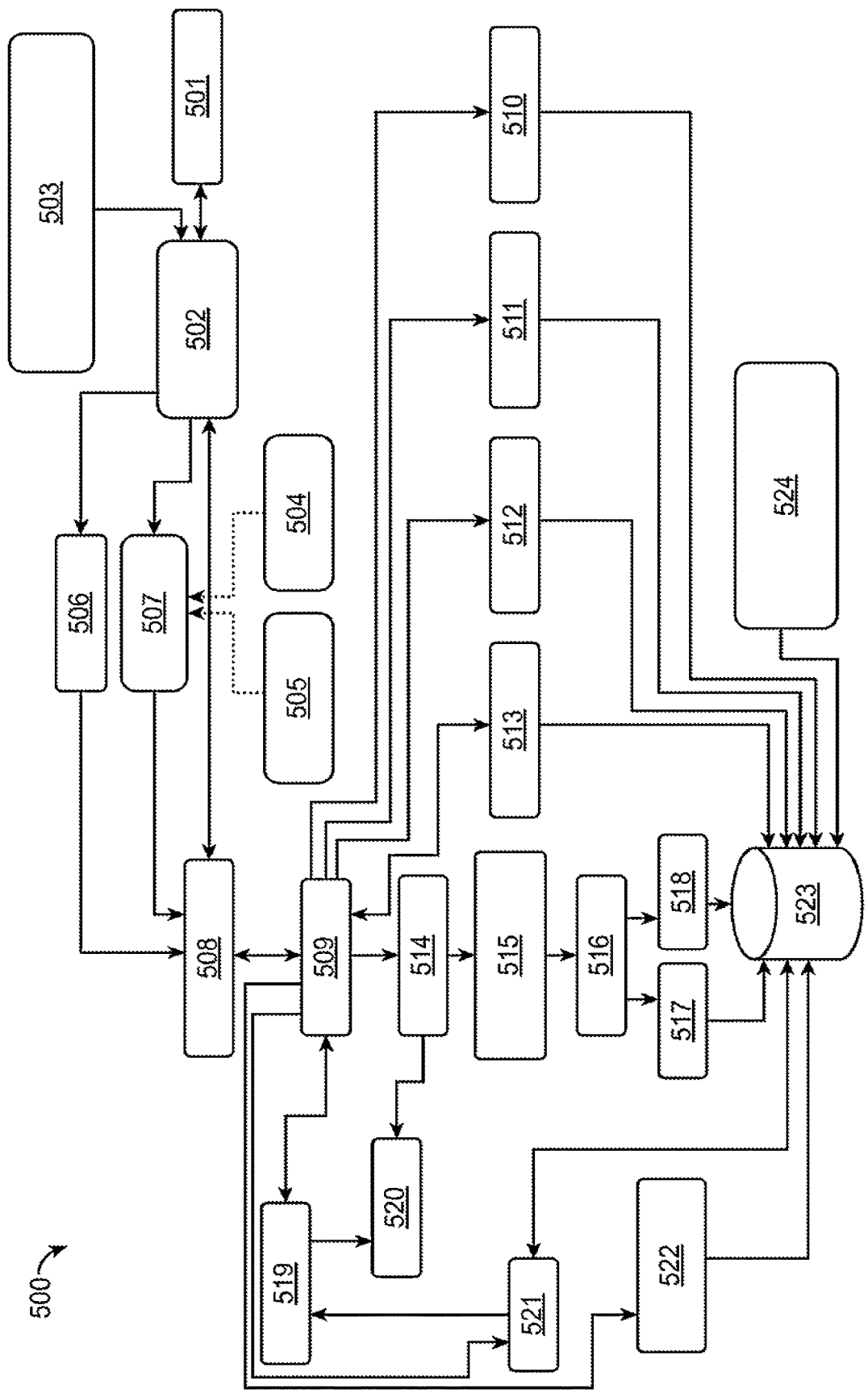
FIG. 5 provides an exemplary flow chart depicting a method for treating a medical condition according to an embodiment described herein.

FIG. 5 provides an exemplary flowchart 500 of the infrastructure of an apparatus for treatment optimization and delivery. In some embodiments, the flowchart comprises clinical staff member or user 503, a web browser or local machine 502, authentication 501, brain scan data 504, TMS session data 505, EEG pairing 506, survey metadata 507, gateway ingress 508, gateway 509, notification 510, billing 511, schedule 512, object 513, collection 514, cleaning or preprocessing 515, featurization 516, generation of models 517 and 518, streamer 519, storage 520, export 521, baseline survey 522, database 523, and population-based inference for treatment optimization 524. In some embodiments, TMS session data 505 and brain scan data 504 is inputted into survey metadata 507. In some embodiments, a clinical staff member 503 uses the web browser or local machine 502 and authenticates 501 the staff member as a user. In some embodiments, the there is a set of main actions from the gateway, including, but not limited to: streaming 519—the ability to query and stream data (for instance, EEG time series data); data collection 514—the ability to collect, clean, featurize, and process raw EEG data, for example, with the intent to take in an EEG feed and get back a location in the brain to stimulate; object 513—the ability to access and query the database; scheduling 512—the ability to book and post a patient schedule or appointment; billing 511—the ability to access billing information and charge per session with a third-party service provider; notifications 510—the ability to send emails to users upon certain actions being completed (e.g., a session being completed or billing successful, or targeting results being ready); data export 521—the ability to request and create data bundles or downloads from information in the database; baseline users 522—the ability to baseline users through a survey instrument such as, but not limited to, a digitized Mini-Mental State Exam (MMSE), or post information from the electronic health record (HER) into the survey itself. In some embodiments, collection 514 includes cleaning or preprocessing 515, featurization 516, and creation of multiple models 517 and 518. In some embodiments, all information in the infrastructure is collected in the database 523, which then creates population-based inferences for treatment optimization 524. In some embodiments, population-based inferences for treatment optimization 524 comprise the results of one or more sessions of one patient. In some embodiments, population-based inferences for treatment optimization 524 comprise the results of one or more sessions of multiple patients.

FIG. 6 provides an exemplary depiction of a study design and results 600. In some embodiments, with reference to FIG. 6A, the study design 601 comprised a clinical evaluation at week 0 comprised of testing including but not limited to Clinical Dementia Rating (CDR), Alzheimer's Disease Assessment Scale-Cognitive Subscale (ADAS-Cog), Mini Mental State Examination (MMSE), Neuropsychiatric Inventory (NPI), Alzheimer's Disease Cooperative Study-Activities of Daily Living Scale (ADCS-ADL) or Frontal Assessment Battery (FAB); a neurophysiological evaluation at week 0 including but not limited to TMS-EEG, long-term potentiation (LTP), and short-latency afferent inhibition (SAI); an intensive phase comprised of real or sham rTMS in 10 daily sessions for two weeks; a maintenance phase comprised of real or sham rTMS in 22 weekly sessions for 22 weeks; a clinical evaluation at week 12 comprising testing including but not limited to CDR, ADAS-Cog, FAB, MMSE, NPI, or ADCS-ADL; a clinical evaluation at week 24 comprised of testing including but not limited to CDR, ADAS-Cog, FAB, MMSE, NPI, or ADCS-ADL; and a neurophysiological evaluation at week 24 including but not limited to TMS-EEG, LTP, and SAI. In some embodiments, with reference to FIG. 6B, results of the study design 602 comprised an average location of the TMS coil on a scalp across patients visualized on a template head, and biophysical modeling results based on a simulated induced electric field. In some embodiments, the average location of the TMS coil on the scalp was above the precuneus. In some embodiments, biophysical modeling was E-field modeling. In some embodiments, the biophysical modeling was generated using precuneus rTMS. In some embodiments, additional imaging techniques, for example, MRI, can be used to show the average stimulation location. In some embodiments, with reference to FIG. 6C, results of the study design 603 comprised TMS-EEG data mapped across time, space, and frequency at target locations for one or more patients. In some embodiments, the TMS-EEG data was measured for 300 milliseconds (ms). In some embodiments, the map across time was measured in microVolts per millisecond. In some embodiments, the map cross frequency was measured in Hertz per millisecond. In some embodiments, TMS-EEG data collection was concurrent across patients. In some embodiments TMS-EEG data collection was performed at baseline to personalized rTMS intensity and target location for each patient. In some embodiments, TMS-EEG data collection was repeated at the end of the trial to look at longitudinal changes in brain reactivity after treatment.

Figure 8B:
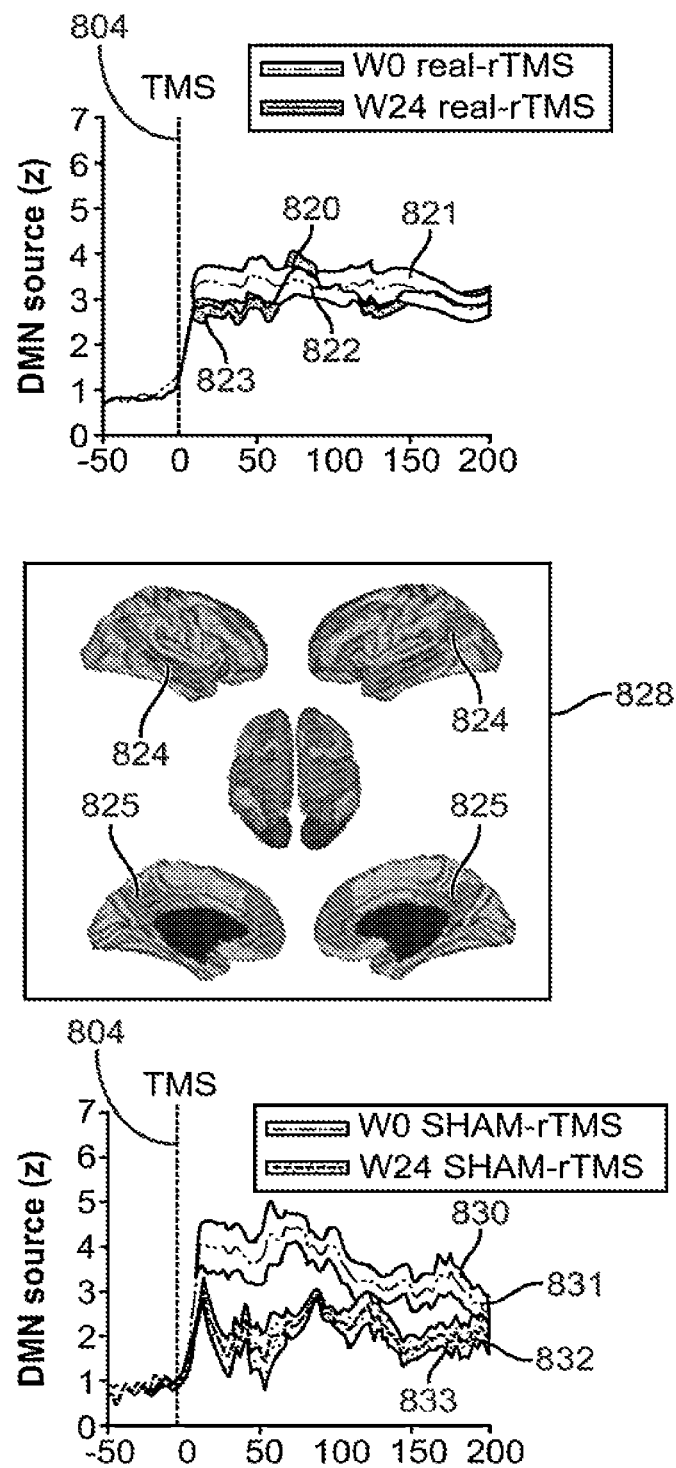

FIG. 7 provides an exemplary depiction of cognitive changes 700 after treatment according to an embodiment herein. In some embodiments, baseline was plotted at week zero, which is the mean assessment time of the baseline measurement as offset from the first dose of trial agent. In some embodiments, error bars indicated standard errors. In some embodiments, with reference to FIG. 7A, the depiction of cognitive changes comprised a graph of generalized linear mixed model (GLMM) estimated mean change across three time points spanning 24 weeks, comprised of a rTMS line 701 and a sham-rTMS line 702. In some embodiments, the graph showed the GLMM estimated mean change from baseline on the Clinical Dementia Rating scale Sum of Boxes (CDR-SB). In some embodiments, scores range was obtained by summing each of the domain box scores, with scores ranging from 0 to 18. In some embodiments, higher scores indicated worse cognition. In some embodiments, the three time points were at week zero, week 12, and week 24. In some embodiments, asterisks comprised vertical and horizontal averages of the rTMS and sham-rTMS lines. In some embodiments, with reference to FIG. 7B, the depiction of cognitive changes comprised a graph of GLMM estimated mean change across three time points spanning 24 weeks, comprised of a rTMS line 701 and a sham-rTMS line 702. In some embodiments, the graph showed the GLMM estimated mean change from baseline on the Alzheimer's Disease Assessment Scale-Cognitive 11-item scale (ADAS-Cog11). In some embodiments, scores ranged from 0 to 70. In some embodiments, higher scores indicated worse cognition. In some embodiments, the three time points were at week zero, week 12, and week 24. In some embodiments, asterisks comprised vertical and horizontal averages of the rTMS and sham-rTMS lines. In some embodiments, with reference to FIG. 7C, the depiction of cognitive changes comprised a graph of GLMM estimated mean change across three time points spanning 24 weeks, comprised of a rTMS line 701 and a sham-rTMS line 702. In some embodiments, the graph showed the GLMM estimated mean change from baseline on the MMSE scale. In some embodiments, scores ranged from 0 to 30. In some embodiments, lower scores indicated worse cognition. In some embodiments, the three time points were at week zero, week 12, and week 24. In some embodiments, asterisks comprised vertical and horizontal averages of the rTMS and sham-rTMS lines. In some embodiments, with reference to FIG. 7D, the depiction of cognitive changes comprised a graph of GLMM estimated mean change across three time points spanning 24 weeks, comprised of a rTMS line 701 and a sham-rTMS line 702. In some embodiments, the graph showed the GLMM estimated mean change from baseline on the Alzheimer's Disease Cooperative Study Activities of Daily Living (ADCS-ADL) scale. In some embodiments, scores ranged from 0 to 78. In some embodiments, lower scores indicated worse function. In some embodiments, the three time points are at week zero, week 12, and week 24. In some embodiments, with reference to FIG. 7E, the depiction of cognitive changes comprised a graph of GLMM estimated mean change across three time points spanning 24 weeks, comprised of a rTMS line 701 and a sham-rTMS line 702. In some embodiments, the graph showed the GLMM estimated mean change from baseline on the NPI scale. In some embodiments, scores ranged from 0 to 144. In some embodiments, higher scores indicated worse behavioral symptoms. In some embodiments, the three time points were at week zero, week 12, and week 24. In some embodiments, with reference to FIG. 7F, the depiction of cognitive changes comprised a graph of GLMM estimated mean change across three time points spanning 24 weeks, comprised of a rTMS line 701 and a sham-rTMS line 702. In some embodiments, the graph showed the GLMM estimated mean change from baseline on the Frontal Assessment Battery (FAB) scale. In some embodiments, scores ranged from 0 to 18. In some embodiments, higher scores indicated better frontal cognitive functions. In some embodiments, the three time points were at week zero, week 12, and week 24. In some embodiments, asterisks comprised vertical and horizontal averages of the rTMS and sham-rTMS lines FIG. 8 provides an exemplary depiction of TMS-EEG results 800 after treatment according to an embodiment herein. In some embodiments, with reference to FIG. 8A, TMS-EEG results comprised a graph of TMS-evoked potentials (TEPs) with error bars 801, real-rTMS at week zero line 803, real-rTMS at week 24 line 802, TMS pulse 804, and DMN-p response activity intervals 809; DMN-p response activity at week 0 in the first interval 805, DMN-p response activity at week 0 in the second interval 807, DMN-p response activity at week 24 in the first interval 806, DMN-p response activity at week 24 in the first interval 808; a graph of TEPs of sham-rTMS at week zero line 811 with error bars 810, sham-rTMS at week 24 line 813 with error bars 812, TMS pulse 804, and DMN-p response activity intervals 819; and DMN-p response activity at week 0 in the first interval 815, DMN DMN-p response activity at week 0 in the second interval 817, DMN-p response activity at week 24 in the first interval 816, and DMN-p response activity at week 24 in the first interval 818. In some embodiments, TEPs were measured in microVolts. In some embodiments, the x-axis of the TEP graphs was in milliseconds. In some embodiments, sham-rTMS was any approach that aims to mimic the effects of real-rTMS without actual stimulation of the brain. In some embodiments, TEPs were collected from the DMN-p stimulation before (week zero) and after 24 weeks of real or sham-rTMS over the DMN-p. In some embodiments, after 24 weeks, TEPs evoked from single-pulse TMS of the DMN-p decreased in amplitude for sham-rTMS patients. In some embodiments, after 24 weeks, TEPs evoked from single-pulse TMS of the DMN-p did not change in amplitude for real-rTMS patients. In some embodiments, with reference to FIG. 8B, TMS-EEG results comprised a graph of the DMN source activity of real-rTMS at week zero line 822 with error bars 821, real-rTMS at week 24 line 820 with error bars 823, and TMS pulse 804; source reconstruction 828 over the DMN at week zero 824 and at week 24 825; and a graph of the DMN source activity of sham-rTMS at week zero line 831 with error bars 830, sham-rTMS at week 24 line 832 with error bars 833, and TMS pulse 804. In some embodiments, sham-rTMS was any approach that aims to mimic the effects of real-rTMS without actual stimulation of the brain. In some embodiments, after 24 weeks, DMN source activity evoked from single-pulse TMS of the DMN-p decreased in amplitude for sham-rTMS patients. In some embodiments, after 24 weeks, DMN source activity evoked from single-pulse TMS of the DMN-p did not change in amplitude for real-rTMS patients.

Figure 9:
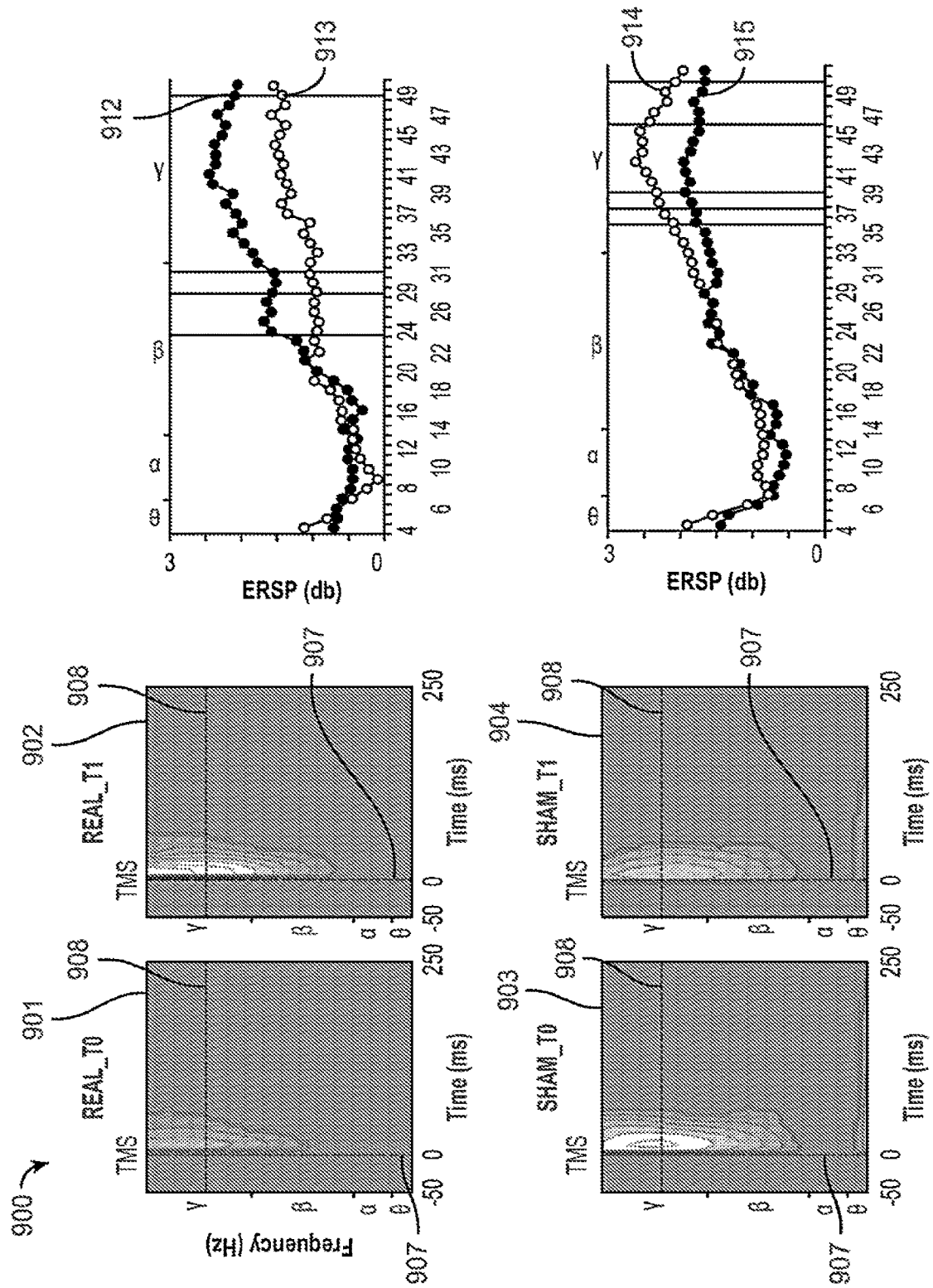
FIG. 9 provides an exemplary depiction of changes in brain activity after treatment according to an embodiment herein.
Figure 9:
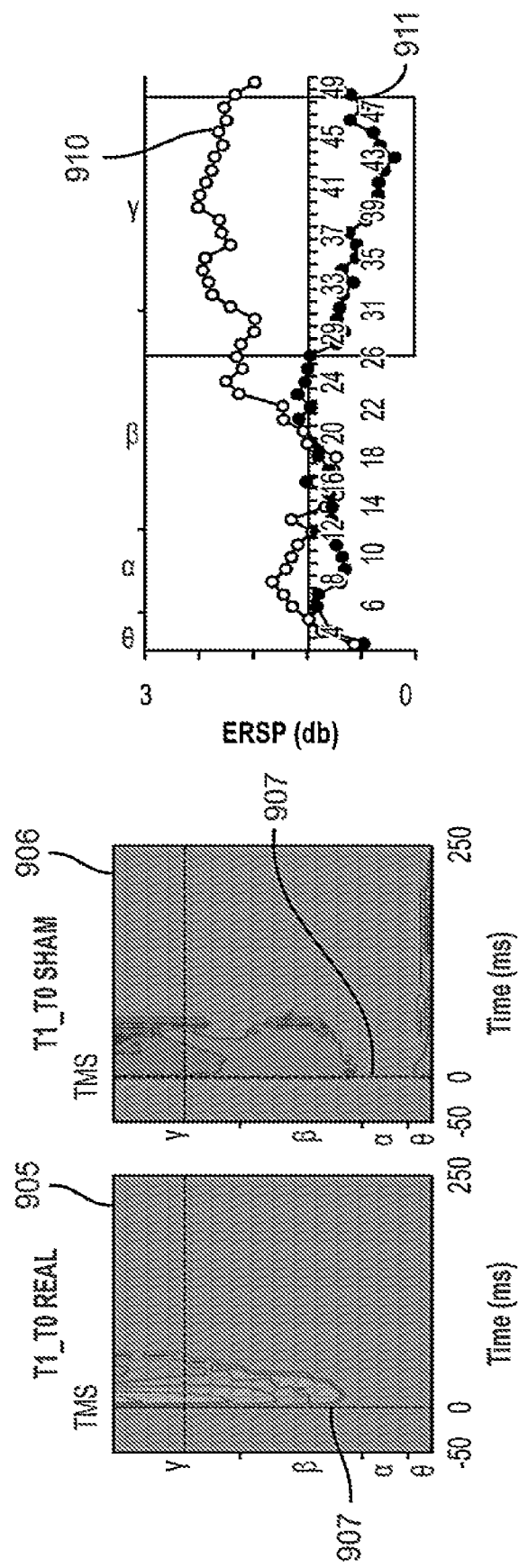

FIG. 9 provides an exemplary depiction of changes in brain oscillatory activity in the gamma band 900 after treatment according to an embodiment herein. In some embodiments, the depiction comprised TMS-related spectral perturbation (TRSP) after single-pulse TMS 907 of the DMN-p in patients who underwent real-rTMS at time zero 901 and time one 902, wherein time one is after stimulation and time zero is before stimulation, with difference 905; TRSP after single-pulse TMS 907 of the DMN-p in patients who underwent sham-rTMS at time zero 903 and time one 904, wherein time one is after stimulation and time zero is before stimulation, with difference 906, wherein horizontal line 908 across from letter gamma on the y-axis is a natural gamma frequency of 40 Hz; and graphs of event-related spectral dynamics (ERSP) comprised of post real-rTMS 912, baseline real-rTMS 913, post sham-rTMS 914, baseline sham-rTMS 915, difference between post and baseline real-rTMS 910, and difference between post and baseline sham-rTMS 911. In some embodiments, ERSP was measured in spectral power (db). In some embodiments, the shaded boxes in the ERSP graphs showed differences between lines on any given graph. In some embodiments, TRSP was measured in Hertz per millisecond. In some embodiments, the y-axes of the TRSP graphs showed the ranges of gamma, beta, alpha, and theta waves. In some embodiments, there was an increase in oscillatory activity specifically in the beta and gamma frequency bands after real-rTMS and a slight decrease after sham-rTMS. In some embodiments, there was a difference between the gamma spectral power of real-rTMS and sham-rTMS when directly compared against one another. In some embodiments, change in TRSP graph for real-rTMS 905 showed an increase in activity. In some embodiments, change in TRSP graph for sham-rTMS 906 showed a decrease in activity. In some embodiments, the difference between real and sham-rTMS in an ERSP graph was positive.

FIGS. 10-14 provide an exemplary TMS study protocol, study conditions, and study results. FIGS. 10A-10D provide an exemplary TMS study protocol and study conditions 1000 according to an embodiment herein, wherein various measured results are provided. In some embodiments, the study protocol comprised brain wave graph 1001 comprised of responses to gamma transcranial Alternating Current Stimulation (γtACS) 1003, theta transcranial Alternating Current Stimulation (θtACS) 1004, and intermittent theta burst stimulation (iTBS) 1002 (FIG. 10A); depictions of stimulation of a chosen brain area 1005 with a tACS instrument 1006 (FIG. 10B); depictions of brain areas for stimulation comprising the left dorsolateral prefrontal cortex (DLPFC SX) 1009, the right dorsolateral prefrontal cortex (DLPFC DX) 1008, or the vertex 1007, or any combination thereof (FIG. 10C); and an experimental protocol comprised of TMS-EEG before stimulation at T0 1015, iTBS-tACS stimulation 1016, TMS-EEG immediately after stimulation at T1 1017, and TMS-EEG 20 minutes after stimulation at T2 1018 (FIG. 10D). In some embodiments, the brain wave graph 1001 showed brain waves in Hertz per second. In some embodiments, θtACS was done at 5 Hz. In some embodiments, γtACS was done at 70 Hz.

Figure 11:
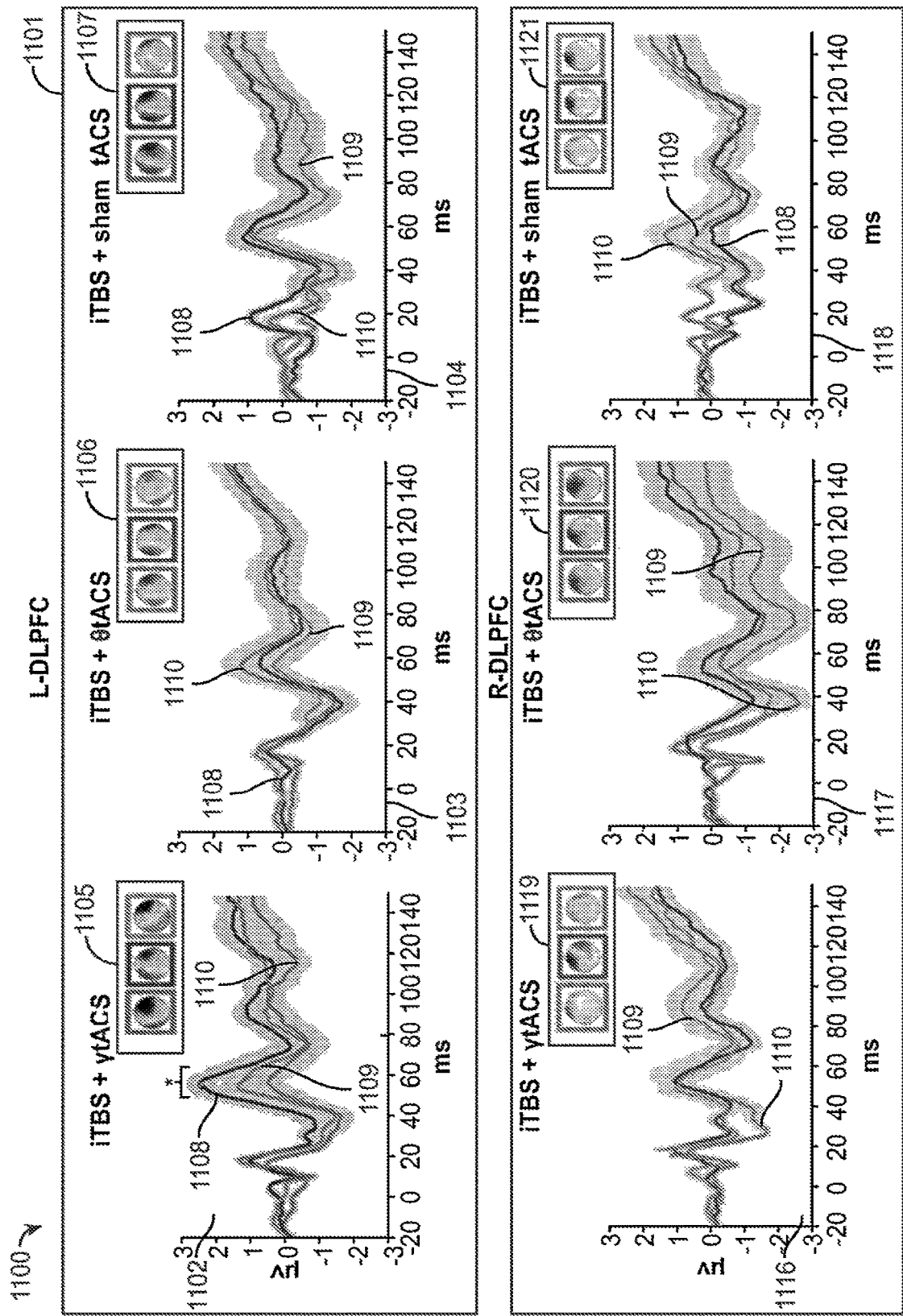
FIG. 11 provides an exemplary depiction of changes in brain activity in certain brain regions after treatment according to an embodiment herein.
Figure 11:
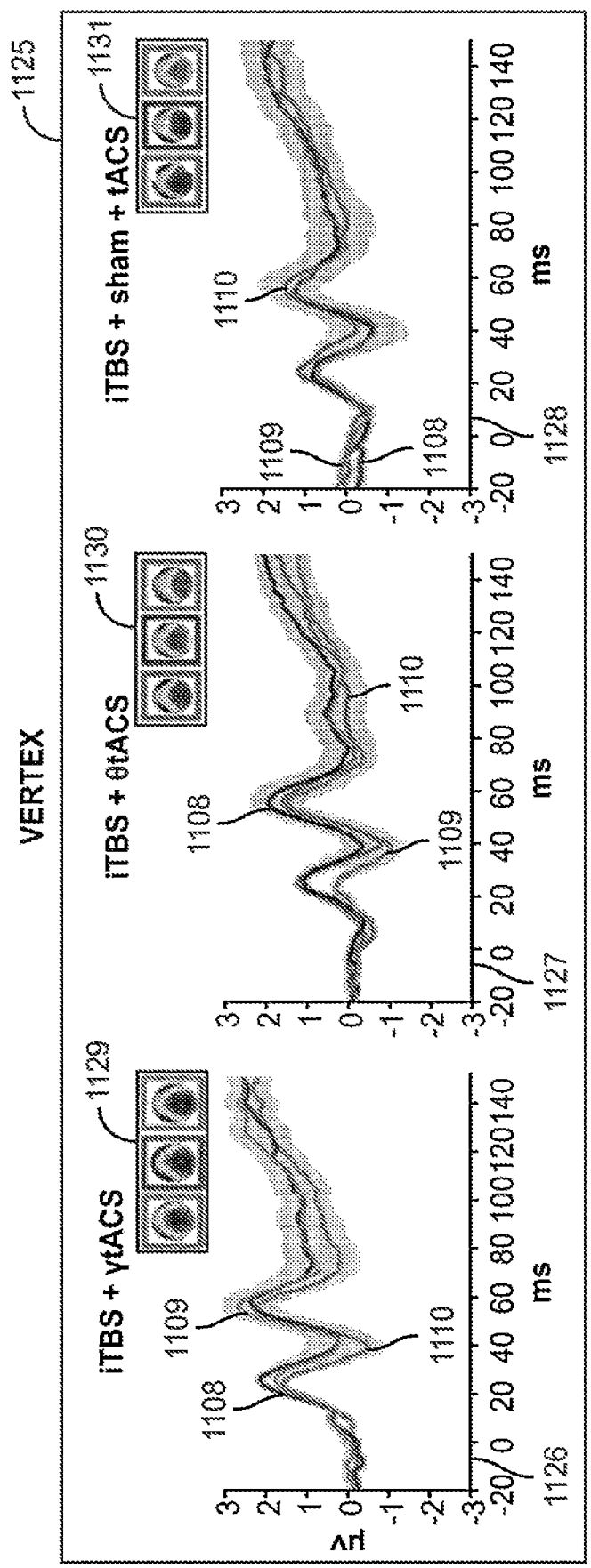

FIG. 11 provides an exemplary depiction of changes in brain activity 1100 in certain brain regions after treatment according to protocol 1000. In some embodiments, the changes in brain activity comprised changes to the left DLPFC 1101, comprised of graphs of TEPs after a single pulse TMS perturbation when iTBS and γtACS stimulation was used together 1102 with spectral power representation 1105, with graphical representations of TEPs at T0 1110, T1 1108, and T2 1109; graphs of TEPs after a single pulse TMS perturbation when iTBS and θtACS stimulation was used together 1103 with spectral power representation 1106, with graphical representations of TEPs at T0 1110, T1 1108, and T2 1109; and graphs of TEPs after a single pulse TMS perturbation when iTBS and sham tACS stimulation was used together 1104 with spectral power representation 1107, with graphical representations of TEPs at T0 1110, T1 1108, and T2 1109. In some embodiments, the changes in brain activity comprised changes to the right DLPFC 1115, comprised of graphs of TEPs after a single pulse TMS perturbation when iTBS and γtACS stimulation was used together 1116 with spectral power representation 1119, with graphical representations of TEPs at T0 1110, T1 1108, and T2 1109; graphs of TEPs after a single pulse TMS perturbation when iTBS and θtACS stimulation was used together 1117 with spectral power representation 1120, with graphical representations of TEPs at T0 1110, T1 1108, and T2 1109; and graphs of TEPs after a single pulse TMS perturbation when iTBS and sham tACS stimulation was used together 1118 with spectral power representation 1121, with graphical representations of TEPs at T0 1110, T1 1108, and T2 1109. In some embodiments, the changes in brain activity comprised changes to the vertex 1125, comprised of graphs of TEPs after a single pulse TMS perturbation when iTBS and γtACS stimulation was used together 1126 with spectral power representation 1129, with graphical representations of TEPs at T0 1110, T1 1108, and T2 1109; graphs of TEPs after a single pulse TMS perturbation when iTBS and θtACS stimulation was used together 1127 with spectral power representation 1130, with graphical representations of TEPs at T0 1110, T1 1108, and T2 1109; and graphs of TEPs after a single pulse TMS perturbation when iTBS and sham tACS stimulation was used together 1128 with spectral power representation 1131, with graphical representations of TEPs at T0 1110, T1 1108, and T2 1109. In some embodiments, θtACS was done at 5 Hz. In some embodiments, γtACS was done at 70 Hz. In some embodiments, there was an increase in the amplitude of TEPs after single pulse TMS perturbation for iTBS plus γtACS compared to iTBS plus θtACS or iTBS plus sham tACS. In some embodiments, the increase was present for the left DLPFC but not for the right DLPFC or the vertex.

Figure 12:
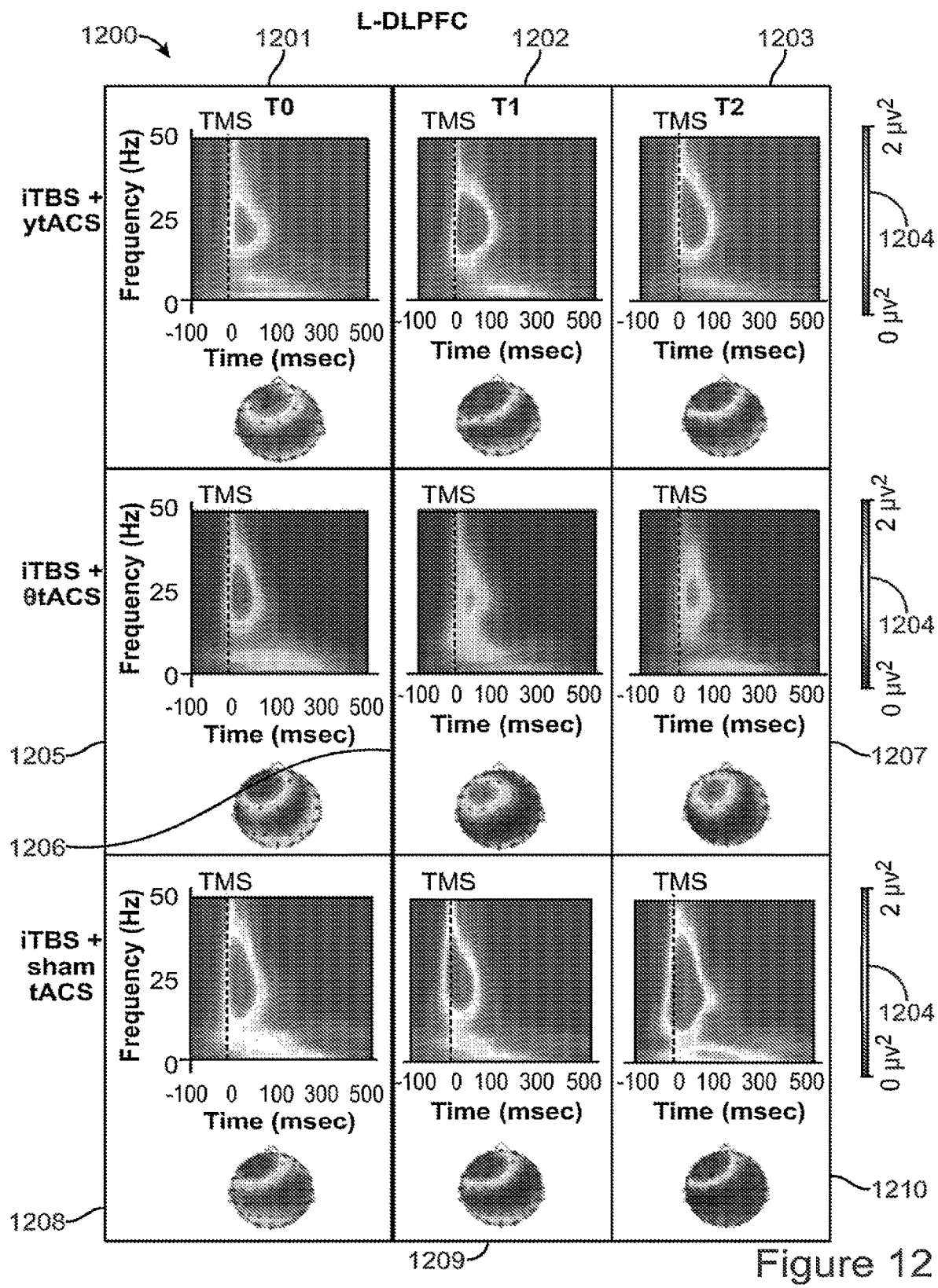
FIG. 12 provides an exemplary depiction of changes in brain activity in certain brain regions after treatment according to an embodiment herein.
Figure 12:
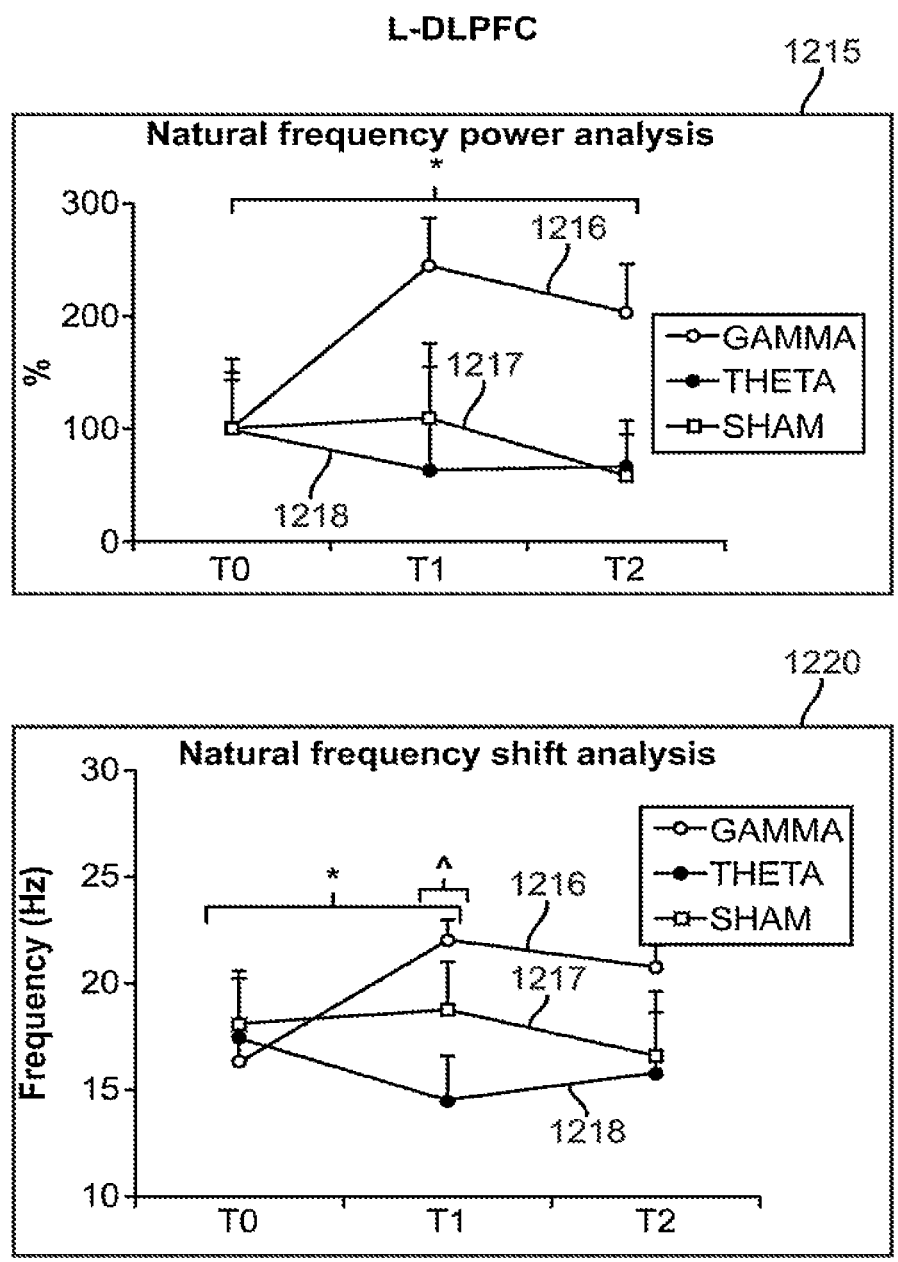

FIG. 12 provides an exemplary depiction of changes in brain activity in the left DLPFC 1200 in certain brain regions after treatment according to protocol 1000. In some embodiments, the changes in brain activity comprised spectral perturbation images, comprised of iTBS plus γtACS at T0 1201, T1 1202, and T2 1203 with shading scale 1204; iTBS plus θtACS at T0 1205, T1 1206, and T2 1207 with shading scale 1204; iTBS plus sham tACS at T0 1208, T1 1209, and T2 1210 with shading scale 1204; a natural frequency power analysis graph 1215 with iTBS plus γtACS line 1216, iTBS plus θtACS line 1218, and iTBS plus sham tACS line 1217; and a natural frequency shift analysis graph 1220 with iTBS plus γtACS line 1216, iTBS plus θtACS line 1218, and iTBS plus sham tACS line 1217. In some embodiments, spectral perturbation graphs measured frequency in Hertz per millisecond. In some embodiments, shading scale 1204 ranged from 0 microVolts squared ($\mu V^2$) to 2 $\mu V^2$. In some embodiments, the natural frequency power analysis 1215 measured percent change at T0, T1, and T2. In some embodiments, the natural frequency shift analysis 1220 measured frequency change at T0, T1, and T2. In some embodiments, θtACS was done at 5 Hz. In some embodiments, γtACS was done at 70 Hz. In some embodiments, the effect of iTBS plus γtACS was visible in spectral perturbation and oscillatory activity. In some embodiments, iTBS plus γtACS increased the spectral power of local response in the gamma band, compared to no visible effect for iTBS plus θtACS or iTBS plus sham tACS.

Figure 13:
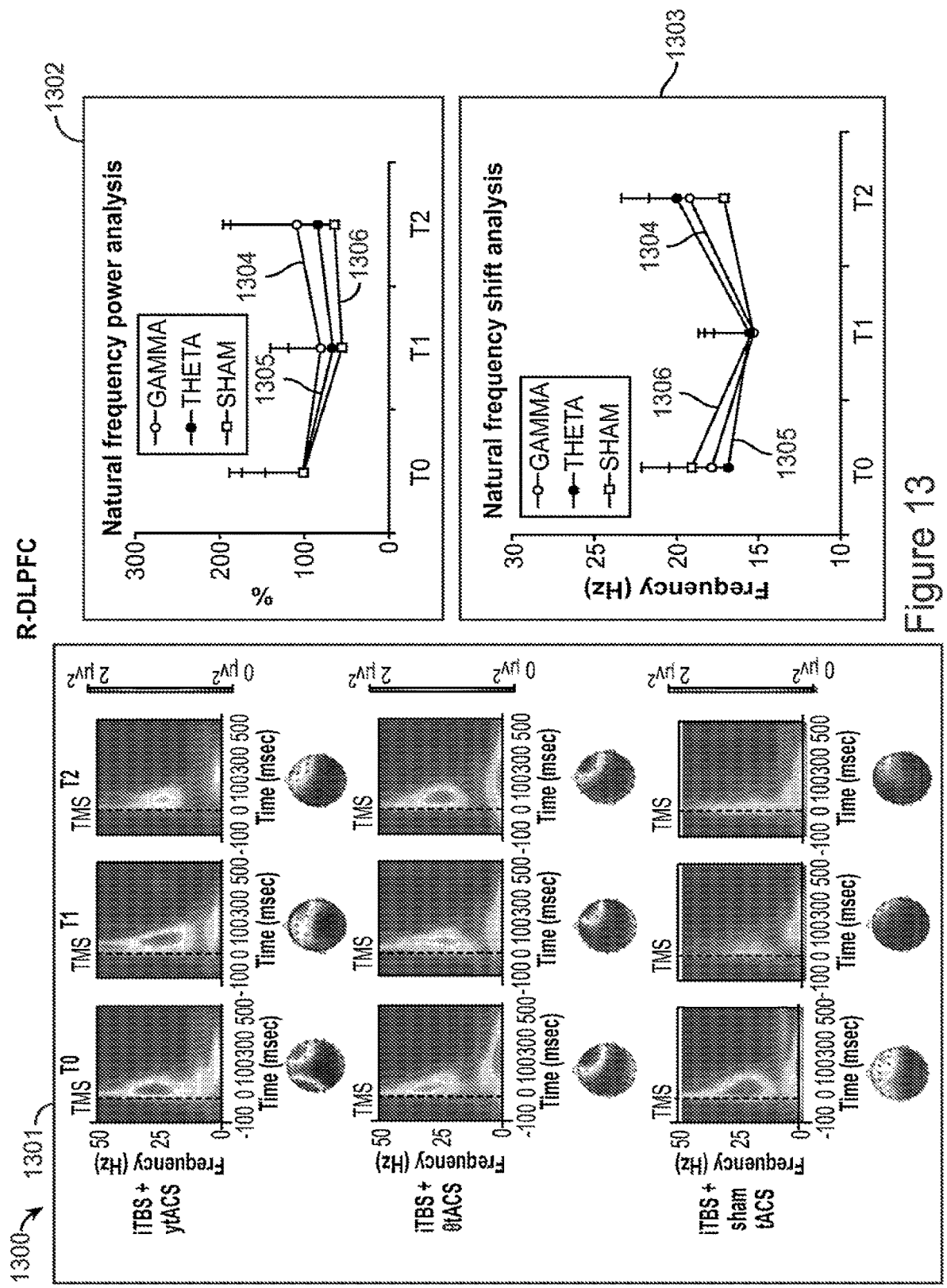
FIG. 13 provides an exemplary depiction of a lack of change in brain activity in certain brain regions after treatment according to an embodiment herein.

FIG. 13 provides an exemplary depiction of a lack of change in brain activity in the right DLPFC 1300 after treatment according to protocol 1000. In some embodiments, the changes in brain activity comprised spectral perturbation images 1301, comprised of iTBS plus γtACS at T0, T1, and T2; iTBS plus θtACS at T0, T1, and T2; iTBS plus sham tACS at T0, T1, and T2; a natural frequency power analysis graph 1302 with iTBS plus γtACS line 1304, iTBS plus θtACS line 1305, and iTBS plus sham tACS line 1306; and a natural frequency shift analysis graph 1303 with iTBS plus γtACS line 1304, iTBS plus θtACS line 1305, and iTBS plus sham tACS line 1306. In some embodiments, spectral perturbation graphs measured frequency in Hertz per millisecond. In some embodiments, a shading scale ranged from 0 microVolts squared ($\mu V^2$) to 2 $\mu V^2$. In some embodiments, the natural frequency power analysis 1302 measured percent change at T0, T1, and T2. In some embodiments, the natural frequency shift analysis 1303 measured frequency change at T0, T1, and T2. In some embodiments, θtACS was done at 5 Hz. In some embodiments, γtACS was done at 70 Hz. In some embodiments, there were no visible changes in spectral power over the right DLPFC.

Figure 14:
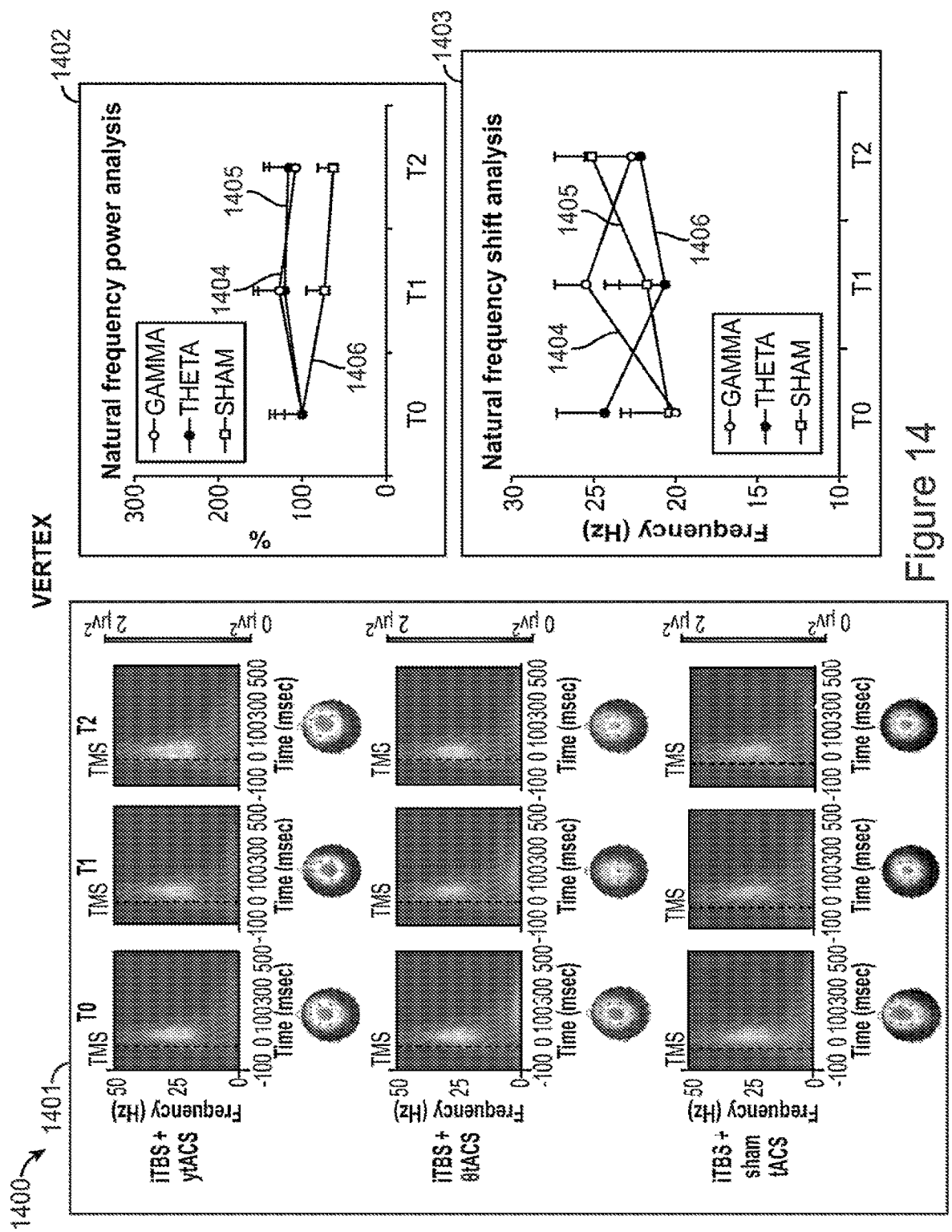
FIG. 14 provides an exemplary depiction of a lack of change in brain activity in certain brain regions after treatment according to an embodiment herein.

FIG. 14 provides an exemplary depiction of a lack of change in brain activity in the vertex 1400 after treatment according to protocol 1000. In some embodiments, the changes in brain activity comprised spectral perturbation images 1401, comprised of iTBS plus γtACS at T0, T1, and T2; iTBS plus θtACS at T0, T1, and T2; iTBS plus sham tACS at T0, T1, and T2; a natural frequency power analysis graph 1402 with iTBS plus γtACS line 1404, iTBS plus θtACS line 1406, and iTBS plus sham tACS line 1405; and a natural frequency shift analysis graph 1403 with iTBS plus γtACS line 1404, iTBS plus θtACS line 1406, and iTBS plus sham tACS line 1405. In some embodiments, spectral perturbation graphs measured frequency in Hertz per millisecond. In some embodiments, a shading scale ranged from 0 microVolts squared ($\mu V^2$) to 2 $\mu V^2$. In some embodiments, the natural frequency power analysis 1402 measured percent change at T0, T1, and T2. In some embodiments, the natural frequency shift analysis 1403 measured frequency change at T0, T1, and T2. In some embodiments, θtACS was done at 5 Hz. In some embodiments, γtACS was done at 70 Hz. In some embodiments, there were no visible changes in spectral power over the vertex.

Personalized TMS Targeting and Intensity Adjustment

In some embodiments, knowledge of the pathophysiology of a disease can be used to optimize spatial targeting (i.e., brain stimulation targets and corresponding location or placement of a stimulation coil on a scalp) or stimulation parameters including, but not limited to, intensity, frequency or waveform, to maximize the impact of rTMS in Alzheimer's patients.

Method of Target Identification

FIG. 1 provides an exemplary method for identifying a stimulation hotspot based on (i) structural and functional imaging data collected in patients with Alzheimer's Disease, and further refined via a (ii) "TMS-EEG Functional Search" based on TMS-Evoked Potentials (TEPs). In some embodiments, the method is used for identifying network-level targets or personalization via TMS-EEG functional search. In some embodiments, biophysical modeling can be applied for stimulation intensity adjustment. In some embodiments, for example, identifying network-level targets or personalization via TMS-EEG functional search is a two-step process. In some embodiments, the first step comprises calculating a group-level map characterizing the topography of the Default Mode Network (DMN) in AD patients. The Precuneus as the most highly connected node of the DMN, As such, In some embodiments, further spatial optimization may be carried out by conducting a seed-based connectivity analysis using the other main nodes of the DMN as seed regions, estimating their connectivity with the Precuneus, and identifying the local maxima of within-network connectivity inside the Precuneus region. In some embodiments, the process of further spational optimization may be repeated iteratively for each node (e.g., left angular gyrus, right angular gyms, left medial prefrontal cortex, right medial prefrontal cortex, left temporal lobe including, but not limited to, hippocampal region, right temporal lobe including, but not limited to, hippocampal region), resulting in multiple connectivity maps. In some embodiments, the maps may then be combined together, resulting in a "Precuneus weighted mask" highlighting the subregions of the Precuneus most highly connected with the rest of the network. In some embodiments, stimulation over these subregions may offer the highest probability for local activity to propagate within the entire DMN when stimulating the Precuneus. In some embodiments, the local maxima of highest functional connectivity may be selected and its shortest path to the cortex/scalp may be projected to guide the placement of the TMS coil on the scalp. As described herein, this approach is only one solution to identify the most suitable candidate node for stimulation or a subregion within it. Other methods may include, as non-limiting examples, estimating the average nodal degree of each region, their path length, their controllability within the network control theory framework, their evolutionary dynamics, or leveraging other scans to derive, structural, metabolic, perfusion, or diffusion information for each brain region or network of interest, or any combination thereof.

In some embodiments, the second step comprises each patient receiving a train of single-pulse TMS, for example, 60 pulses, over the Precuneus identified on the basis of fMRI data as described herein. In some embodiments, the patient receives a train of single-pulse TMS concurrently to EEG recording via a 64 channels EEG system. In some embodiments, the TMS coil position may be constantly monitored using a neuronavigation system coupled with an infrared camera. In some embodiments, data may be preprocessed to remove artifacts and filtered in order to identify early onset TMS-evoked potentials (TEPs), reflecting local neuronal activity generated in response to each TMS pulse. As described herein, in some embodiments, target optimization may be achieved via a grid search over an area of, for example, approximately 5-by-5 centimeters around the original fMRI-defined stimulation target and by visualizing TEPs directly after each TMS delivery, therefore allowing to instantaneously check amplitude and shape of each TEP and identify spatial locations within the precuneus generating the highest response to TMS for each patient ("TMS-EEG Functional Search"). In some embodiments, the selection of TMS location in the brain may be performed by selecting the brain region providing the highest TEPs' amplitude locally (i.e., in the stimulated area, as measured via TMS-EEG) and the highest TEPs amplitude in other nodes of the default mode network located in the frontal lobe of the brain and temporo-parietal cortex of the brain (including but not limited to the medial frontal cortex, dorsolateral prefrontal cortex, angular gyrus, middle temporal lobe). The TMS location in the precuneus providing the highest balance between induction of brain activity both in the precuneus region and other nodes of the default mode network is selected as the stimulation targets, with the aim to induce the maximal network-level activation on top of a local response in the precuneus.

Personalization of Stimulation Intensity

FIG. 1B provides an exemplary method for defining intensity applied during repetitive TMS visits as a combination of TMS-based measures collected at baseline on each patient, specifically (i) resting-state motor threshold calculated by TMS of the right-hand representation in the left motor cortex, and (ii) TMS-evoked potentials collected during single-pulse TMS of the Precuneus. In some embodiments, an ad-hoc algorithm may be used to weigh the different measures, leading to a final estimate of the optimal, personalized stimulation intensity to be adopted for rTMS treatment sessions for each patient. In some embodiments, data used for computing the stimulation intensity can be collected during a separate TMS-EEG visit conducted on a different day from the first rTMS visit. In some embodiments, the first step of personalizing stimulation intensity comprises calculating resting motor threshold calculated from the left motor cortex. In some embodiments, the first step targets right-hand representation from the left motor cortex. In some embodiments, intensity of stimulation may be set at 100% of the resting motor threshold (RMT), defined as the lowest intensity producing motor evoked potentials (MEPs) of greater than 50 µV in at least five out of 10 trials in the relaxed first dorsal intereosseous (FDI) muscle of the right hand.

In some embodiments, the second step of personalizing stimulation intensity comprises using data collected during a TMS-EEG session to optimize the location of TMS targets on the basis of TMS-EEG Functional Search ("OptiSearch") procedure. In some embodiments, evoked activity after a session of more than two TMS pulses may be averaged, revealing TMS-evoked potentials (TEPs) at different latencies between 5 ms and 500 ms after TMS. The amplitude of the TEPs may be calculated for each patient. In some embodiments, the calculated amplitude may be used as a proxy of individual responsiveness to TMS and therefore as an index of precuneus' excitability and reactivity. In some embodiments, the amplitude of TEPs may then be used to correct the stimulation intensity obtained from stimulation of the motor cortex (i.e., RMT), with the goal of adapting TMS stimulation intensity on the basis of TEPs.

In some embodiments, the third step of personalizing stimulation intensity comprises performing additional analyses to estimate the induced E-field over the TMS target. In some embodiments, this estimate can use a realistic volume conductor head model generated using MRI images and segmentation from a validation dataset, and based on anisotropic conductivity values for each tissue class expressed in S/m. In some embodiments, the set of resulting meshes, comprehensive of gray and white matter, scalp, bone, or cerebrospinal fluid, may be used to calculate an E-field distribution for a specific TMS coil design, accounting for coil-to-scalp distance and coil current. In some embodiments, the estimated E-field can be used to (a) retrospectively calculate individual differences in the amount of current reaching a target region and explain differences in response to a treatment, or (b) to adjust stimulation location or intensity so that all participants receive the same amount of induced cortical stimulation.

Personalization of Stimulation Frequency

FIG. 1B provides an exemplary method for determining the frequency applied during repetitive TMS visits by combining TMS-based measures collected at baseline on each patient. In some embodiments, the specific TMS-based measures are TMS-EEG evoked oscillations collected during single-pulse TMS assessment of the precuneus. In some embodiments, an ad-hoc algorithm may be used to weigh the different measures, leading to a final estimate of an optimal, personalized stimulation frequency to be adopted for rTMS treatment sessions for each patient. In some embodiments, data used for computing the stimulation frequency can be collected during a separate TMS-EEG visit conducted on a different day from the first rTMS visit.

In some embodiments, the first step of personalizing stimulation frequency comprises using the data collected during the TMS-EEG session to optimize the location of TMS targets on the basis of TMS-EEG Functional Search procedure. In some embodiments, TMS-evoked activity after a session of more than 10 TMS pulses may be averaged. In some embodiments, a time or frequency analysis is performed in epochs starting 1 s before to 1 s after a TMS pulse to evaluate TMS-evoked oscillatory activity.

In some embodiments, the second step of personalizing stimulation frequency comprises calculating event-related spectral perturbation (ERSP) values based on Morlet wavelets to analyze individual time-frequency domain responses. For example, in some embodiments, calculating ERSP values comprises convolving a mother wavelet at 100 linearly-spaced frequencies spanning 5 to 50 Hz, with 3.5 cycle wavelets and a 0.5 scaling factor. In some embodiments, determining a peak of individual frequency for each subject at each stimulation site, may include, but is not limited to, analyzing the global ERSP (gERSP) response by calculating the sum of power values for each frequency within the 20-200 ms time window, and then determining which frequency had the highest value. For example, in this specific case, the max frequency is not driven alone by a single frequency with a very high peak, but may instead be captured by a frequency with a moderate yet sustained response that is larger than at other frequency bands.

TMS Optimization Approaches Based on Limited Data

Target Identification Using Normative Brain Networks Templates

As described herein, in some embodiments, the system and methods for treatment of AD via rTMS may be applied using normative network templates when brain scans of a patient are only partially available. In some embodiments, if only structural brain scans are available, templates representing brain networks and regions of interest may be used via a spherical or linear co-registration algorithm adapting the topography of target networks or regions to individual brain anatomy. FIG. 2A provides an exemplary method for accurately identifying regions such as the precuneus and networks such as the DMN, for example, to provide guidance on initial coil placement for subsequent functional search via TMS-EEG. In some embodiments, the method described herein also leverages ad-hoc maps created by the inventors highlighting targets for rTMS stimulation based on accumulated knowledge of AD and dementia pathophysiology. FIG. 2B provides an exemplary map of patterns activation during a specific cognitive task. In some embodiments, maps include information on, but not limited to, patterns activation during a specific cognitive task, of atrophy, hypometabolism, protein accumulation or functional connectivity breakdown.

Target Identification Using Scalp-Based Inference and Normative Brain Scans

FIG. 2C provides exemplary system and methods for treatment of AD via rTMS by using scalp-based navigation when neither functional nor structural brain scans of a patient are available. In some embodiments, reference points include but are not limited to where the bilateral tragus, inion and nasion are located on a patient's head, and their distance measured with a tape measure. In some embodiments, half the distance between inion-nasion and tragus-tragus is calculated, with the intersection of the two points determining the location of scalp vertex. In some embodiments, the international 10/20 or 10/10 EEG reference system can be used to derive the approximate location of EEG electrode positions. In some embodiments, the location of the precuneus and posterior cingulate cortex region can be estimated based on normative functional MRI data from a dataset of AD patients. In some embodiments, the dataset provides the average location of the scalp site corresponding to the shortest linear trajectory connecting with the precuneus in a template AD brain. In some embodiments, the location of the scalp is then expressed as a % distance from vertex and other scalp reference points such as the inion. In some embodiments, the % distance is then identified on the scalp of a patient, corresponding to the average best cortical site for TMS to target the precuneus region. In some embodiments, the same procedure as described herein can be applied to other brain regions.

Target Identification in the Absence of TMS-EEG Data

FIG. 3 provides exemplary system and methods for treatment of AD via rTMS by using brain scans of a patient when TMS-EEG data is not available and the Opti-Search procedure cannot be completed. In some embodiments, an available normative dataset of AD patients collected by the inventors including, but not limited to, individual brain scans, EMG, EEG and TMS-EEG data can be used to create a set of reference measurements including, but not limited to, scalp-cortex distance estimated from structural brain scans, corticospinal excitability, TMS-EEG reactivity, or estimated induced electric field based on coil position and a range of stimulation intensities. In some instances, a regression model may be used to estimate the intensity of stimulation to be used on a patient's precuneus, based on the relationship between the average intensity for precuneus stimulation used in the dataset of AD patients and their respective other measures (e.g., cortical excitability, scalp-cortex distance, TMS-EEG reactivity). For example, in some embodiments, the regression model based on the database of AD patients may indicate that stimulation intensity for the precuneus in an AD patient can be estimated by calculating the sum of corticospinal excitability value*$\beta 1$, scalp-cortex distance*$\beta 2$, induced e-field in the precuneus*$\beta 3$, where $\beta 1$-2-3 are regression beta values calculated from the normative dataset of AD patients.

Subcortical Network-Based Targeting Via TMS

FIG. 4 provides an exemplary method comprising using structural and functional brain scans to estimate the connectivity between a subcortical target and cortical regions targetable via noninvasive brain stimulation. In some embodiments, this method is used for iteratively testing the strength and distribution of connectivity of each cortical target and identifying the optimal superficial area to be stimulated to maximize the chance of activating a subcortical target. In some embodiments, as described herein, identification of a patient-specific brain activation during a memory task in a patient with Alzheimer's Disease highlights the involvement of the default mode network. In some embodiments, the method includes, but is not limited to, identification of an optimal cortical target for hippocampus modulation by using structural and diffusion MRI data for visualizing white matter fiber tracts connecting the stimulated superficial area (e.g., angular gyrus) with subcortical targets of known interest for Alzheimer's Disease (e.g., the hippocampus for its role in memory processing). In some embodiments, white matter fibers may be estimated from multiple sub-regions of the left angular gyrus, with the subregion displaying the strongest white matter fiber pathway towards the hippocampus selected as a final personalized target. AD pathophysiology is characterized by alterations of both cortical and subcortical brain structures, with the latter including key regions such as the hippocampus and the amygdala. However, noninvasive brain stimulation methods may not be capable of directly targeting subcortical regions, while they can instead effectively modulate activity of cortical regions. Thus, the methods described herein leverage network neuroscience principles and methods from modern connectomics analysis to postulate the possibility to access desired deep targets by stimulating strongly connected cortical areas. In some instances, this may stimulate regions such as the hippocampus to induce changes in memory performance or increase local metabolism.

Data Processing Methods

In some embodiments, data processing can be performed via custom code in languages such as Python and Matlab. In some embodiments, data processing includes, but is not limited to, solutions for automated cleaning or preprocessing as well as semi-automated solutions with the possibility for manual identification of artifacts. In some embodiments, processing and analysis may be done as part of separate modules, covering (i) data collection, (ii) data validation and format conversion, (iii) data cleaning or preprocessing, (iv) data analysis, or (v) detailed report creation, including, but not limited to, optimal stimulation target and parameters and summary of processing steps.

Brain Scans Processing

In some embodiments, brain scans used for brain region targeting can contain information on (i) brain structural properties, including but not limited to density, volume, thickness, gyrification, sulcal depth of grey or white matter, CSF distribution, diffusivity and anisotropy of white matter, or spectroscopy profile of neurotransmitters, or any combination thereof; and (ii) functional properties of the brain, including but not limited to hemodynamic response, blood perfusion, metabolic activity (e.g., glucose consumption), or protein burden. In some embodiments, steps for preparing brain scans for statistical analysis include, but are not limited to, conversion of single images to a 3D volume format; segmentation in brain tissue classes; spatial and temporal filtering; removal of physiological noise; removal of image artifacts; extraction of average values or timeseries of brain activity; co-registration to a common anatomical or functional template for group-level analysis; or calculation of evoked activity when multiple scanning conditions are present as in the case of block-fMRI data. In some embodiments, follow-up analysis can be performed on both voxel-based volumetric data or vertex-based surface images, and may include, but is not limited to, masking of clean data on the basis of anatomical or functional atlases describing relevant networks or brain regions that can be targeted by TMS.

EEG Data Processing

In some embodiments, EEG data collected before, during and after a single TMS pulse during a TMS-EEG recording session may be processed in preparation for data analysis and selection of the optimal TMS target. In some embodiments, the steps include, but are not limited to, raw data conversion in .edf format; trimming of raw data into epochs of predefined length, including segments capturing pre- and post-TMS brain activity; normalization of post-TMS activity by subtracting the average signal amplitude of EEG data collected pre-TMS; automated or semi-automated data inspection to identify EEG channels with excessive noise or artifacts; zero padding of activity concurrent to the single TMS pulse to remove early signal decay and muscle artifacts induced by the TMS pulse (according to voltage-based thresholds, kurtosis and joint probability); independent component analysis (ICA) to identify and remove components including early TMS evoked high amplitude electrode, with an additional data reduction via principal component analyses (PCA) to minimize overfitting and noise components; interpolation of previously zero-padded signal across the TMS pulse; band pass filtering using a forward-backward filter typically between 1 to 150 Hz; notch filtering to account for line noise; referencing to global average; a second ICA to manually remove all remaining artifactual components including eye movement/blink, muscle noise (EMG), single electrode noise, TMS evoked muscle activity, cardiac signal (EKG), as well as auditory evoked artifacts (artifacts are identified and labeled on the basis of their spectral frequency profile, power spectrum, amplitude, scalp topography, and time course); application of machine learning and deep learning algorithms for identification of residual artifacts; interpolation of previously removed electrodes.

In some embodiments, the order of steps described herein can vary, and specific adjustments are implemented based at least in part on individual brain properties or pathology-specific artifact and signal characteristics. Features to consider include, but are not limited to, for example, the level of cortical atrophy impacting the induced electric field in the brain; known alterations of neurotransmitters' activity impacting the amplitude and shape of particular evoked potentials; elevated movement and muscle activations during EEG recording; elevated levels of oscillatory activity in the EEG due to drowsiness or general slowing of brain activity typical of the brain of patients with ADD.

Infrastructure

FIG. 5 provides an exemplary infrastructure system and method to allow for, among other steps, stimulation target and parameters optimization, data storage and processing, or treatment delivery, or any combination thereof. In some embodiments, the treatment flow may include, but is not limited to, the following steps:

1) Patient gets prescribed the rTMS treatment by a clinician;
2) Patient is scheduled for a target definition and optimization session;
3) Patient completes a brain scanning session to identify and characterize the topography of a target brain network or region;
4) Brain scans are processed and a first mask of the precuneus region is identified;
5) On a separate visit, patient's EMG, TMS or EEG data are collected from the precuneus region previously identified via brain scans;
6) Results are streamed to a data processing unit or platform where data cleaning and analysis take place in order to further identify the optimal target for stimulation;
7) The clinician or operator receives information about the personalized target and stimulation parameters for the patient, and schedule the treatment sessions;
8) Patient undergoes the rTMS treatment for the prescribe duration; data from each visit, including but not limited to neuronavigation data, get stored locally in the infrastructure, as well as in a remote cloud system;
9) Patient completes follow-up TMS-EEG visits during the treatment course to monitor disease progression and treatment response;
10) Data gets stored and an analysis platform is used to further optimize the treatment on the basis of aggregate data and group-level insight on treatment efficacy.

In some embodiments, the steps can be combined or substituted with any suitable steps of the other methods disclosed herein. In some instances, for example, starting from step #3 a clinical staff member may access a URL link and authenticate their user account with a service (e.g., Auth0). Then the clinical staff member can set up the TMS-EEG apparatus and pair it with the web browser. In some embodiments, Following this pairing, data, including, but not limited to, raw EEG data or survey metadata (e.g., demographic information, brain scan data, neuronavigation parameters) and a request may be sent from the EEG to the back-end via an application programmers interface (API). This data and request are then routed through the gateway ingress and gateway.

In some embodiments, the API is setup to have a set of main actions from the gateway, including, but not limited to:
1. Streaming—the ability to query and stream data (for instance, EEG time series data); for example, note that streaming includes, but is not limited to encryption and decryption of data using cryptographic keys through a service like Amazon Key Management Service (KMS).
2. Data Collection—the ability to collect, clean, featurize, and process raw EEG data, for example, with the intent to take in an EEG feed and get back a location in the brain to stimulate.
3. Object—the ability to access and query the database (MongoDB).
4. Scheduling—the ability to book and post a patient schedule or appointment,
5. Billing—the ability to access billing information and charge per session with a third-party service provider, for example, like Stripe.
6. Notifications—the ability to send emails to users upon certain actions being completed (e.g., a session being completed or billing successful, or targeting results being ready)
7 Data Export—the ability to request and create data bundles or downloads from information in the database. For example, this can be especially useful to track sessions over time and measure improvement in symptoms.
8. Baseline users—the ability to baseline users through a survey instrument such as, but not limited to, a digitized Mini-Mental State Exam (MMSE), or post information from the electronic health record (HER) into the survey itself.

In some instances, data from the database may be formatted to be compatible with FHIR, which is a standard for exchanging healthcare information electronically. In some instances, data can be posted directly from the database into the EHR through use of APIs. In some instances, the whole architecture (i.e. infrastructure) or any part of the architecture described herein can be run locally or in the cloud through docker containers. There can be options to spin up servers and clusters relative to geographies (e.g., India vs. United States). This is important for data provisioning to comply with GDPR, including, for example, keeping India data in India, or European data in Europe. In some instances, the database can search through users and can delete user data upon request to comply with GDPR and other privacy laws.

Database for Treatment Optimization

In some embodiments, the architecture described herein may be used to store brain scans, EEG, EMG and TMS data, individual patients' characteristics including, but not limited to, clinical, demographics and cognitive profile, optimal parameters for stimulation, or for group-level analysis and further optimization of the TMS-based intervention, or any combination thereof. In some embodiments, machine learning and deep learning solutions (e.g., convolutional neuronal networks and clustering algorithms) may be used to search through the database and identify, for instance, individual data features linked to response to treatment, clusters of individuals with similar stimulation parameters, clusters of individuals with similar response to treatment, estimate dose-response curves, build predictive models of disease progression.

Example Use Cases

Two examples of the potential applications of the systems and methods described above are described below. The first one is a direct application of the proposed solutions for personalization of rTMS parameters for the treatment of AD patients, reporting results from a phase-2, randomized, double-blind, placebo-controlled clinical trial demonstrating the efficacy of the rTMS treatment targeting the precuneus in a sample of 50 AD patients.

An example of $T^2$ formulation (i.e., combined TMS and other interventions) is also reported. Results of a study showing the effect of an rTMS intervention applied together with a plasticity-inducing brain stimulation technique (i.e., tACS) are shown, showing the increased efficacy of the combined solution in modulating brain activity and reactivity.

EXAMPLES

Data collected by the Inventors demonstrate the safety, feasibility and efficacy of a long-duration treatment course of rTMS based on a novel approach for targeting functional networks altered in AD, specifically the DMN and the Precuneus region (DMN-p) with clinical and cognitive effects captured via a phase-2, double blind, randomized, placebo controlled clinical trial in 50 patients with AD. Below are reported details of the clinical trial, information on the intervention and targeting procedures, and methods for treatment personalization based on TMS-EEG and brain scan analysis. The methods, experimental designs, and other aspects of the examples below are not intended to be limiting in any way.

Example 1: Trial Design Using rTMS

FIG. 6 provides an exemplary study design described herein, comprising a monocentric, randomized, sham-controlled, double-blind trial of rTMS over the DMN-p in mild to moderate AD patients. After recruitment and baseline assessment, patients were randomly assigned in a 1:1 ratio to receive either real or sham DMN-p DMN-p-rTMS in addition to their stable drug regimen with acetylcholinesterase inhibitors therapy. All treatments were administered for 24 weeks with no interruptions. The trial comprised a 24-week treatment period with a 2-week intensive course in which rTMS of the DMN-p DMN-p was applied daily 5 times per week (W1 and W2), Monday to Friday, followed by a maintenance phase in which the same stimulation was applied weekly for 22 weeks (W3-W24).

Each rTMS session consisted of forty trains of 2 seconds delivered at 20 Hz, spaced-out by 28 seconds of no stimulation (total number of stimuli: 1600), for a total duration of approximately 20 minutes. During the entire period of 24 weeks a total of 51200 pulses were delivered for each patient. rTMS was carried out using a magnetic stimulator connected with a figure-of-eight coil.

Efficacy assessments were conducted at baseline (W0) for enrolled patients and caregivers, and repeated at weeks 12 (W12) and 24 (W24) (or upon early termination) by raters who were blinded in respect to the assignment group. Investigators, patients, and their caregivers were also blinded. At each clinical visit (or upon early termination), adverse events (AEs) were recorded, vital signs measured and physical and neurological examination performed. An independent Data Monitoring Committee monitored the patients' safety according to the Data Monitoring Committee Charter.

Primary and Secondary Outcome Measures

The primary outcome measure was the change at 24 weeks from baseline of the Clinical Dementia Rating Scale Sum of Boxes (CDR-SB) score (CDR-SB scores range from 0 to 18, with higher scores indicating worse cognition and daily function). The intention-to-treat analysis set included all patients who had post-baseline efficacy data. The secondary outcome measures were:
  Change at 24 weeks from baseline on the Alzheimer's Disease Assessment Scale-Cognitive Subscale (ADAS-Cog) 11 [25];
  Change at 24 weeks from baseline on MMSE score;
  Change at 24 weeks from baseline on the Activities of Daily Living (ADCS-ADL) [26];
  Change at 24 weeks from baseline on the Frontal Assessment Battery (FAB) [27];
  Change at 24 weeks from baseline on the Neuropsychiatric Inventory (NPI) [28].

TMS-EEG was used as a marker of cortical excitability, plasticity and reactivity via analysis of TMS-evoked potentials (TEPs) and oscillatory activity measured as TMS-related spectral perturbation (TRSP) evoked by single-pulse TMS applied over the DMN-p during concurrent EEG recordings. Source reconstruction analysis was performed to define the spatial distribution of the TMS-EEG evoked activity around the stimulated area.

Sample Size Estimation and Statistical Analysis

A total of 50 randomly assigned patients, 25 per group, were planned on the basis of power calculation from our previous study that assessed the effects of two weeks of DMN-p-rTMS on cognitive functions in a small sample of AD patients. Considering the effect size, equal to 0.39 obtained as post-pre means over pooled standard deviation, observed for Memory performance scores in the pilot study with a treatment of 2 weeks, it was plausible for the current study, with treatment duration ten times longer than the pilot study, to have an effect size at least double (i.e., about 0.75). With this effect size, adopting a two-tailed paired Wilcoxon signed-rank, with type I error alpha=0.05 and a plausible correlation between pre-post measured variables of 0.7, the minimum sample for reaching a power of 0.8 was estimated equal to n=17; and up to n=23 to ensure a power of 0.9. The choice of N=50 (25 per group) ensured adequate size for within group analyses as well.

Covariate-adaptive randomization was performed and assigned by a statistician working in an independent institution. Normality assumption of end-point variables were assessed by inspection of the distribution plots and by Kolmogorov-Smirnov and Shapiro-Wilk tests.

Statistical Analysis

The longitudinal assessment of the end-points across groups was performed through generalized linear mixed model (GLMM) for repeated measures with random intercept and random slope to account for individual differences at baseline and to assess individual change through follow-up. GLMM were applied to CDR-SB and the other outcome measures of efficacy, ADAS-Cog11, MMSE, ADCS-ADL, FAB and NPI, as dependent variables and "group", "time" and "group×time" interaction as independent factors.

Sample 86 patients were screened and 50 underwent randomization. The mean age of the total sample of patients was 73.7 years (SD=6.6, range 62 to 84), and 52% were female. Patients had a mean MMSE raw score at baseline of 21.3 (SD=2.5). The baseline patients' demographics and clinical characteristics did not differ between the DMN-p-rTMS and sham-rTMS groups. A total of 5 patients withdrew from the trial before completion (3 in the DMN-p-rTMS group and 2 in the sham-rTMS group). A total of 45 patients (90%) completed the treatment period. On average, the mean number of rTMS sessions completed during 24 weeks did not vary between AD patients allocated to either experimental group (DMN-p-rTMS: 30.2; sham-rTMS 30.5).

Patients Characteristics

Patients were eligible if they had an established diagnosis of probable mild-to-moderate AD according to National Institute of Neurological and Communicative Disorders and Stroke and the Alzheimer's Disease and Related Disorders Association criteria; aged >50≤85 years; had a Clinical Dementia Rating (CDR) score of 0.5-1 and Mini Mental State Examination (MMSE) score of 18-26 at screening, indicating mild to moderate AD; had one caregiver; had been treated with acetylcholinesterase inhibitor for at least 6 months; and had performed lumbar puncture for cerebrospinal fluid biomarkers analysis for diagnostic purposes. Patients underwent medical and neurological evaluations, including magnetic resonance imaging or computed tomography. Patients were excluded if had extrapyramidal signs, history of stroke, other neurodegenerative disorder, psychotic disorders, or if they had been treated six months before enrollment with antipsychotics, antiparkinsonian, anticholinergics or antiepileptic drugs. The trial was approved by the review board and ethics committee at Santa Lucia Foundation and was conducted in accordance with the principles of the Declaration of Helsinki and the International Conference on Harmonization Good Clinical Practice guidelines. All patients or their parents or legal representatives provided written informed consent. Patients could withdraw at any point without prejudice. This report followed the CONSORT reporting guideline for randomized studies.

Results

Safety

Eight participants reported adverse events (AEs), 7 in the active DMN-p-rTMS, 1 in the sham-rTMS group. All events were mild and most of them resolved on the day of occurrence with either minor or no action (mild headache (n=3), scalp/skin discomfort (n=4), neck pain/stiffness (n=3), and fatigue (n=2).

Cognitive and Clinical Outcomes

The mean baseline CDR-SB total score was 4.1 (SD=1.8) for the DMN-p-rTMS group, and 4.6 (SD=1.5) for the sham-rTMS group. There were significant differences (baseline vs. week 24) in the cognitive performance as measured by the CDR-SB total score in the active rTMS group compared to sham. GLMM for repeated measures on CDR-SB scores showed significant result in terms of difference between group (p=0.038) and time×group (p=0.009) interaction, with patients treated with sham-rTMS showing a general worsening of cognitive performance of patients over time that was not evident in the DMN-p-rTMS group. FIG. 7A provides an exemplary depiction of results, wherein the GLMM estimated mean change (baseline–week 24) in CDR-SB score was −0.25 for DMN-p-rTMS (95% confidence interval (CI) [−4.8, 4.3]) and −1.42 for sham-rTMS group (95% CI [−6.0, 3.3]). The rate of responders, defined as the percentage of patients showing an increase 1 point at the CDR-SB score, was 68.2% in the DMN-p-rTMS group and 34.7% in the sham group.

The analysis of secondary clinical outcomes showed that there were significant longitudinal differences between the DMN-p-rTMS group and the sham-rTMS group for the ADAS-COG11, the MMSE and the ADCS-ADL scores but not and not for the FAB and NPI scores. The mean baseline ADAS-Cog11 total score was 22.6 (SD=7.4) for the DMN-p-rTMS group, and 24.8 (SD=6.5) for the sham-rTMS group. GLMM for repeated measures on ADAS-Cog11 scores (adjusted for age and education) showed significant result in terms of time×group (p=0.035) interaction. FIG. 7B provides an exemplary depiction of results, wherein the GLMM estimated mean change (baseline–week 24) in ADAS-Cog11 score was −0.67 for DMN-p-rTMS (95% confidence interval (CI) [−21.5, 20.2]) and −4.2 for sham-rTMS group (95% CI [−25.1, 16.6]).

The mean baseline MMSE total score was 21.2 (SD=2.7) for the DMN-p-rTMS group, and 21.5 (SD=2.4) for the sham-rTMS group. GLMM for repeated measures on MMSE scores (adjusted for age and education) showed significant result in terms of time×group (p=0.048) interaction. FIG. 7C provides an exemplary depiction of results, wherein the GLMM estimated mean change (baseline–week 24) in MMSE score was 0.24 for DMN-p-rTMS (95% confidence interval (CI) [−6.5, 7.0]) and 1.8 for sham-rTMS group (95% CI [−5.1, 8.8]). The baseline mean of ADCS-ADL total score was 58.6 (SD=9.7) for the DMN-p-rTMS group and 58.3 (SD=9.7) for the sham-rTMS group.

FIG. 7D provides an exemplary depiction of results, wherein the estimated mean change (baseline–week 24) in ADCS-ADL scores was −0.7 for AD-DMN-p-rTMS (95% CI [−27.2, 25.8]) and 7.5 for sham-rTMS group (95% CI [−20.5, 35.5]), showing an improvement of the DMN-p-rTMS with respect to sham-rTMS group (interaction effect: p=<0.001).

FIG. 7E provides an exemplary depiction of results, wherein the estimated mean change (baseline–week 24) in NPI score was −1.4 for DMN-p-rTMS (95% CI [−15.7, 13.6) and −3.7 for sham-rTMS group (95% CI [−25.8, 21.9]), revealing no significant effects.

FIG. 7F provides an exemplary depiction of results, wherein the baseline mean for FAB total score was 10.7 (SD=3.9) for the DMN-p-rTMS group, and 10.2 (SD=3.4) for the sham-rTMS group. Estimated mean change in FAB score was −0.01 for DMN-p-rTMS (95% CI [−7.7, 7.7]) and 0.29 for sham-rTMS group (95% CI [−7.4, 8.0]) revealing no significant effects. Baseline mean for NPI total score was 9.8 (SD=10.2) for the DMN-p-rTMS group, and 12.6 (SD=11.7) for the sham-rTMS group.

FIG. 8A provides an exemplary depiction of results, wherein the neurophysiological analysis showed that TMS-evoked cortical activity was stable in the DMN-p-rTMS group while decreased in the sham-rTMS group (group×time interaction [$F(1,126)=6.65$; $p=0.011$; post-hoc: shamW0–shamW24 p=0.002]).

FIG. 8B provides an exemplary depiction of further results, wherein the DMN source activity did not change in patients treated with DMN-p-rTMS, while decreased in the sham-rTMS patient group. FIG. 9 provides an additional exemplary depiction of results, wherein an increase in fast brain oscillatory activity mostly involving the beta and gamma band was also observed after real rTMS, but not after sham rTMS where a decrease in gamma spectral power (imputable to progression of disease) was observed instead.

Example 2: Experimental Study of $T^2$ Formulation

Fast oscillatory activity in the gamma band has been associated with plasticity processed in the human brain. Given the impairment of plasticity mechanisms in disorders such as dementia and Alzheimer's Disease, the proposed protocol based on multi-session rTMS over the precuneus in AD patients could benefit from the combination with an additional intervention aimed at specifically boosting plasticity in the brain. In this context, the combination of rTMS with Alternating Current Stimulation (tACS) targeting gamma activity (>30 Hz) could generate additive effects over brain activity and lead to even stronger clinical outcomes than the application of each modality alone.

In the study described below, the effect of a combined intervention based on rTMS and tACS was tested in a sample of 20 healthy adult individuals. Participants were naïve to brain stimulation, had no prior history of psychiatric disorders and were on a stable dose of medications for at least 6 weeks before joining the study. Participants received a specific form of rTMS called intermittent Theta Burst TMS (iTBS), a plasticity inducing protocol known to increase cortical excitability and reactivity for a sustained amount of time post-stimulation, and tACS at (ii) a target frequency within the gamma band (70 Hz), (iii) tACS at a control frequency in the theta band (5 Hz), and (iv) sham (placebo) tACS. The combined stimulation protocol was delivered over the left dorsolateral prefrontal cortex (DLPFC). Participants completed iTBS+70 Hz, iTBS+5 Hz and iTBS+sham tACS over three separate study visits in different days.

Before (T0), immediately after (T1) and 20 minutes after (T2) stimulation, participants underwent a TMS-EEG recording from multiple scalp sites, including the region targeted by iTBS+tACS (left DLPFC), right DLPFC, and the vertex. FIGS. 10A-10D provide an exemplary depiction of results, wherein the TMS-EEG data was used to quantify cortical reactivity in the different conditions, and also to extract so-called natural frequencies for each stimulated site and identify possible changes in said region-specific oscillations after the combined intervention.

Results

A significant increase in the amplitude of TMS-evoked potentials after each single-pulse TMS perturbation delivered during the TMS-EEG sessions was observed for iTBS+ 70 Hz tACS, compared to iTBS+sham tACS and iTBS+5 Hz tACS (p.<0.05). FIG. 11 provides an exemplary depiction of results, wherein the effect was only present for the stimulated region left DLPPFC, and not for right DLPFC and the vertex. This suggests high spatial specificity of induced modulation of brain activity.

The effect of iTBS plus gamma tACS at 70 Hz was also visible when looking at spectral power perturbation and oscillatory activity generated by the combined intervention. FIG. 12 provides an exemplary depiction of results, wherein the iTBS+70 Hz significantly increased the spectral power of local oscillatory response in the gamma band (p.<0.05), compared to no visible effects for iTBS+5 Hz and iTBS+ Sham tACS. FIG. 13 and FIG. 14 provide exemplary depictions of results, wherein the shift in natural frequencies generated by single pulse TMS and their amplitude observed using TMS-EEG over the stimulated brain region (left DLPFC) was not observed when looking at right DLPFC (FIG. 13) and the vertex (FIG. 14).

Embodiments

Embodiment 1. An embodiment comprising a method for identifying a first location in a brain of a subject suitable for non-invasive stimulation to treat or ameliorate a neurological or psychiatric disease, the method comprising: a. identifying, from scan data of the brain of the subject, a plurality of brain regions forming a brain network; and b. determining, within a first brain region of the plurality of brain regions, as the first location suitable for non-invasive stimulation to treat or ameliorate the neurological or psychiatric disease, a sub-region of the first brain region strongly connected to one or more other brain regions of the plurality of brain regions.

Embodiment 2. The method of embodiment 1, wherein the scan data is functional MRI data (fMRI).

Embodiment 3. The method of embodiment 1, wherein the brain network is a Default Mode Network (DMN).

Embodiment 4. The method of embodiment 1, wherein the first brain region comprises at least a portion of the precuneus.

Embodiment 5. The method of embodiment 1, wherein the neurological or psychiatric disease is Alzheimer's Disease.

Embodiment 6. The method of embodiment 1, wherein the identifying of the plurality of brain regions forming the brain network is further based on neuroimaging data for a plurality of subjects having the neurological disease.

Embodiment 7. The method of embodiment 1, wherein the scan data comprises neuroimaging data.

Embodiment 8. The method of embodiment 1, further comprising: providing non-invasive stimulation to the determined first location of the brain of the subject.

Embodiment 9. The method of embodiment 1, wherein the identifying of the plurality of brain regions forming the brain network is based at least in part on one or more of a brain connectomics, network theory, graph theory, or control theory analysis framework.

Embodiment 10. The method of embodiment 1, further comprising providing non-invasive stimulation to the subject.

Embodiment 11. The method of embodiment 10, wherein providing non-invasive stimulation comprises providing at least one of transcranial electrical stimulation or transcranial magnetic stimulation to the determined first location of the brain of the patient.

Embodiment 12. The method of embodiment A1, further comprising: providing non-invasive stimulation to a plurality of locations within the first brain region including the first location; sensing, in response to the stimulation provided, at least one evoked potential; and selecting as a personalized stimulation target, one location of the plurality of locations as suitable for non-invasive stimulation to treat or ameliorate the neurological or psychiatric disease based on at least one characteristic of the at least one evoked potential.

Embodiment 13. The method of embodiment 12, wherein the plurality of locations are arranged in a grid.

Embodiment 14. The method of embodiment 12, wherein the at least one characteristic comprises a peak magnitude of the at least one evoked potential.

Embodiment 15. The method of embodiment 12, wherein selecting the personalized stimulation target comprises selecting the location of the plurality of locations having a largest peak magnitude for the at least one evoked potential.

Embodiment 16. The method of embodiment 12, wherein sensing the at least one evoked potential comprises sensing the at least one evoked potential using electroencephalography.

Embodiment 17. The method of embodiment 12, further comprising: treating or ameliorating the neurological or psychiatric disease by providing the non-invasive stimulation to the determined personalized stimulation target.

Embodiment 18. The method of embodiment 17, wherein the non-invasive stimulation provided to the determined personalized stimulation target is effective to treat or ameliorate the neurological or psychiatric disease of the subject so that the subject has an improved cognitive and clinical performance score compared to that of an untreated subject after a 12 week period.

Embodiment 19. The method of embodiment 17, wherein the non-invasive stimulation provided to the determined personalized stimulation target is effective to treat or ameliorate the neurological or psychiatric disease of the subject so that the subject has an improved cognitive and clinical performance score compared to that of an untreated subject after a 24 week period.

Embodiment 20. The method of embodiment 17, wherein the non-invasive stimulation provided to the determined personalized stimulation target is effective to treat or ameliorate the neurological or psychiatric disease of the subject so that the subject has a cognitive decline at least 25% smaller compared to that of an untreated subject after a 24 week period.

Embodiment 21. The method of embodiment 17, wherein the non-invasive stimulation provided to the determined personalized stimulation target is effective to treat or ameliorate the neurological or psychiatric disease of the subject so that the subject has a decline in disease severity at least 25% smaller compared to that of an untreated subject after a 24 week period.

Embodiment 22. The method of embodiment 17, wherein the non-invasive stimulation provided to the determined personalized stimulation target is effective to treat or ameliorate the neurological or psychiatric disease of the subject so that the subject has a decline in functional independence at least 25% smaller compared to that of an untreated subject after a 24 week period.

Embodiment 23. The method of embodiment 17, wherein the non-invasive stimulation provided to the determined personalized stimulation target is effective to treat or ameliorate the neurological or psychiatric disease of the subject so that the subject has a decline in the amplitude of TEPs at least 25% smaller compared to that of an untreated subject after a 24 week period.

Embodiment 24. The method of embodiment 17, wherein the non-invasive stimulation provided to the determined personalized stimulation target is effective to treat or ameliorate the neurological or psychiatric disease of the subject so that the subject has a decline in network oscillatory activity at least 25% smaller compared to that of an untreated subject after a 24 week period.

Embodiment 25. The method of embodiment 17, wherein the non-invasive stimulation provided to the determined personalized stimulation target is effective to treat or ameliorate the neurological or psychiatric disease of the subject so that the subject has a decline in source-level network activity at least 25% smaller compared to that of an untreated subject after a 24 week period.

Embodiment 26. The method of embodiment 17, wherein the non-invasive stimulation provided to the determined personalized stimulation target is effective to treat or ameliorate the neurological or psychiatric disease of the subject so that the subject has a decline in network metabolic activity at least 25% smaller compared to that of an untreated subject after a 24 week period.

Embodiment 27. The method of embodiment 17, wherein the non-invasive stimulation provided to the determined personalized stimulation target is effective to treat or ameliorate the neurological or psychiatric disease of the subject so that the subject has a change in brain oscillatory activity compared to that of an untreated subject.

Embodiment 28. The method of embodiment 17, wherein the non-invasive stimulation provided to the determined personalized stimulation target is effective to treat or ameliorate the neurological or psychiatric disease of the subject so that the subject has an increase in fast oscillatory brain activity in the gamma band compared to that of an untreated subject.

Embodiment 29. The method of embodiment 17, wherein the non-invasive stimulation provided to the determined personalized stimulation target is delivered over multiple consecutive days, multiple non-consecutive days with a frequency of daily, once a week, or a combination thereof.

Embodiment 30. The method of embodiment 12, wherein the non-invasive stimulation provided to the determined personalized stimulation target is combined with a drug intervention affecting the central nervous system, delivered sequentially or simultaneously.

Embodiment 31. The method of embodiment 12, wherein the non-invasive stimulation provided to the determined personalized stimulation target is combined with one or more of a cognitive assessment, cognitive training, or cognitive enhancement intervention, delivered sequentially or simultaneously.

Embodiment 32. The method of embodiment 12, wherein the non-invasive stimulation provided to the determined personalized stimulation target is combined with a behavioral intervention, delivered sequentially or simultaneously.

Embodiment 33. The method of embodiment 12, wherein the non-invasive stimulation provided to the determined personalized stimulation target is combined with a different non-invasive stimulation intervention, delivered sequentially or simultaneously, including transcranial electrical stimulation.

Embodiment 34. The method of embodiment 33, wherein the second non-invasive stimulation intervention is transcranial Alternating Current Stimulation, delivered sequentially or simultaneously.

Embodiment 35. The method of embodiment 1, wherein the scan data comprises diffusion MRI data.

Embodiment 36. The method of embodiment 1, wherein the scan data comprises perfusion MRI data.

Embodiment 37. The method of embodiment 1, wherein the scan data comprises Positron Emission Tomography (PET) data indexing local perfusion/metabolic levels or indexing protein burden or measuring neuroinflammation.

Embodiment 38. The method of embodiment 1, wherein the brain network comprises one or more of the Fronto-Parietal control Network, the Sensorimotor Network, the Anterior Salience Network, the Dorsal Attention Network, the Ventral Attention Network, the Visual Network, the Auditory Network, or the Language Network.

Embodiment 39. The method of embodiment 1, wherein the first brain region comprises at least a portion of the angular gyrus.

Embodiment 40. The method of embodiment 1, wherein the first brain region comprises at least a portion of the temporal lobe.

Embodiment 41. The method of embodiment 1, wherein the first brain region comprises at least a portion of the medial prefrontal cortex.

Embodiment 42. The method of embodiment 1, wherein the neurological or psychiatric disease is Mild Cognitive Impairment (MCI).

Embodiment 43. The method of embodiment 1, wherein the neurological or psychiatric disease is Frontotemporal Dementia.

Embodiment 44. The method of embodiment 1, wherein the neurological or psychiatric disease is characterized by alterations of brain networks, such as Depression (DEP), Schizophrenia (SCZ), Autism (AUT), Attention Deficit & Hyperactivity Disorder (ADHD), Bipolar disorder (BP), amyotrophic lateral sclerosis (ALS), Parkinson's disease (PD), traumatic brain injury (TBI), Insomnia (INS), Disorder of Consciousness (DOC), headache (HD), multiple sclerosis (MS), Stroke (STR), and brain tumors (BT).

Embodiment 45. The method of embodiment 1, wherein the neurological or psychiatric disease is characterized by memory deficits.

Embodiment 46. The method of embodiment 1, wherein the neurological or psychiatric disease is characterized by deficits in cognitive control.

Embodiment 47. The method of embodiment 1, wherein the neurological or psychiatric disease is characterized by decrease of functional independence.

Embodiment 48. An embodiment comprising a method for determining a personalized stimulation target in a brain region to treat or ameliorate a neurological or psychiatric disease in a subject, the method comprising: a. non-invasively stimulating each location of a plurality of locations in a brain region of a subject; b. sensing, in response to the stimulation provided, at least one evoked potential; and c. selecting as a personalized stimulation target for the subject, one of the locations of the plurality of locations that is suitable for providing therapeutically effective non-invasive stimulation to treat or ameliorate the neurological or psychiatric disease, wherein the selecting is based on the at least one characteristic of the at least one evoked potential.

Embodiment 49. The method of embodiment 48, wherein the brain region is part of a Default Mode Network (DMN).

Embodiment 50. The method of embodiment 48, wherein the brain region comprises at least a portion of the precuneus.

Embodiment 51. The method of embodiment 48, wherein the neurological or psychiatric disease is Alzheimer's Disease.

Embodiment 52. The method of embodiment 48, wherein providing non-invasive stimulation comprises providing at least one of transcranial electrical stimulation or transcranial magnetic stimulation to the personalized stimulation target of the brain of the subject.

Embodiment 53. The method of embodiment 48, wherein the plurality of locations are arranged in a grid.

Embodiment 54. The method of embodiment 48, wherein the at least one characteristic comprises a peak magnitude of the at least one evoked potential.

Embodiment 55. The method of embodiment 48, wherein selecting the personalized stimulation target comprises selecting the location of the plurality of locations having a largest peak magnitude of the at least one evoked potential.

Embodiment 56. The method of embodiment 48, wherein sensing the at least one evoked potential comprises sensing the at least one evoked potential using electroencephalography.

Embodiment 57. The method of embodiment 48, further comprising: treating or ameliorating the neurological or psychiatric disease by providing the non-invasive stimulation to the selected personalized stimulation target.

Embodiment 58. The method of embodiment 48, wherein the brain network is the one or more of the Fronto-Parietal control Network, the Sensorimotor Network, the Anterior Salience Network, the Dorsal Attention Network, the Ventral Attention Network, the Visual Network, the Auditory Network, or the Language Network;

Embodiment 59. The method of embodiment 48, wherein the brain region comprises at least a portion of the angular gyrus;

Embodiment 60. The method of embodiment 48, wherein the brain region comprises at least a portion of the temporal lobe;

Embodiment 61. The method of embodiment 48, wherein the brain region comprises at least a portion of the medial prefrontal cortex;

Embodiment 62. The method of embodiment 48, wherein the neurological or psychiatric disease is Mild Cognitive Impairment (MCI).

Embodiment 63. The method of embodiment 48, wherein the neurological or psychiatric disease is Frontotemporal Dementia.

Embodiment 64. The method of embodiment 48, wherein the neurological or psychiatric disease is characterized by alterations of brain networks, such as Depression (DEP), Schizophrenia (SCZ), Autism (AUT), Attention Deficit & Hyperactivity Disorder (ADHD), Bipolar disorder (BP), amyotrophic lateral sclerosis (ALS), Parkinson's disease (PD), traumatic brain injury (TBI), Insomnia (INS), Disorder of Consciousness (DOC), headache (HD), multiple sclerosis (MS), Stroke (STR), and brain tumors (BT).

Embodiment 65. The method of embodiment 48, wherein the neurological or psychiatric disease is characterized by memory deficits.

Embodiment 66. The method of embodiment 48, wherein the neurological or psychiatric disease is characterized by deficits in cognitive control.

Embodiment 67. The method of embodiment 48, wherein the neurological or psychiatric disease is characterized by decrease of functional independence.

Embodiment 68. The method of embodiment 48, wherein the non-invasive stimulation provided to the selected personalized stimulation target is combined with a drug intervention affecting the central nervous system, delivered sequentially or simultaneously.

Embodiment 69. The method of embodiment 48, wherein the non-invasive stimulation provided to the selected personalized stimulation target is combined with a cognitive assessment, cognitive training or cognitive enhancement intervention, delivered sequentially or simultaneously.

Embodiment 70. The method of embodiment 48, wherein the non-invasive stimulation provided to the selected personalized stimulation target is combined with a behavioral intervention, delivered sequentially or simultaneously.

Embodiment 71. The method of embodiment 48, wherein the non-invasive stimulation provided to the selected personalized stimulation target is combined with a different non-invasive stimulation intervention, delivered sequentially or simultaneously, including transcranial electrical stimulation.

Embodiment 72. An embodiment comprising a method for determining parameters for non-invasive stimulation of a brain of a subject, the method comprising: a. sensing a plurality of evoked potentials in response to non-invasive stimulation of each location of a plurality of locations in a brain region of the subject; b. determining, based at least in part on at least one characteristic of the plurality of evoked potentials, personalized stimulation parameters for the subject, wherein the personalized stimulation parameters include a location of stimulation and one or more stimulation characteristics.

Embodiment 73. The method of embodiment 72, wherein the one or more stimulation characteristics include an intensity of stimulation and/or a frequency of stimulation.

Embodiment 74. The method of embodiment 72, further comprising: sensing a resting motor threshold in response to providing non-invasive stimulation of a motor cortex region of the brain of the subject; determining a baseline intensity of stimulation based, at least in part, on the resting motor threshold; and adjusting the baseline intensity of stimulation based, at least in part, on the determined personalized stimulation parameters.

Embodiment 75. The method of embodiment 72, wherein the brain region is part of a brain network, and the brain network is one or more of the Fronto-Parietal control Network, the Sensorimotor Network, the Anterior Salience Network, the Dorsal Attention Network, the Ventral Attention Network, the Visual Network, the Auditory Network, or the Language Network.

Embodiment 76. The method of embodiment 72, wherein the brain region is part of the DMN Embodiment 77. The method of embodiment 72, wherein brain region is the Precuneus Embodiment 78. The method of embodiment 72, wherein the plurality of evoked potentials in response to stimulation is obtained via concurrent TMS-EEG recording.

Embodiment 79. The method of embodiment 72, wherein providing non-invasive stimulation comprises providing at least one of transcranial electrical stimulation or transcranial magnetic stimulation to the determined location of stimulation of the brain of the subject.

Embodiment 80. The method of embodiment 72, wherein the plurality of locations are arranged in a grid.

Embodiment 81. The method of embodiment 72, wherein the one or more stimulation characteristics comprises a peak magnitude of the plurality of evoked potentials.

Embodiment 82. The method of embodiment 72, wherein determining the personalized stimulation parameters comprises selecting a location from the plurality of locations having a largest peak magnitude of the plurality of evoked potentials.

Embodiment 83. The method of embodiment 72, wherein sensing the plurality of evoked potentials comprises sensing the plurality of evoked potentials using electroencephalography.

Embodiment 84. The method of embodiment 72, further comprising: treat or ameliorate a neurological or psychiatric disease by providing the non-invasive stimulation to the determined location of stimulation according to the determined personalized stimulation parameters.

Embodiment 85. The method of embodiment 84, wherein the neurological or psychiatric disease is Alzheimer's Disease.

Embodiment 86. The method of embodiment 84, wherein the neurological or psychiatric disease is Mild Cognitive Impairment (MCI).

Embodiment 87. The method of embodiment 84, wherein the neurological or psychiatric disease is Frontotemporal Dementia.

Embodiment 88. The method of embodiment 84, wherein the neurological or psychiatric disease is characterized by alterations of brain networks, such as Depression (DEP), Schizophrenia (SCZ), Autism (AUT), Attention Deficit & Hyperactivity Disorder (ADHD), Bipolar disorder (BP), amyotrophic lateral sclerosis (ALS), Parkinson's disease (PD), traumatic brain injury (TBI), Insomnia (INS), Disorder of Consciousness (DOC), headache (HD), multiple sclerosis (MS), Stroke (STR), and brain tumors (BT).

Embodiment 89. The method of embodiment 84, wherein the neurological or psychiatric disease is characterized by memory deficits.

Embodiment 90. The method of embodiment 84, wherein the neurological or psychiatric disease is characterized by deficits in cognitive control.

Embodiment 91. The method of embodiment 84, wherein the neurological or psychiatric disease is characterized by decrease of functional independence.

Embodiment 92. The method of embodiment 84, wherein the non-invasive stimulation provided according to the personalized stimulation parameters is combined with a drug intervention affecting the central nervous system, delivered sequentially or simultaneously.

Embodiment 93. The method of embodiment 84, wherein the non-invasive stimulation provided according to the personalized stimulation parameters is combined with a cognitive assessment, cognitive training or cognitive enhancement intervention, delivered sequentially or simultaneously.

Embodiment 94. The method of embodiment 84, wherein the non-invasive stimulation provided according to the personalized stimulation parameters is combined with a behavioral intervention, delivered sequentially or simultaneously.

Embodiment 95. The method of embodiment 84, wherein the non-invasive stimulation provided according to the personalized stimulation parameters is combined with a different non-invasive stimulation intervention, delivered sequentially or simultaneously, including transcranial electrical stimulation.

Embodiment 96. The method of embodiment 72, wherein the brain region comprises at least a portion of the angular gyrus.

Embodiment 97. The method of embodiment 72, wherein the brain region comprises at least a portion of the temporal lobe.

Embodiment 98. The method of embodiment 72, wherein the brain region comprises at least a portion of the medial prefrontal cortex.

Embodiment 99. An embodiment comprising a method of determining personalized stimulus characteristics for targeted non-invasive brain stimulation for a brain of a patient, the method comprising: a. sensing a resting motor threshold in response to providing non-invasive stimulation of a motor cortex region of the brain of the patient; b. non-invasively stimulating of a region of the brain outside of the motor cortex region; c. sensing an evoked potential in response to the stimulation of the region of the brain outside of the motor cortex region; and d. adjusting the resting motor threshold of stimulation based, at least in part, on at least one characteristic of the sensed evoked potential.

Embodiment 100. The method of embodiment 99, wherein the region outside the motor cortex is part of the DMN.

Embodiment 101. The method of embodiment 99, wherein the region outside the motor cortex is the Precuneus.

Embodiment 102. The method of embodiment 99, wherein the evoked potential in response to stimulation is obtained via concurrent TMS-EEG recording.

Embodiment 103. The method of embodiment 99, wherein the characteristic of the evoked potential is signal amplitude.

Embodiment 104. The method of embodiment 99, wherein one of the characteristics of the evoked potential is a stimulation intensity, and the stimulation intensity is adjusted based on biophysical modeling work simulating the electrical field generated in a target region for the patient.

Embodiment 105. The method of embodiment 99, wherein non-invasively stimulating comprises providing at least one of transcranial electrical stimulation or transcranial magnetic stimulation to a location of the brain of the patient.

Embodiment 106. The method of embodiment 99, wherein the at least one characteristic comprises a peak magnitude of the evoked potential.

Embodiment 107. The method of embodiment 99, wherein sensing the evoked potential comprises sensing the evoked potential using electroencephalography.

Embodiment 108. The method of embodiment 99, further comprising selecting a personalized stimulation target by selecting a location of a plurality of locations having a largest peak magnitude of the at least one evoked potential.

Embodiment 109. The method of embodiment 108, further comprising treating or ameliorating a neurological or psychiatric disease by providing the non-invasive stimulation Embodiment 110. The method of embodiment 109, wherein the neurological or psychiatric disease is Alzheimer's Disease.

Embodiment 111. The method of embodiment 109, wherein the neurological or psychiatric disease is Mild Cognitive Impairment (MCI).

Embodiment 112. The method of embodiment 109, wherein the neurological or psychiatric disease is Frontotemporal Dementia.

Embodiment 113. The method of embodiment 109, wherein the neurological or psychiatric disease is characterized by alterations of brain networks, such as Depression (DEP), Schizophrenia (SCZ), Autism (AUT), Attention Deficit & Hyperactivity Disorder (ADHD), Bipolar disorder (BP), amyotrophic lateral sclerosis (ALS), Parkinson's disease (PD), traumatic brain injury (TBI), Insomnia (INS), Disorder of Consciousness (DOC), headache (HD), multiple sclerosis (MS), Stroke (STR), brain tumors (BT).

Embodiment 114. The method of embodiment 109, wherein the neurological or psychiatric disease is characterized by memory deficits.

Embodiment 115. The method of embodiment 109, wherein the neurological or psychiatric disease is characterized by deficits in cognitive control.

Embodiment 116. The method of embodiment 109, wherein the neurological or psychiatric disease is characterized by decrease of functional independence.

Embodiment 117. The method of embodiment 109, wherein the non-invasive stimulation is combined with a drug intervention affecting the central nervous system, delivered sequentially or simultaneously.

Embodiment 118. The method of embodiment 109, wherein the non-invasive stimulation is combined with one or more of a cognitive assessment, cognitive training, or cognitive enhancement intervention, delivered sequentially or simultaneously.

Embodiment 119. The method of embodiment 109, wherein the non-invasive stimulation is combined with a behavioral intervention, delivered sequentially or simultaneously.

Embodiment 120. The method of embodiment 109, wherein the non-invasive stimulation is combined with a different non-invasive stimulation intervention, delivered sequentially or simultaneously, including transcranial electrical stimulation.

Embodiment 121. An embodiment comprising a method of treating or ameliorating a neurological or psychiatric disease in a subject, the method comprising: a. non-invasively stimulating a first location in a first brain region of a plurality of brain regions identified as forming a brain network, b. wherein the first location is a sub-region of the first brain region strongly connected to one or more other brain regions of the plurality of brain regions.

Embodiment 122. The method of embodiment 121, wherein the plurality of brain regions forming the brain network is identified based on scan data of the brain of the subject.

Embodiment 123. The method of embodiment 121, wherein the first brain region is part of a Default Mode Network (DMN).

Embodiment 124. The method of embodiment 121, wherein the first brain region comprises at least a portion of the precuneus.

Embodiment 125. The method of embodiment 121, wherein the neurological or psychiatric disease is Alzheimer's Disease.

Embodiment 126. The method of embodiment 121, wherein providing non-invasive stimulation comprises providing at least one of transcranial electrical stimulation or transcranial magnetic stimulation to the first location of the brain of a patient.

Embodiment 127. The method of embodiment 121, further comprising: treating or ameliorating the neurological or psychiatric disease by providing the non-invasive stimulation to the first location.

Embodiment 128. The method of embodiment 121, wherein the brain network is one or more of the Fronto-Parietal control Network, the Sensorimotor Network, the Anterior Salience Network, the Dorsal Attention Network, the Ventral Attention Network, the Visual Network, the Auditory Network, or the Language Network.

Embodiment 129. The method of embodiment 121, wherein the first location comprises at least a portion of the angular gyrus.

Embodiment 130. The method of embodiment 121, wherein the first location comprises at least a portion of the temporal lobe.

Embodiment 131. The method of embodiment 121, wherein the first location comprises at least a portion of the medial prefrontal cortex.

Embodiment 132. The method of embodiment 121, wherein the neurological or psychiatric disease is Mild Cognitive Impairment (MCI).

Embodiment 133. The method of embodiment 121, wherein the neurological or psychiatric disease is Frontotemporal Dementia.

Embodiment 134. The method of embodiment 121, wherein the neurological or psychiatric disease is characterized by alterations of brain networks, such as Depression (DEP), Schizophrenia (SCZ), Autism (AUT), Attention Deficit & Hyperactivity Disorder (ADHD), Bipolar disorder (BP), amyotrophic lateral sclerosis (ALS), Parkinson's disease (PD), traumatic brain injury (TBI), Insomnia (INS), Disorder of Consciousness (DOC), headache (HD), multiple sclerosis (MS), Stroke (STR), and brain tumors (BT).

Embodiment 135. The method of embodiment 121, wherein the neurological or psychiatric disease is characterized by memory deficits.

Embodiment 136. The method of embodiment 121, wherein the neurological or psychiatric disease is characterized by deficits in cognitive control.

Embodiment 137. The method of embodiment 121, wherein the neurological or psychiatric disease is characterized by decrease of functional independence.

Embodiment 138. The method of embodiment 121, wherein the non-invasive stimulation provided to the first location is combined with a drug intervention affecting the central nervous system, delivered sequentially or simultaneously.

Embodiment 139. The method of embodiment 121, wherein the non-invasive stimulation provided to the first location is combined with a cognitive assessment, cognitive training or cognitive enhancement intervention, delivered sequentially or simultaneously.

Embodiment 140. The method of embodiment 121, wherein the non-invasive stimulation provided to the first location is combined with a behavioral intervention, delivered sequentially or simultaneously.

Embodiment 141. The method of embodiment 121, wherein the non-invasive stimulation provided to the first location is combined with a different non-invasive stimulation intervention, delivered sequentially or simultaneously, including transcranial electrical stimulation.

Embodiment 142. An embodiment comprising a method of determining personalized stimulus characteristics for targeted non-invasive brain stimulation for a subject, the method comprising: a. non-invasively stimulating of a region of the brain; b. estimating the electrical field induced by stimulation in a region of the brain; and c. adjusting the stimulus characteristics based, at least in part, on at least one characteristic of the induced electric field.

Embodiment 143. The method of embodiment 142, wherein an intensity of the induced electric field is used to adjust one or more of stimulation intensity, frequency, pulse shape, of duration.

Embodiment 144. The method of embodiment 142, wherein the region of the brain is part of a Default Mode Network (DMN).

Embodiment 145. The method of embodiment 142, wherein the region of the brain comprises at least a portion of the precuneus.

Embodiment 146. The method of embodiment 142, wherein non-invasive stimulating of the region of the brain comprises providing at least one of transcranial electrical stimulation or transcranial magnetic stimulation according to the stimulus characteristics.

Embodiment 147. The method of any of embodiment 142 to embodiment 146, further comprising: treating or ameliorating a neurological or psychiatric disease by providing the non-invasive stimulation according to the stimulus characteristics.

Embodiment 148. The method of embodiment 142, further comprising identifying a plurality of brain regions forming a brain network based on scan data of the brain of the subject, and wherein the region of the brain non-invasively stimulated is a brain region of the brain network.

Embodiment 149. The method of embodiment 148, wherein the brain network is one or more of the Fronto-Parietal control Network, the Sensorimotor Network, the Anterior Salience Network, the Dorsal Attention Network, the Ventral Attention Network, the Visual Network, the Auditory Network, or the Language Network.

Embodiment 150. The method of embodiment 148, wherein the brain region comprises at least a portion of the angular gyms.

Embodiment 151. The method of embodiment 148, wherein the brain region comprises at least a portion of the temporal lobe.

Embodiment 152. The method of embodiment 148, wherein the brain region comprises at least a portion of the medial prefrontal cortex.

Embodiment 153. The method of embodiment 147, wherein the neurological or psychiatric disease is Alzheimer's Disease.

Embodiment 154. The method of embodiment 147, wherein the neurological or psychiatric disease is Mild Cognitive Impairment (MCI).

Embodiment 155. The method of embodiment 147, wherein the neurological or psychiatric disease is Fronto-temporal Dementia.

Embodiment 156. The method of embodiment 147, wherein the neurological or psychiatric disease is characterized by alterations of brain networks, such as Depression (DEP), Schizophrenia (SCZ), Autism (AUT), Attention Deficit & Hyperactivity Disorder (ADHD), Bipolar disorder (BP), amyotrophic lateral sclerosis (ALS), Parkinson's disease (PD), traumatic brain injury (TBI), Insomnia (INS), Disorder of Consciousness (DOC), headache (HD), multiple sclerosis (MS), Stroke (STR), and brain tumors (BT).

Embodiment 157. The method of embodiment 147, wherein the neurological or psychiatric disease is characterized by memory deficits.

Embodiment 158. The method of embodiment 147, wherein the neurological or psychiatric disease is characterized by deficits in cognitive control.

Embodiment 159. The method of embodiment 147, wherein the neurological or psychiatric disease is characterized by decrease of functional independence.

Embodiment 160. The method of embodiment 147, wherein the non-invasive stimulation provided according to the stimulus characteristics is combined with a drug intervention affecting the central nervous system, delivered sequentially or simultaneously.

Embodiment 161. The method of embodiment 147, wherein the non-invasive stimulation provided according to the stimulus characteristics is combined with a cognitive assessment, cognitive training or cognitive enhancement intervention, delivered sequentially or simultaneously.

Embodiment 162. The method of embodiment 147, wherein the non-invasive stimulation provided according to the stimulus characteristics is combined with a behavioral intervention, delivered sequentially or simultaneously.

Embodiment 163. The method of embodiment 147, wherein the non-invasive stimulation provided according to the stimulus characteristics is combined with a different non-invasive stimulation intervention, delivered sequentially or simultaneously, including transcranial electrical stimulation.

Embodiment 164. An embodiment comprising a system for identifying a first location in a brain of a subject suitable for non-invasive stimulation to treat or ameliorate a neurological or psychiatric disease, the system comprising: a. an imaging source configured to generate scan data of the brain of the subject; and b. a processor configured to: (i) identify from the scan data a plurality of brain regions forming a brain network, and (ii) determine, within a first brain region of the plurality of brain regions, as the first location suitable for non-invasive stimulation, a sub-region of the first brain region strongly connected to one or more other brain regions of the plurality of brain regions.

Embodiment 165. The system of embodiment 164, further comprising a stimulation device for providing non-invasive stimulation to at least the first location of the brain of the subject.

Embodiment 166. The system of embodiment 164, wherein the imaging source is Magnetic Resonance Imaging (MRI)

Embodiment 167. The system of embodiment 164, wherein the scan data is diffusion MRI data;

Embodiment 168. The system of embodiment 164, wherein the scan data is perfusion MRI data;

Embodiment 169. The system of embodiment 164, wherein the scan data is PET data indexing local perfusion/metabolic levels or indexing protein burden or measuring neuroinflammation;

Embodiment 170. The system of embodiment 164, wherein the scan data comprises neuroimaging data for a plurality of subjects having a neurological disease.

Embodiment 171. The system of embodiment 164, wherein the scan data comprises neuroimaging data.

Embodiment 172. The system of embodiment 164, wherein the processor is configured to identify the brain network based on one or more of a brain connectomics, network theory, graph theory, or control theory analysis framework.

Embodiment 173. The system of embodiment 164, wherein the processor is further configured to: cause the neurological or psychiatric disease to be treated by providing the non-invasive stimulation to the determined first location.

Embodiment 174. The system of embodiment 164, wherein the brain network is one or more of the Fronto-Parietal control Network, the Sensorimotor Network, the Anterior Salience Network, the Dorsal Attention Network, the Ventral Attention Network, the Visual Network, the Auditory Network, or the Language Network;

Embodiment 175. The system of embodiment 164, wherein the first brain region comprises at least a portion of the precuneus.

Embodiment 176. The system of embodiment 164, wherein the first brain region comprises at least a portion of the angular gyms.

Embodiment 177. The system of embodiment 164, wherein the first brain region comprises at least a portion of the temporal lobe.

Embodiment 178. The system of embodiment 164, wherein the first brain region comprises at least a portion of the medial prefrontal cortex.

Embodiment 179. The system of embodiment 164, wherein the neurological or psychiatric disease is Alzheimer's Disease.

Embodiment 180. The system of embodiment 164, wherein the neurological or psychiatric disease is Mild Cognitive Impairment (MCI).

Embodiment 181. The system of embodiment 164, wherein the neurological or psychiatric disease is Frontotemporal Dementia.

Embodiment 182. The system of embodiment 164, wherein the neurological or psychiatric disease is characterized by alterations of brain networks, such as Depression (DEP), Schizophrenia (SCZ), Autism (AUT), Attention Deficit & Hyperactivity Disorder (ADHD), Bipolar disorder (BP), amyotrophic lateral sclerosis (ALS), Parkinson's disease (PD), traumatic brain injury (TBI), Insomnia (INS), Disorder of Consciousness (DOC), headache (HD), multiple sclerosis (MS), Stroke (STR), and brain tumors (BT).

Embodiment 183. The system of embodiment 164, wherein the neurological or psychiatric disease is characterized by memory deficits.

Embodiment 184. The system of embodiment 164, wherein the neurological or psychiatric disease is characterized by deficits in cognitive control.

Embodiment 185. The system of embodiment 164, wherein the neurological or psychiatric disease is characterized by decrease of functional independence.

Embodiment 186. An embodiment comprising a system for determining a personalized stimulation target in a brain region to treat or ameliorate a neurological or psychiatric disease in the subject, the system comprising: a. a stimulation device for providing non-invasive stimulation to each location of a plurality of locations in a brain region of a subject; and b. a sensor device for sensing, in response to the stimulation provided, at least one evoked potential; and c. a processor configured to select as a personalized stimulation target, one of the locations of the plurality of locations that is suitable for providing therapeutically effective non-invasive stimulation to treat or ameliorate the neurological or psychiatric disease, wherein the selection is based on at least one characteristic of the at least one evoked potential.

Embodiment 187. The system of embodiment 186, wherein the brain region is part of a Default Mode Network (DMN).

Embodiment 188. The system of embodiment 186, wherein the brain region comprises at least a portion of the precuneus.

Embodiment 189. The system of embodiment 186, wherein the neurological or psychiatric disease is Alzheimer's Disease.

Embodiment 190. The system of embodiment 186, wherein the stimulation device is configured to provide at least one of transcranial electrical stimulation or transcranial magnetic stimulation to the personalized stimulation target of the brain of the subject.

Embodiment 191. The system of embodiment 186, wherein the plurality of locations are arranged in a grid.

Embodiment 192. The system of embodiment 186, wherein the at least one characteristic comprises a peak magnitude of the at least one evoked potential.

Embodiment 193. The system of embodiment 186, wherein selecting the personalized stimulation target comprises selecting the location of the plurality of locations having a largest peak magnitude of the at least one evoked potential.

Embodiment 194. The system of embodiment 186, wherein the sensor device is configured to sense the at least one evoked potential using electroencephalography.

Embodiment 195. The system of embodiment 186, wherein the stimulation device is configured to treat or ameliorate the neurological or psychiatric disease by providing the non-invasive stimulation to the selected personalized stimulation target.

Embodiment 196. The system of embodiment 186, wherein the brain network is one or more of the Fronto-Parietal control Network, the Sensorimotor Network, the Anterior Salience Network, the Dorsal Attention Network, the Ventral Attention Network, the Visual Network, the Auditory Network, or the Language Network.

Embodiment 197. The system of embodiment 186, wherein the personalized stimulation target is a region of the angular gyrus;

Embodiment 198. The system of embodiment 186, wherein the personalized stimulation target is a region of the temporal lobe;

Embodiment 199. The method of embodiment 186, wherein the personalized stimulation target is a region of the medial prefrontal cortex;

Embodiment 200. The system of embodiment 186, wherein the neurological or psychiatric disease is Mild Cognitive Impairment (MCI).

Embodiment 201. The system of embodiment 186, wherein the neurological or psychiatric disease is Frontotemporal Dementia.

Embodiment 202. The system of embodiment 186, wherein the neurological or psychiatric disease is characterized by alterations of brain networks, such as Depression (DEP), Schizophrenia (SCZ), Autism (AUT), Attention Deficit & Hyperactivity Disorder (ADHD), Bipolar disorder (BP), amyotrophic lateral sclerosis (ALS), Parkinson's disease (PD), traumatic brain injury (TBI), Insomnia (INS), Disorder of Consciousness (DOC), headache (HD), multiple sclerosis (MS), Stroke (STR), and brain tumors (BT).

Embodiment 203. The system of embodiment 186, wherein the neurological or psychiatric disease is characterized by memory deficits.

Embodiment 204. The system of embodiment 186, wherein the neurological or psychiatric disease is characterized by deficits in cognitive control.

Embodiment 205. The system of embodiment 186, wherein the neurological or psychiatric disease is characterized by decrease of functional independence.

Embodiment 206. The system of embodiment 186, wherein the non-invasive stimulation provided to the selected personalized stimulation target is combined with a drug intervention affecting the central nervous system, delivered sequentially or simultaneously.

Embodiment 207. The system of embodiment 186, wherein the non-invasive stimulation provided to the selected personalized stimulation target is combined with one or more of a cognitive assessment, cognitive training, or cognitive enhancement intervention, delivered sequentially or simultaneously.

Embodiment 208. The system of embodiment 186, wherein the non-invasive stimulation provided to the selected personalized stimulation target is combined with a behavioral intervention, delivered sequentially or simultaneously.

Embodiment 209. The system of embodiment 186, wherein the non-invasive stimulation provided to the selected personalized stimulation target is combined with a different non-invasive stimulation intervention, delivered sequentially or simultaneously, including transcranial electrical stimulation.

Embodiment 210. The system of embodiment 186, wherein the processor elaborates a sequence of combined automated and semiautomated signal processing algorithms installed on a local hardware, resulting in a specific indication for, but not limited to, stimulation location, frequency, intensity.

Embodiment 211. The system of embodiment 186, wherein the processor elaborates a sequence of combined automated and semiautomated signal processing algorithms installed on remote hardware with connectivity capabilities, resulting in a specific indication for, but not limited to, stimulation location, frequency, intensity.

Embodiment 212. The system of embodiment 186, wherein the data collected from individuals receiving the TMS-based intervention are stored for group-level inference and to further optimize the TMS optimization procedures, wherein the collected data may be used to, but not limited to, identify clusters of patients with similar response to treatment, refine dose estimation procedures, build machine learning and artificial intelligence models of response to treatment, and prediction of disease progression.

Embodiment 213. An embodiment comprising a system for determining parameters for non-invasive stimulation of a brain of a patient, the system comprising: a. a sensor device for sensing a plurality of evoked potentials in response to non-invasive stimulation of each location of a plurality of locations in a brain region of a patient; and b. a processor configured to determine, based at least in part, on at least one characteristic of the plurality of evoked potentials, personalized stimulation parameters for the patient, wherein the personalized stimulation parameters include a location of stimulation and one or more stimulation characteristics.

Embodiment 214. The system of embodiment 213, wherein the one or more stimulation characteristics include an intensity of stimulation and/or a frequency of stimulation.

Embodiment 215. The system of embodiment 213, wherein the sensor device is further configured to sense a resting motor threshold in response to providing non-invasive stimulation of a motor cortex region of the brain of the patient, wherein the processor is further configured to determine a baseline intensity of stimulation based, at least in part, on the resting motor threshold; and wherein the processor is further configured to adjust the baseline intensity of stimulation based, at least in part, on the determined personalized stimulation parameters.

Embodiment 216. The system of embodiment 213, wherein the brain region is part of a brain network.

Embodiment 217. The system of embodiment 213, wherein the brain region is part of the DMN.

Embodiment 218. The system of embodiment 213, wherein brain region is the Precuneus.

Embodiment 219. The system of embodiment 213, wherein the plurality of evoked potentials in response to stimulation is obtained via concurrent TMS-EEG recording.

Embodiment 220. The system of embodiment 213, further comprising a stimulation device to provide non-invasive stimulation to the subject based on the personalized stimulation parameters by providing at least one of transcranial electrical stimulation or transcranial magnetic stimulation to the determined location of stimulation of the brain of the patient.

Embodiment 221. The system of embodiment 213, wherein the plurality of locations are arranged in a grid.

Embodiment 222. The system of embodiment 213, wherein the one or more stimulation characteristic comprises a peak magnitude of the plurality of evoked potentials.

Embodiment 223. The system of embodiment 213, wherein the processor is configured to determine the personalized stimulation parameters by selecting a location from the plurality of locations having a largest peak magnitude of the plurality of evoked potentials.

Embodiment 224. The system of embodiment 213, wherein the sensor device is configured to sense the plurality of evoked potentials using electroencephalography.

Embodiment 225. The system of embodiment 213, wherein the brain region is a location of a brain network, and wherein the brain network is one or more of the Fronto-Parietal control Network, the Sensorimotor Network, the Anterior Salience Network, the Dorsal Attention Network, the Ventral Attention Network, the Visual Network, the Auditory Network, the Language Network;

Embodiment 226. The system of embodiment 213, wherein the brain region comprises at least a portion of the angular gyms;

Embodiment 227. The system of embodiment 213, wherein the brain region comprises at least a portion of the temporal lobe;

Embodiment 228. The system of embodiment 213, wherein the brain region comprises at least a portion of the medial prefrontal cortex;

Embodiment 229. The system of embodiment 213, further comprising: a stimulation device to treat or ameliorate a neurological or psychiatric disease by providing the non-invasive stimulation to the determined location of stimulation according to the determined personalized stimulation parameters.

Embodiment 230. The system of embodiment 229, wherein the neurological or psychiatric disease is Alzheimer's Disease.

Embodiment 231. The system of embodiment 229, wherein the neurological or psychiatric disease is Mild Cognitive Impairment (MCI).

Embodiment 232. The system of embodiment 229, wherein the neurological or psychiatric disease is Fronto-temporal Dementia.

Embodiment 233. The system of embodiment 229, wherein the neurological or psychiatric disease is characterized by alterations of brain networks, such as Depression (DEP), Schizophrenia (SCZ), Autism (AUT), Attention Deficit & Hyperactivity Disorder (ADHD), Bipolar disorder (BP), amyotrophic lateral sclerosis (ALS), Parkinson's disease (PD), traumatic brain injury (TBI), Insomnia (INS), Disorder of Consciousness (DOC), headache (HD), multiple sclerosis (MS), Stroke (STR), and brain tumors (BT).

Embodiment 234. The system of embodiment 229, wherein the neurological or psychiatric disease is characterized by memory deficits.

Embodiment 235. The system of embodiment 229, wherein the neurological or psychiatric disease is characterized by deficits in cognitive control.

Embodiment 236. The system of embodiment 229, wherein the neurological or psychiatric disease is characterized by decrease of functional independence.

Embodiment 237. The system of embodiment 229, wherein the non-invasive stimulation provided according to the personalized stimulation parameters is combined with a drug intervention affecting the central nervous system, delivered sequentially or simultaneously.

Embodiment 238. The system of embodiment 229, wherein the non-invasive stimulation provided according to the personalized stimulation parameters is combined with a cognitive assessment, cognitive training or cognitive enhancement intervention, delivered sequentially or simultaneously.

Embodiment 239. The system of embodiment 213, wherein the non-invasive stimulation provided according to the personalized stimulation parameters is combined with a behavioral intervention, delivered sequentially or simultaneously.

Embodiment 240. The system of embodiment 213, wherein the non-invasive stimulation according to the personalized stimulation parameters is combined with a different non-invasive stimulation intervention, delivered sequentially or simultaneously, including transcranial electrical stimulation.

Embodiment 241. An embodiment comprising a system for determining personalized stimulus characteristics for targeted non-invasive brain stimulation for a brain of a patient, the system comprising: a. a sensor device for sensing a resting motor threshold in response to providing non-invasive stimulation of a motor cortex region of the brain of the patient; and b. a stimulation device for non-invasively stimulating of a region of the brain outside of the motor cortex region; c. wherein the sensor device is further configured to sense an evoked potential in response to the stimulation of the region of the brain outside of the motor cortex region; and d. wherein the stimulation device is configured to adjust the resting motor threshold of stimulation based, at least in part, on at least one characteristic of the sensed evoked potential.

Embodiment 242. The system of embodiment 241, wherein the region outside the motor cortex is part of the DMN.

Embodiment 243. The system of embodiment 241, wherein the region outside the motor cortex is the Precuneus.

Embodiment 244. The system of embodiment 241, wherein the evoked potential in response to stimulation is obtained via concurrent TMS-EEG recording;

Embodiment 245. The system of embodiment 241, wherein the characteristic of the evoked potential is signal amplitude;

Embodiment 246. The system of embodiment 241, wherein one of the characteristics of the evoked potential is a stimulation intensity, and the stimulation intensity is adjusted based on biophysical modeling work simulating the electrical field generated in a target region for the patient;

Embodiment 247. The system of embodiment 241, wherein the stimulation device is configured to provide at least one of transcranial electrical stimulation or transcranial magnetic stimulation to a location of the brain of the patient.

Embodiment 248. The system of embodiment 241, wherein the plurality of locations are arranged in a grid.

Embodiment 249. The system of embodiment 241, wherein the at least one characteristic comprises a peak magnitude of the at least one evoked potential.

Embodiment 250. The system of embodiment 241, wherein selecting the personalized stimulation target comprises selecting the location of the plurality of locations having a largest peak magnitude of the at least one evoked potential.

Embodiment 251. The system of embodiment 241, wherein the sensor device is configured to sense the at least one evoked potential using electroencephalography.

Embodiment 252. The system of embodiment 241, the stimulation device is configured to treat or ameliorate a neurological or psychiatric disease by providing the non-invasive stimulation to a personalized stimulation target.

Embodiment 253. The system of embodiment 252, wherein the neurological or psychiatric disease is Alzheimer's Disease.

Embodiment 254. The system of embodiment 252, wherein the neurological or psychiatric disease is Mild Cognitive Impairment (MCI).

Embodiment 255. The system of embodiment 252, wherein the neurological or psychiatric disease is Alzheimer's Disease.

Embodiment 256. The system of embodiment 252, wherein the neurological or psychiatric disease is characterized by alterations of brain networks, such as Depression (DEP), Schizophrenia (SCZ), Autism (AUT), Attention Deficit & Hyperactivity Disorder (ADHD), Bipolar disorder (BP), amyotrophic lateral sclerosis (ALS), Parkinson's disease (PD), traumatic brain injury (TBI), Insomnia (INS), Disorder of Consciousness (DOC), headache (HD), multiple sclerosis (MS), Stroke (STR), and brain tumors (BT).

Embodiment 257. The system of embodiment 252, wherein the neurological or psychiatric disease is characterized by memory deficits.

Embodiment 258. The system of embodiment 252, wherein the neurological or psychiatric disease is characterized by deficits in cognitive control.

Embodiment 259. The system of embodiment 252, wherein the neurological or psychiatric disease is characterized by decrease of functional independence.

Embodiment 260. The system of embodiment 252, wherein the non-invasive stimulation provided to the determined personalized stimulation target is combined with a drug intervention affecting the central nervous system, delivered sequentially or simultaneously.

Embodiment 261. The system of embodiment 252, wherein the non-invasive stimulation provided to the determined personalized stimulation target is combined with a cognitive assessment, cognitive training or cognitive enhancement intervention, delivered sequentially or simultaneously.

Embodiment 262. The system of embodiment 252, wherein the non-invasive stimulation provided to the determined personalized stimulation target is combined with a behavioral intervention, delivered sequentially or simultaneously.

Embodiment 263. The system of embodiment 252, wherein the non-invasive stimulation provided to the determined personalized stimulation target is combined with a different non-invasive stimulation intervention, delivered sequentially or simultaneously, including transcranial electrical stimulation.

Embodiment 264. An embodiment comprising a system for treating or ameliorating a neurological or psychiatric disease in a subject, the system comprising: a. a stimulation device for non-invasively stimulating a first location in a first brain region of a plurality of brain regions identified as forming a functional brain network, b. wherein the first location is a sub-region of the first brain region strongly connected to one or more other brain regions of the plurality of brain regions.

Embodiment 265. The system of embodiment 264, wherein the plurality of brain regions forming the brain network is identified based on scan data of the brain of the subject.

Embodiment 266. The system of embodiment 264, wherein the brain region is part of a Default ode Network (DMN).

Embodiment 267. The system of embodiment 264, wherein the first brain region comprises at least a portion of the precuneus.

Embodiment 268. The system of embodiment 264, wherein the neurological or psychiatric disease is Alzheimer's Disease.

Embodiment 269. The system of embodiment 264, wherein the non-invasive stimulation comprises at least one of transcranial electrical stimulation or transcranial magnetic stimulation to the first location of the brain of a patient.

Embodiment 270. The system of embodiment 264, further comprising a stimulation device to treat or ameliorate the neurological or psychiatric disease by providing the non-invasive stimulation to the first location.

Embodiment 271. The system of embodiment 264, wherein the brain network is one or more of the Fronto-Parietal control Network, the Sensorimotor Network, the Anterior Salience Network, the Dorsal Attention Network, the Ventral Attention Network, the Visual Network, the Auditory Network, or the Language Network.

Embodiment 272. The system of embodiment 264, wherein the first location comprises at least a portion of the angular gyms.

Embodiment 273. The system of embodiment 264, wherein the first location comprises at least a portion of the temporal lobe.

Embodiment 274. The system of embodiment 264, wherein the first location comprises at least a portion of the medial prefrontal cortex.

Embodiment 275. The system of embodiment 264, wherein the neurological or psychiatric disease is Mild Cognitive Impairment (MCI).

Embodiment 276. The system of embodiment 264, wherein the neurological or psychiatric disease is Fronto-temporal Dementia.

Embodiment 277. The system of embodiment 264, wherein the neurological or psychiatric disease is characterized by alterations of brain networks, such as Depression (DEP), Schizophrenia (SCZ), Autism (AUT), Attention Deficit & Hyperactivity Disorder (ADHD), Bipolar disorder (BP), amyotrophic lateral sclerosis (ALS), Parkinson's disease (PD), traumatic brain injury (TBI), Insomnia (INS), Disorder of Consciousness (DOC), headache (HD), multiple sclerosis (MS), Stroke (STR), and brain tumors (BT).

Embodiment 278. The system of any of embodiments 264, wherein the neurological or psychiatric disease is characterized by memory deficits.

Embodiment 279. The system of embodiment 264, wherein the neurological or psychiatric disease is characterized by deficits in cognitive control.

Embodiment 280. The system of embodiment 264, wherein the neurological or psychiatric disease is characterized by decrease of functional independence.

Embodiment 281. The system of embodiment 264, wherein the non-invasive stimulation provided to the first location is combined with a drug intervention affecting the central nervous system, delivered sequentially or simultaneously.

Embodiment 282. The system of embodiment 264, wherein the non-invasive stimulation provided to the first location is combined with a cognitive assessment, cognitive training or cognitive enhancement intervention, delivered sequentially or simultaneously.

Embodiment 283. The system of embodiment 264, wherein the non-invasive stimulation provided to the first location is combined with a behavioral intervention, delivered sequentially or simultaneously.

Embodiment 284. The system of embodiment 264, wherein the non-invasive stimulation provided to the first location vis combined with a different non-invasive stimulation intervention, delivered sequentially or simultaneously, including transcranial electrical stimulation.

Embodiment 285. An embodiment comprising a system for administering a brain stimulation therapy to treat or ameliorate a neurological or psychiatric disease, the system comprising: a. a data collection platform to collect and store data of a subject used for identifying an optimal stimulation target; b. a data analysis platform to process the data of the subject and derive optimal stimulation parameters for treatment; and c. an infrastructure for scheduling brain stimulation sessions and monitoring the treatment; and d. a database including the data of the subject collected before and/or during the treatment.

Embodiment 286. The system of embodiment 285, wherein the data collection platform for identifying optimal brain stimulation parameters for the subject utilizes those described in embodiments 1-163.

Embodiment 287. The system of embodiment 285, wherein the system is accessible to a clinician prescribing the brain stimulation treatment.

Embodiment 288. The system of embodiment 285, wherein the data processing is performed on a local system.

Embodiment 289. The system of embodiment 285, wherein the data processing is performed using cloud-based computing.

Embodiment 290. The system of embodiment 285, wherein the system is connected to a billing software.

Embodiment 291. The system of embodiment 285, wherein the system is connected to a health insurance provider.

Embodiment 292. An embodiment comprising a method for delivering a combined simultaneous noninvasive brain stimulation intervention to a brain region of a subject to treat or ameliorate a neurological or psychiatric disease, the method comprising: a. scanning a brain of a subject; b. identifying a target for noninvasive brain stimulation; wherein the noninvasive brain stimulation is based on transcranial magnetic stimulation technique or transcranial electrical stimulation technique.

Embodiment 293. The method of embodiment 292, wherein the transcranial magnetic stimulation technique is theta burst stimulation.

Embodiment 294. The method of embodiment 292, wherein the transcranial magnetic stimulation technique is repetitive transcranial magnetic stimulation.

Embodiment 295. The method of embodiment 292, wherein the transcranial electrical stimulation technique is transcranial alternating current stimulation.

Embodiment 296. The method of claim M4, wherein the frequency of transcranial alternating current stimulation is within the gamma frequency EEG band.

Embodiment 297. The method of embodiment 292, wherein the identifying a target for noninvasive brain stimulation for a subject are those described in embodiments 1-163.

Embodiment 298. The method of embodiment 292, wherein the transcranial magnetic stimulation technique is theta burst stimulation, the transcranial electrical stimulation technique is transcranial alternating current stimulation, and the transcranial magnetic stimulation and the transcranial electrical stimulation are delivered simultaneously.

Embodiment 299. The method of embodiment 292, wherein the transcranial magnetic stimulation technique is repetitive transcranial magnetic stimulation, the transcranial electrical stimulation technique is transcranial alternating current stimulation, and the transcranial magnetic stimulation and the transcranial electrical stimulation are delivered simultaneously.

Embodiment 300. The method of embodiment 292, wherein the combined simultaneous noninvasive brain stimulation intervention induces an increase in cortical plasticity levels.

Embodiment 301. The method of embodiment 292, wherein the target is a brain network.

Embodiment 302. The method of claim M10, wherein the brain network is a Default Mode Network (DMN).

Embodiment 303. The method of embodiment 292, wherein the brain region comprises at least a portion of the precuneus.

Embodiment 304. The method of embodiment 292, wherein the brain region comprises at least a portion of the dorsolateral prefrontal cortex.

Embodiment 305. The method of embodiment 292, wherein the brain region comprises at least a portion of the parietal lobe.

Embodiment 306. The method of embodiment 292, wherein the brain region comprises at least a portion of the temporal lobe.

Embodiment 307. The method of embodiment 292, wherein the brain region comprises at least a portion of the angular gyms.

Embodiment 308. The method of embodiment 292, wherein the combined non-invasive stimulation provided to the determined stimulation target is effective so that the subject has an increase in the amplitude of TEPs at least 15% bigger compared to that of an untreated subject after a single stimulation session.

Embodiment 309. The method of embodiment 292, wherein the combined non-invasive stimulation provided to the determined stimulation target is effective so that the subject has an increase in the amplitude of network oscillatory at least 15% bigger compared to that of an untreated subject after a single stimulation session.

Embodiment 310. The method of embodiment 292, wherein the combined non-invasive stimulation provided to the determined stimulation target is effective so that the subject has an increase in level of cortical plasticity measured via TEPs at least 15% bigger compared to that of an untreated subject after a single stimulation session.

Embodiment 311. The method of embodiment 292, wherein the combined non-invasive stimulation provided to the determined stimulation target is effective so that the subject has an increase in the frequency of oscillatory brain activity at least 15% bigger compared to that of an untreated subject after a single stimulation session.

Embodiment 312. The method of embodiment 292, wherein the combined non-invasive stimulation provided to the determined stimulation target is delivered over multiple consecutive days, multiple non-consecutive days with a frequency of daily, once a week, or a combination thereof.

Embodiment 313. The method of embodiment 292, wherein the brain network comprises one or more of the Fronto-Parietal control Network, the Sensorimotor Network, the Anterior Salience Network, the Dorsal Attention Network, the Ventral Attention Network, the Visual Network, the Auditory Network, or the Language Network.

Embodiment 314. The method of embodiment 292, wherein the neurological or psychiatric disease is Alzheimer's Disease.

Embodiment 315. The method of embodiment 292, wherein the neurological or psychiatric disease is Mild Cognitive Impairment (MCI).

Embodiment 316. The method of embodiment 292, wherein the neurological or psychiatric disease is Fronto-temporal Dementia.

Embodiment 317. The method of embodiment 292, wherein the neurological or psychiatric disease is characterized by alterations of brain networks, such as Depression (DEP), Schizophrenia (SCZ), Autism (AUT), Attention Deficit & Hyperactivity Disorder (ADHD), Bipolar disorder (BP), amyotrophic lateral sclerosis (ALS), Parkinson's disease (PD), traumatic brain injury (TBI), Insomnia (INS), Disorder of Consciousness (DOC), headache (HD), multiple sclerosis (MS), Stroke (STR), and brain tumors (BT).

Embodiment 318. The method of embodiment 292, wherein the neurological or psychiatric disease is characterized by memory deficits.

Embodiment 319. The method of embodiment 292, wherein the neurological or psychiatric disease is characterized by deficits in cognitive control.

Embodiment 320. The method of embodiment 292, wherein the neurological or psychiatric disease is characterized by decrease of functional independence.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for determining personalized stimulation parameters for non-invasive stimulation of a brain of a subject, the method comprising:

sequentially stimulating using transcranial magnetic stimulation (TMS), each of a plurality of locations within a brain region of the subject, the brain region forming a node of a functional brain network of connected nodes in the brain of the subject;

sensing, using one or more electroencephalography (EEG) electrodes arranged on a scalp of the subject, a plurality of TMS-evoked potentials in response to sequentially stimulating the plurality of locations within the brain region of the subject using TMS; and determining, based at least in part on at least one characteristic of the plurality of TMS-evoked potentials, personalized stimulation parameters for the subject, wherein the personalized stimulation parameters include a location of stimulation within the brain region and one or more stimulation characteristics, the one or more stimulation characteristics including a personalized intensity of stimulation.

2. The method of claim 1, wherein the one or more stimulation characteristics further include a personalized frequency of stimulation.

3. The method of claim 1, further comprising:
sensing a resting motor threshold in response to providing non-invasive stimulation of a motor cortex region of the brain of the subject;
determining a baseline intensity of stimulation based, at least in part, on the resting motor threshold; and
adjusting the baseline intensity of stimulation based, at least in part, on the personalized intensity of stimulation.

4. The method of claim 1, wherein the brain region is a node of a Default Mode Network (DMN).

5. The method of claim 1, further comprising providing non-invasive stimulation to the determined location of stimulation of the brain of the subject according to the determined one or more stimulation characteristics, wherein the non-invasive stimulation comprises at least one of transcranial electrical stimulation or transcranial magnetic stimulation.

6. The method of claim 5, wherein the non-invasive stimulation provided to the determined location of stimulation is combined with a different non-invasive stimulation, delivered sequentially or simultaneously, including transcranial electrical stimulation.

7. The method of claim 1, wherein determining the personalized stimulation parameters comprises selecting a location of stimulation from the plurality of locations having a largest peak magnitude of the plurality of TMS-evoked potentials.

8. The method of claim 1, wherein the at least one characteristic of the plurality of TMS-evoked potentials comprises a signal amplitude.

9. The method of claim 1, wherein sequentially stimulating using transcranial magnetic stimulation (TMS) comprises sequentially stimulating using single-pulse TMS.

10. A system for determining personalized stimulation parameters for non-invasive stimulation of a brain of a subject, the system comprising:
a stimulation device configured to sequentially stimulate using transcranial magnetic stimulation (TMS), each of a plurality of locations within a brain region of the subject, the brain region forming a node of a network of connected nodes in the brain of the subject;
a sensor device including one or more electroencephalography (EEG) electrodes configured to sense, in response to the sequential stimulation of the plurality of locations within the brain region, a plurality of TMS-evoked potentials; and
a processor configured to determine personalized stimulation parameters for the subject based at least in part on at least one characteristic of the plurality of TMS-evoked potentials, wherein the personalized stimulation parameters include a location of stimulation within the brain region and one or more stimulation characteristics, the one or more stimulation characteristics including a personalized intensity of stimulation.

11. The system of claim 10, wherein the one or more stimulation characteristics further include a personalized frequency of stimulation.

12. The system of claim 10, wherein the sensor device is further configured to sense a resting motor threshold in response to providing non-invasive stimulation of a motor cortex region of the brain of the subject; and the processor is further configured to i) determine a baseline intensity of stimulation based, at least in part, on the resting motor threshold; and ii) adjust the baseline intensity of stimulation based, at least in part, on the personalized intensity of stimulation.

13. The system of claim 10, wherein the brain region is a node of a Default Mode Network (DMN).

14. The system of claim 10, wherein the stimulation device is further configured to provide non-invasive stimulation to the determined location of stimulation of the brain of the subject according to the determined one or more stimulation characteristics, wherein the non-invasive stimulation comprises at least one of transcranial electrical stimulation or transcranial magnetic stimulation.

15. The system of claim 14, wherein the non-invasive stimulation provided to the determined location of stimulation is combined with a different non-invasive stimulation, delivered sequentially or simultaneously, including transcranial electrical stimulation.

16. The system of claim 10, wherein determining the personalized stimulation parameters comprises selecting a location of stimulation from the plurality of locations having a largest peak magnitude of the plurality of TMS-evoked potentials.

17. The system of claim 10, wherein the at least one characteristic of the plurality of TMS-evoked potentials comprises a signal amplitude.

18. The system of claim 10, wherein the stimulation device is configured to sequentially stimulate each of the plurality of locations within a brain region of the subject using single-pulse TMS.

\* \* \* \* \*